US012426795B2

United States Patent
Cima et al.

(10) Patent No.: US 12,426,795 B2
(45) Date of Patent: Sep. 30, 2025

(54) DEVICES AND METHODS FOR ASSESSMENT OF FLUID DISTRIBUTION IN MUSCLE TISSUE

(71) Applicant: Massachusetts Institute of Technology, Cambridge, MA (US)

(72) Inventors: Michael J Cima, Winchester, MA (US); Ashvin Bashyam, Allston, MA (US); Christopher Frangieh, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 452 days.

(21) Appl. No.: 17/604,673

(22) PCT Filed: Apr. 24, 2020

(86) PCT No.: PCT/US2020/029881
§ 371 (c)(1),
(2) Date: Oct. 18, 2021

(87) PCT Pub. No.: WO2020/219924
PCT Pub. Date: Oct. 29, 2020

(65) Prior Publication Data
US 2022/0218221 A1 Jul. 14, 2022

Related U.S. Application Data

(60) Provisional application No. 62/837,970, filed on Apr. 24, 2019.

(51) Int. Cl.
*A61B 5/055* (2006.01)
*A61B 5/00* (2006.01)
(Continued)

(52) U.S. Cl.
CPC ............ *A61B 5/055* (2013.01); *A61B 5/4519* (2013.01); *A61B 5/4878* (2013.01);
(Continued)

(58) Field of Classification Search
CPC ... A61B 2576/00; A61B 5/055; A61B 5/4519; A61B 5/4878; G01R 33/3808; G01R 33/383; G01R 33/448
See application file for complete search history.

(56) References Cited

U.S. PATENT DOCUMENTS

2016/0120438 A1  5/2016  Cima et al.
2017/0325710 A1  11/2017  Ryan et al.
(Continued)

FOREIGN PATENT DOCUMENTS

DE    102015226160 A1  6/2017

OTHER PUBLICATIONS

Bashyam et al., "Portable single-sided MR: multicomponent T2 relaxometry and depth profiling with a Unilateral Linear Halbach Sensor," International Society for Magnetic Resonance in Medicine, No. 30, Jun. 1, 2008.
Araujo, et al., "New Insights on Human Skeletal Muscle Tissue Compartments Revealed by In Vivo T2 NMR Relaxometry," Biophysical Journal, vol. 106, No. 10, May 21, 2014 (pp. 2267-2274).
(Continued)

*Primary Examiner* — Michael T Rozanski
(74) *Attorney, Agent, or Firm* — Eversheds Sutherland (US) LLP

(57) ABSTRACT

Devices and methods are provided for non-invasive sensing of tissue fluid distribution in a patient. The device includes one or more magnets configured to provide a static magnetic field source; one or more RF transmitter coils connected to a pulse sequence generator which are configured to apply a varying magnetic field to tissues of the patient; one or more RF receiver coils configured to detect a magnetic field generated within tissues of the patient; and a signal acquisition and processor system configured to acquire signals
(Continued)

from the RF receiver coils and perform an NMR measurement of a relaxation parameter of hydrogen nuclei within a muscle tissue site of the patient. A single-sided MR sensor device may include permanent magnets arranged in a unilateral linear Halbach array; and RF coils and a processor which are configured to produce a depth-resolved, diffusion-weighted, multicomponent T2 relaxometry measurements of intramuscular fluid shifts in a patient.

19 Claims, 34 Drawing Sheets

(51) Int. Cl.
    *G01R 33/38*     (2006.01)
    *G01R 33/383*     (2006.01)
    *G01R 33/44*     (2006.01)

(52) U.S. Cl.
    CPC ....... *G01R 33/3808* (2013.01); *G01R 33/383* (2013.01); *G01R 33/448* (2013.01); *A61B 2576/00* (2013.01)

(56) References Cited

U.S. PATENT DOCUMENTS

| | | |
|---|---|---|
| 2018/0306879 A1 | 10/2018 | Bashyam et al. |
| 2019/0076080 A1 | 3/2019 | Prado |
| 2020/0383574 A1 | 12/2020 | Cima et al. |
| 2022/0110580 A1* | 4/2022 | Bashyam ............... G01R 33/50 |

OTHER PUBLICATIONS

Ababneh, et al., "Biexponential parameterization of diffusion and Ts relaxation decay curves in a rat muscle edema model: Decay curve components and water compartments," Magnetic Resonance in Medicine, vol. 54, No. 3, Sep. 1, 2005 (pp. 524-531).

International Society for Magnetic Resonance in Medicine, ISMRM, 2030 Addison Street, 7th Floor, Berkeley, CA 94704 USA, No. 30, Jun. 1, 2018 (Jun. 1, 2018), XP040699239.

Ran Jun et al: "The diagnostic value of biexponential apparent diffusion coefficients in myopathy", Journal of Neurology—Zeitschrift Fuer Neurologie, Springer Verlag, Berlin, DE, vol. 263, No. 7, May 3, 2016, pp. 1296-1302, XP035993931, ISSN: 0340-5354, DOI: 10.1007/ S00415-016-8139-7 , [retrieved on May 3, 2016].

* cited by examiner

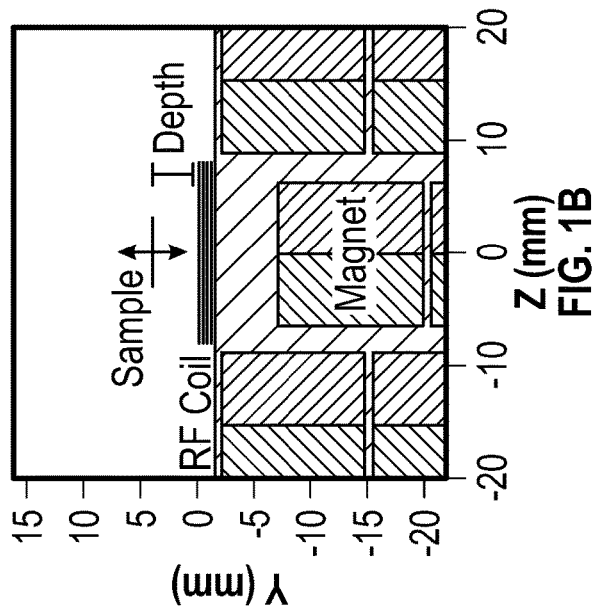
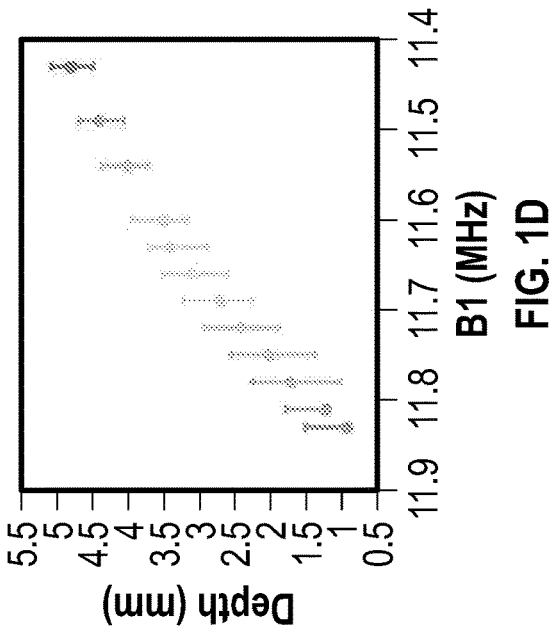
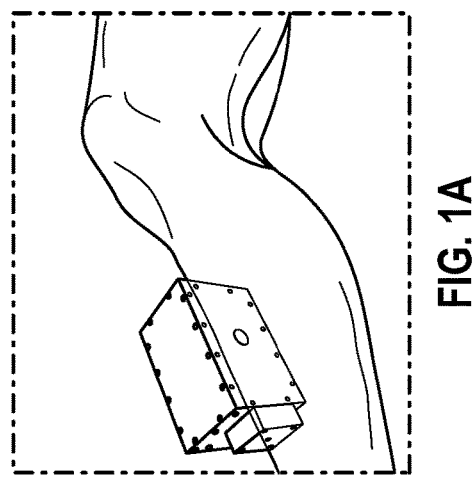
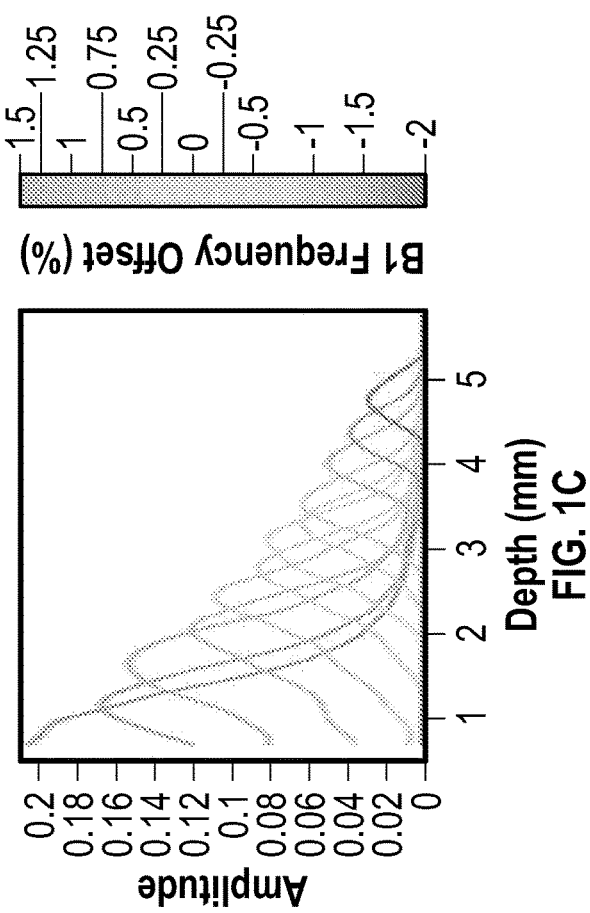
FIG. 1A
FIG. 1B
FIG. 1C
FIG. 1D

DEVICES AND METHODS FOR ASSESSMENT OF FLUID DISTRIBUTION IN MUSCLE TISSUE

CROSS-REFERENCE TO RELATED APPLICATIONS

This application is a national stage entry based on PCT/US2002/029881, filed Apr. 24, 2020, which claims priority to U.S. Provisional Patent Application No. 62/837,970, filed Apr. 14, 2019, both of which are incorporated herein by reference.

BACKGROUND

The present disclosure is generally in the field of medical diagnostics, including, but not limited to non-invasive sensing of tissue fluid distribution in a patient, and more particularly portable magnetic resonance (MR) sensors and methods for intramuscular fluid distribution assessment.

The inability to maintain normal fluid volume status can indicate the progression of a variety of diseases. Fluid overload (hypervolemia) is associated with end-stage renal disease (ESRD), congestive heart failure (CHF), and liver failure. Identification of fluid overload may inform improved treatment for patients with these chronic diseases.

Accurate, real-time monitoring of volume status would improve outcomes for ESRD patients. ESRD patients have excess fluid regularly removed via hemodialysis (HD). Ultrafiltration goals during HD are guided by estimated euvolemic weight (i.e., dry weight) of the patient. The removal of excess fluid beyond that necessary to reach dry weight leads to intradialytic hypotension (IDH). IDH occurs in up to 75% of hemodialysis patients and can cause nausea, vomiting, cramping, and chest pain. This negatively affects patient quality of life and reduces long-term compliance with HD prescription. Furthermore, IDH is associated with increased two-year mortality and morbidity in the form of bowel ischemia, stroke, fistula thrombosis, and myocardial infarction. There currently exists no reliable, robust indication of when HD patients are at risk for IDH.

Current techniques for the identification and treatment of fluid overload are unable to provide a valid assessment of volume status consistent across HD sessions and HD patients. Existing management efforts rely heavily on clinical signs and patients' weight change throughout the course of a HD session. These techniques do not resolve individual fluid compartments and are easily confounded by changes in nutrition, lean body mass, diet, and many other factors. Alternative techniques for indicating a patient's dry weight, such as bioimpedance, blood pressure, and biochemical markers similarly rely on systemic physiological changes and therefore exhibit large interpatient and intrapatient variability.

In sum, existing techniques for diagnosis of fluid volume disorders are inaccurate, invasive, or easily confounded by patient physiology. It therefore would be desirable to provide improved devices and methods for assessing fluid distribution in patients.

BRIEF SUMMARY

Improved MR devices for fluid assessment is targeted tissue sites are provided, which for example may detect an expanded muscle extracellular space.

In one aspect, a device is provided for non-invasive sensing of tissue fluid distribution in a patient, wherein the device comprises: (i) one or more magnets configured to provide a static magnetic field source; (ii) one or more RF transmitter coils connected to a pulse sequence generator which are configured to apply a varying magnetic field to tissues of the patient; (iii) one or more RF receiver coils configured to detect a magnetic field generated within tissues of the patient; and (iv) a signal acquisition and processor system configured to acquire signals from the one or more RF receiver coils and perform an NMR measurement of a relaxation parameter of hydrogen nuclei within a muscle tissue site of the patient. The muscle tissue site may be skeletal muscle tissue, for example, the calf muscle or another muscle in an extremity of the patient. In particular embodiments, the device is configured to use depth-resolved, diffusion-weighted, single-sided magnetic resonance (MR) to measure the relaxation parameter within the muscle tissue of the patient. For example, the device may be configured to use a combination of multicomponent T2 relaxometry, measurement localization, and diffusion weighting to identify shifts in intramuscular fluid distribution.

In other aspects, methods for device operation and optimization are provided.

BRIEF DESCRIPTION OF THE DRAWINGS

FIG. 1A illustrates one embodiment of a portable MR sensor in use positioned adjacent to a lower leg of human subject.

FIG. 1B is a schematic of one embodiment of an experimental schematic of an MR sensor to characterize the sensitivity profile versus depth.

FIG. 1C is a graph illustrating the sensitivity of one embodiment of the sensor as a function of sample depth and RF excitation frequency, which shows that tuning the RF pulse frequency allows for adjustable sensitivity along the depth axis. Decreased B1 frequency enables deeper measurements remote from the surface of the sensor. Shaded regions indicate 95% confidence intervals of amplitude estimates.

FIG. 1D is a graph showing the projection of each curve onto the depth axis, according to one embodiment, which shows an RF pulse bandwidth of ~0.7% excites slices 0.6 to 1.3 mm thick with slice thickness decreasing further from the surface of the sensor. Circles indicate the depth of the peak of each sensitivity profile. Whiskers indicate slice thickness defined as full width at half maximum.

FIG. 2A is a graph showing time domain CPMG decay curves, and FIG. 2B is a graph showing triexponential relaxation peaks of signal acquired from ex vivo muscle, fat, and hybrid sample. FIG. 2C is a histogram indicating the distribution of estimation errors of the constituent tissue fractions within the hybrid sample upon repeated trials.

FIG. 3A is an experimental schematic identifying planar subcutaneous and muscle tissue samples on top of portable MR sensor. FIG. 3B is a schematic illustrating the use of the depth sensitivity profiles to estimate the thickness of a tissue layer. FIG. 3C is a graph showing experimentally measured and predicted muscle signal fractions from each unique subcutaneous tissue thickness versus RF excitation frequency. FIG. 3D is a graph showing thickness estimation error versus predicted thickness for each unique subcutaneous tissue thickness. Dotted lines indicate the estimated synthetic tissue thickness, corresponding to the minima of each error curve. Shaded regions indicate 0.3 mm uncertainty in the true thickness of each subcutaneous tissue layer.

FIG. 4A shows time domain decay curves, and FIG. 4B shows extracted relaxation times, from measurement of samples with distinct diffusivities acquired with CPMG on benchtop NMR spectrometer. Error bars represent 95% confidence intervals on relaxation time estimates. FIG. 4C shows diffusivity estimated via pulsed gradient spin echo measurements of these samples with an NMR spectrometer. FIGS. 4D, 4E, and 4F show time domain decay curves, relaxation times, and relaxation times, respectively, normalized to the relaxation time at TE=206 μs from measurements of these samples on portable MR sensor with CPMG with varying echo time. Error bars represent 95% confidence intervals on the relaxation time estimates. FIG. 4G shows time domain CPMG decay curves of ex vivo tissue measured with portable MR sensor at two echo times. FIG. 4H shows slow amplitude ($amp_2$) and FIG. 4I shows slow amplitude normalized to slow amplitude at TE=65 μs of a biexponential fit on these measurements. Error bars represent 95% confidence intervals on amplitude.

FIGS. 5A-5B show H&E stains of biceps femoris muscle before (FIG. 5A) and after (FIG. 5B) intramuscular injection of λ-carrageenan, which shows acute inflammation and interstitial expansion. FIGS. 5C-5D show T2 weighted MRI images of rat lower leg before (FIG. 5C) and after (FIG. 5D) onset of acute muscle edema. FIG. 5E shows decay curves from T2 relaxometry acquired via MRI before and after onset of muscle edema, showing a difference in decay rate. Shaded regions indicate variance in signal generated through bootstrapping. FIG. 5F shows relative amplitudes of biexponential fits (Eq. 3) on control and edema echoes. Relaxation times are derived from a biexponential fit (Eq. 2) on the mean of all echoes.

FIG. 6A is an illustration of a portable MR sensor with synthetic subcutaneous tissue phantom placed between a RF transceiver coil and a rat lower leg. FIGS. 6B-6C are graphs showing time domain decay curves from portable MR measurement of the rat leg at an RF excitation frequency of 11.83 MHz (FIG. 6B) and 11.43 MHz (FIG. 6C). FIG. 6D is a graph showing slow amplitude of triexponential fit on 11.43 MHz and 11.83 MHz measurements. FIG. 6E is a graph showing amplitude attributed to muscle ECF and subcutaneous signal from a five exponential fit on 11.43 MHz and 11.83 MHz measurements. FIG. 6F is a graph showing amplitude attributed to muscle ECF from 11.60 MHz measurements at echo times of 65 μs and 260 μs. Black dashed line indicates estimated muscle edema derived from both measurements. All error bars indicate 95% confidence intervals on amplitude estimates.

(FIG. 14A) and spin echo length (defined as full-width at half max) versus B1 frequency (FIG. 13B), according to one embodiment.

FIGS. 19B-19C show magnetic field strength deviation from B0 along y-axis and z-axis, respectively, through the center of uniform region. Shaded regions correspond to ±1% deviation from B0.

FIG. 23A shows a single magnet. FIGS. 23B-23C show an concave arrangement of a plurality of magnets.

DETAILED DESCRIPTION

Figure 2A:
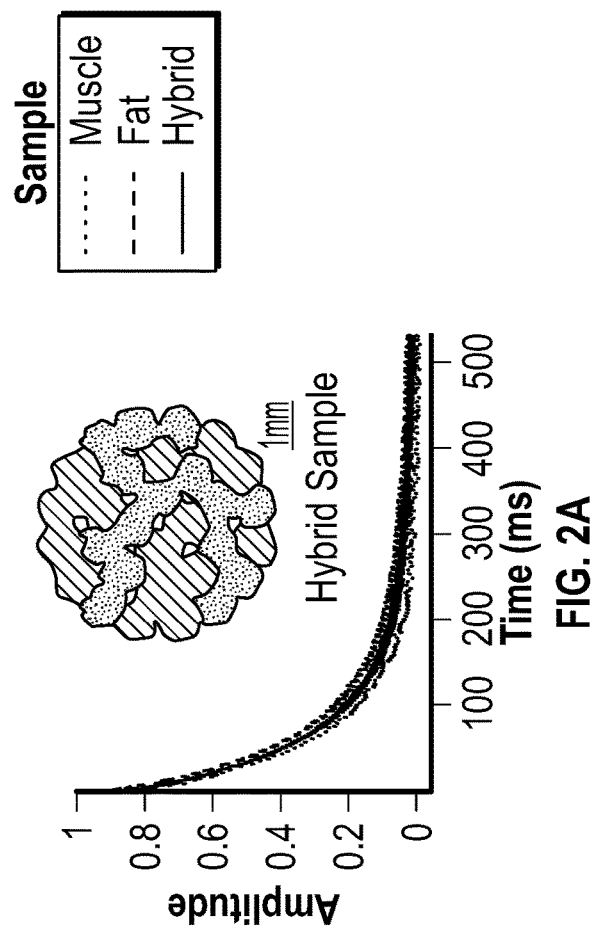
FIGS. 2A-2C show how multicomponent T2 relaxometry allows estimation of tissue fraction from a heterogeneous sample.

Systems and devices have been developed for assessment of fluid distribution in muscle tissue using depth-resolved, diffusion-weighted, single-sided magnetic resonance (MR). In some embodiments, the devices and systems are configured to use a combination of multicomponent T2 relaxometry, measurement localization (e.g., by tuning RF excitation frequency), and diffusion weighting (e.g., by varying echo time) to improve the ability of portable, single-sided MR sensors to identify shifts in intramuscular fluid distribution.

The portable, non-invasive sensors of tissue fluid distribution described herein can aid in diagnosis of fluid volume disorders and inform therapeutic decisions across diverse patient populations. In some embodiments, the device is a single-sided MR sensor device which can provide a portable, low-cost platform for localized measurements of intramuscular fluid distribution. In particular, the single-sided MR sensor can quantify fluid distribution of heterogeneous samples via depth-resolved, diffusion-weighted, multicomponent T2 relaxometry.

The portable MR sensor offered many advantages over traditional MRI. Its miniature size and low power consumption, both realized through the use of permanent magnets rather than superconducting coils, offer a mobile platform capable of performing measurements across a wide range of environments including hospitals, outpatient facilities, sporting events, and military operations. The device is straightforward to operate as there is no need for any user controlled acquisition parameters. Furthermore, the interpretation of the measurement is fully automated in contrast to traditional MRI. The potential to perform these MR measurements without a trained operator or radiologist for image interpretation may increase accessibility of fluid volume status measurements. Finally, the measurement can be performed in a few minutes for use as a real-time measure of fluid volume status.

The ability to accurately monitor the volume status of end-stage renal disease patients during hemodialysis can inform fluid removal and improve treatment outcomes. Excess fluid removal induces intradialytic hypotension, which is associated with adverse outcomes including increased mortality and decreased long-term compliance with hemodialysis prescription. The majority of patients undergoing conventional hemodialysis will experience intradialytic hypotension. Improved identification of overload in these patients may better inform fluid removal during hemodialysis to achieve dry weight while avoiding intradialytic hypotension. The portable, non-invasive MR sensor of tissue fluid distribution described herein can provide information on systemic volume status via measurements localized to the muscle.

The devices and method described herein advantageously interrogate the underlying physiology as multicomponent T2 relaxometry directly resolves the extracellular and intracellular fluid spaces. This differs from conventional methods used to manage patients with fluid disorders. In hemodialysis patients, for example, blood pressure is commonly used to assess volume status. However, blood pressure measurements are unable to specifically identify systemic fluid shifts, as they cannot distinguish between changes in systemic volume status and in cardiovascular function due to disease. Similarly, dehydration is often assessed via body weight change, but variability in body composition between patients prevents this simple measure from accurately identifying the onset of clinical dehydration. Ultimately, these conventional techniques do not interrogate the status of the muscle, which serves as the primary fluid reservoir in both fluid overload and depletion. The present methods and devices overcome these limitations and, therefore, serve as a useful diagnostic of disorders in fluid volume status.

In some embodiments, the selected combination of (i) multicomponent T2 relaxometry, (ii) measurement localization, e.g., by tuning RF excitation frequency, and (iii) diffusion weighting by varying echo time enables a single-sided MR sensor to identify shifts in intramuscular fluid distribution. Accordingly, these measurement techniques have the potential to improve the management of patients undergoing HD through real-time monitoring of fluid volume status.

The present portable, single-sided MR sensor offers many advantages over both traditional MRI and other measurements of fluid overload. The portable MR sensor offers a miniature, low power consumption platform capable of deployment across many environments including both inpatient and outpatient dialysis units. The operation of the device and interpretation of its results can be fully automated. This is critical to ensure widespread adoption by clinical staff (e.g., nurses, technicians). In contrast, conventional approaches such as blood pressure or blood chemistry require a trained operator and access to laboratory facilities for accurate measurements.

The methods and devices configured as described herein enable the use of single-sided MR sensors to interrogate muscle tissue across diverse patient populations. In some embodiments, the device comprises a single-sided MR device based on the Unilateral Linear Halbach magnet array (Bashyam, et al., *J. Magn. Reson.* 292: 36-43 (2018)). This design enables high sensitivity, remote MR measurements via compact permanent magnet array. Since subcutaneous tissue can confound measurement of the muscle, and its thickness varies among patients, the RF excitation frequency of the MR device is tuned to enable measurements at an increased depth and thereby avoid more proximal subcutaneous tissue. Additionally, the MR device is adapted to use of diffusion weighted measurements which allows for further isolation of the signal towards the muscle.

Modifications to the MR sensor and the described methods are envisioned, which may improve the ability of the MR sensor to perform measurements of intramuscular tissue fluid distribution. For example, diffusivity was not directly quantified in these measurements described in the examples because of the presence of a spatially varying static magnetic field gradient and restricted diffusion within tissues, but additional characterization of the sensor could extract an accurate estimate of diffusivity. The CPMG pulse sequence was utilized in the examples to take advantage of its high sensitivity, robustness to field inhomogeneity and simplicity. Hardware limitations in the example sensor prevented implementation of more sophisticated pulse sequences that more directly enable estimation of sample diffusivity versus T2. An improved pulse sequence could simultaneously acquire depth-resolved, diffusion-weighted T2 measurements. However, quantitative parameter extraction is not necessary for the present devices and methods to provide diagnostic value, for example, because empirical thresholds can be derived through further clinical studies.

In embodiments, several enhancements to the portable MR sensor design and MR pulse sequences may improve measurement accuracy and reduce variability to enhance the potential for clinical translation. The relatively inhomogeneous field and imperfect refocusing pulse flip angle likely created stimulated echoes from additional coherence pathways during portable MR measurements. This can bias the estimation of T2 and lead to overestimation of the T2 especially in tissues with a high T1 to T2 ratio. The use of a pulse sequence with reduced stimulated echoes may allow direct comparison of relaxation times between different MR systems and a more thorough investigation of shifts in relaxation time with change in fluid volume status.

In some embodiments, the sensor is configured to perform a deeper measurement through improved magnet design, which may reduce the potential for confounding signals from more proximal tissue layers such as the dermis and subcutaneous tissue. Other strategies to overcome confounding signal from the proximal subcutaneous tissue include first measuring its thickness and then estimating the signal contribution originating from the muscle. In some embodiments, isolation of the muscle tissue may be achieved through improved pulse sequences. For example, the addition of diffusion-weighted scans may help isolate the muscle tissue for further analysis. In this way, the sensor may be able to perform an absolute measure of fluid volume status in subjects with variability in subcutaneous thickness. This would obviate the need for a baseline measurement at euhydration allowing for use as both a monitor of changes in hydration state and an absolute diagnostic of dehydration.

Figure 22A:
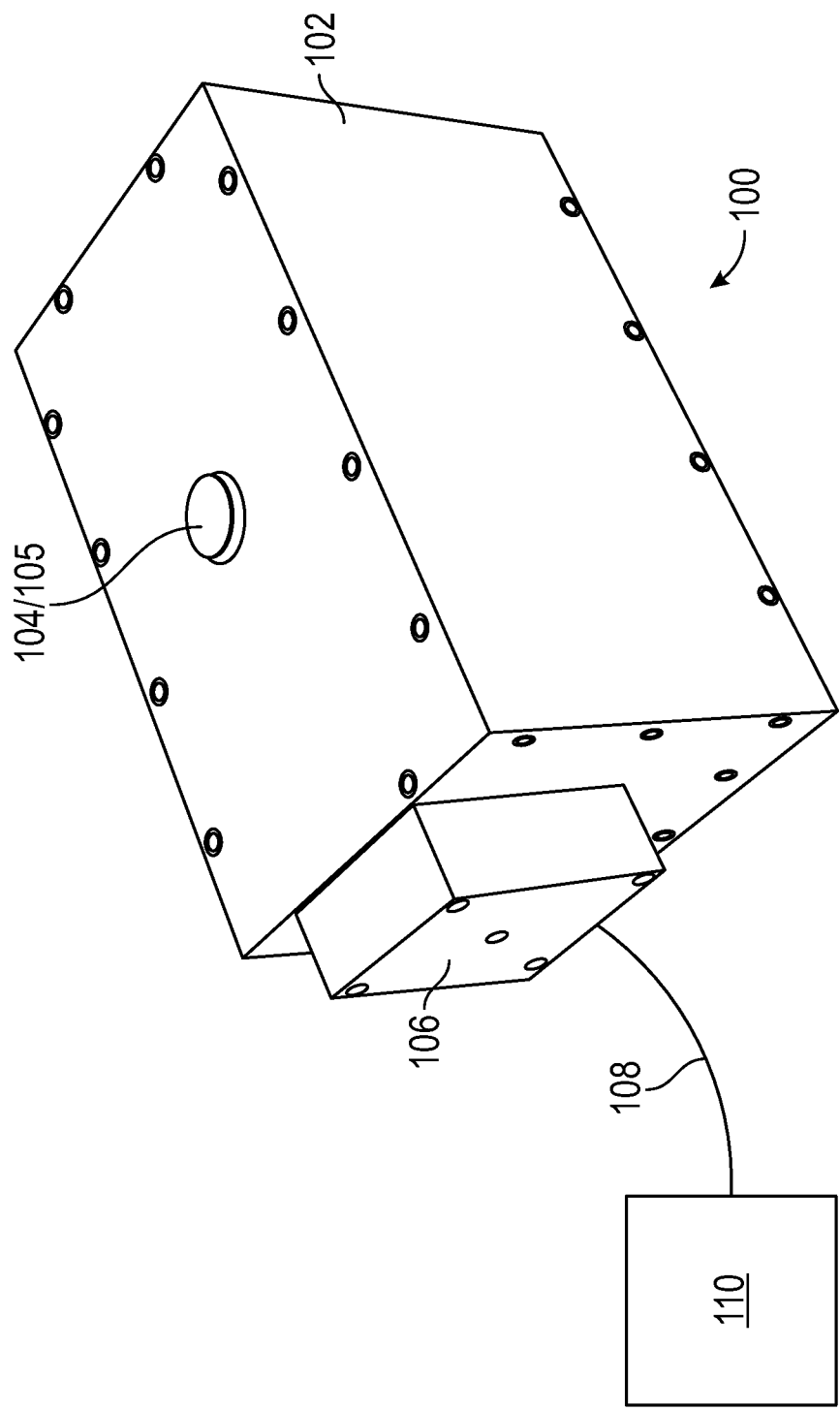
FIG. 22A is a perspective view of one embodiment of a fully assembled sensor with RF matching circuit and solenoidal transceiver coil.
Figure 22B:
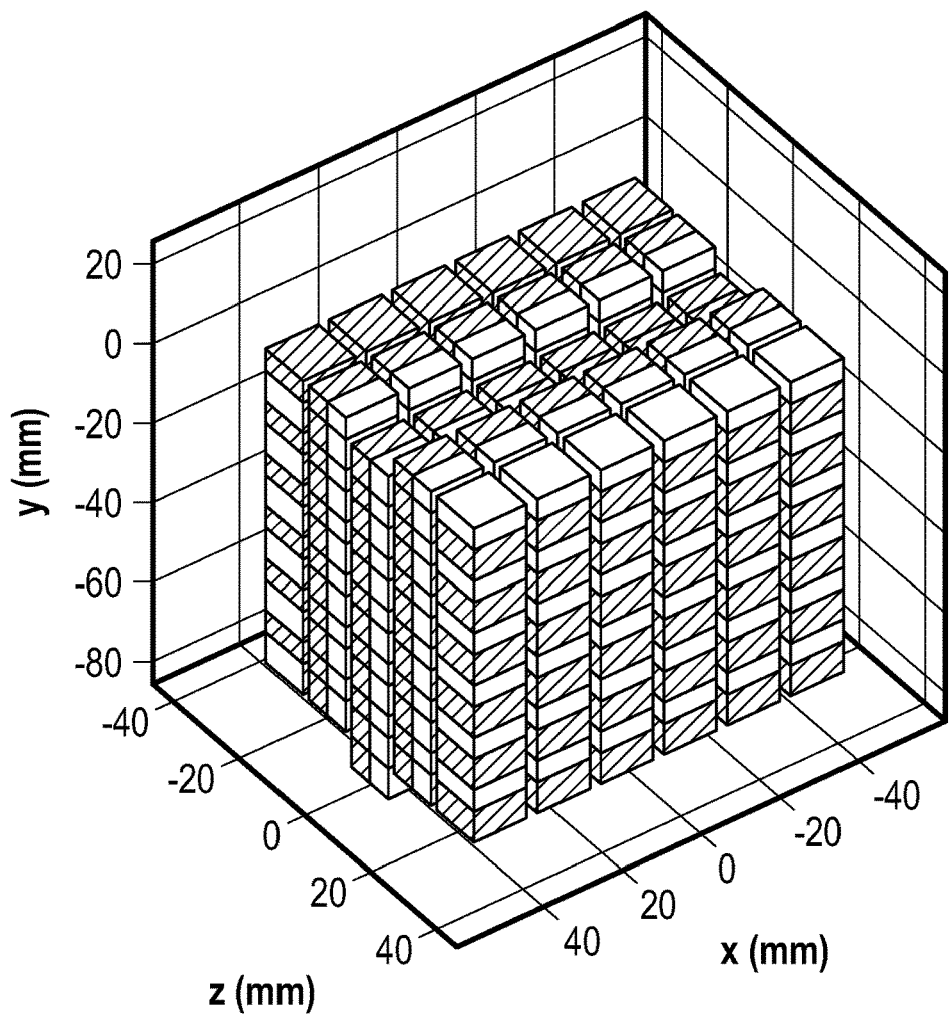
FIG. 22B is a perspective view of one embodiment of a unilateral Linear Halbach permanent magnet array design for sensor. Shading/color difference indicates positive and negative poles of each magnet.

FIG. 22A illustrates one embodiment of a device for non-invasive sensing of tissue fluid distribution in a patient. The device 100 includes a housing 102 containing one or more magnets (not visible here, but shown in FIG. 22B) configured to provide a static magnetic field source; one or more RF transmitter coils 104 connected to a pulse sequence generator which are configured to apply a varying magnetic field to tissues of the patient; one or more RF receiver coils 105 configured to detect a magnetic field generated within tissues of the patient; and a signal acquisition and processor system 110 configured to acquire signals from the one or more RF receiver coils and perform an NMR measurement of a relaxation parameter of hydrogen nuclei within a muscle tissue site of the patient. The device 106 further includes RF electronics 106 which includes matching circuit, and an electrical connection to the signal acquisition and processor system 110. The RF electronics 106 may be configured as a broadband matching circuit to provide broadband match across a wide range of frequencies or rapid, automated tuning.

The RF transmitter coil 104 and the RF receiver coil 105 may be the same physical coil, or they may be two distinct coils. These coils may be either spatially coincident or can take on different geometries, shapes, and/or positions.

Figure 24A:
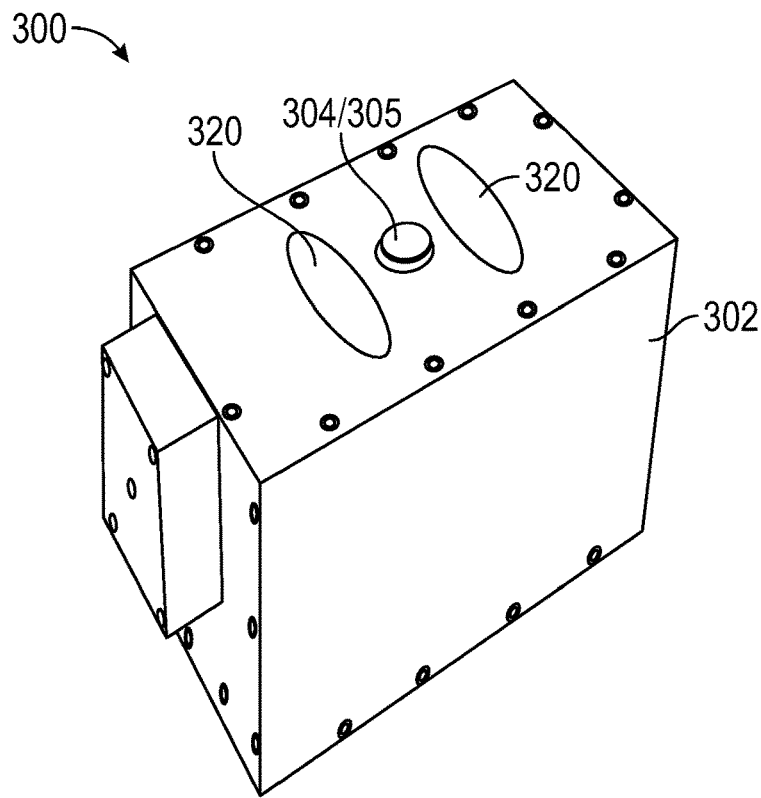
FIGS. 24A-24B are perspective views of two embodiments of an MR sensor with gradient encoding coils.
Figure 24B:
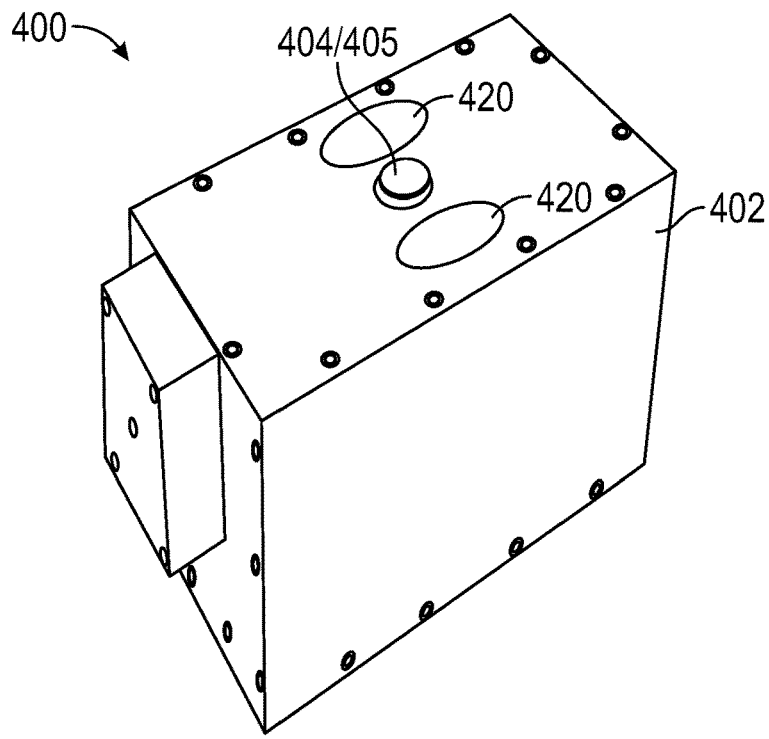

FIG. 24A shows another embodiment of a sensor device. The device 300 includes housing 302, magnets within the housing (not visible), RF transmitter and receiver coils 304/205, as well as gradient encoding coils 320. An alternative position (and/or shape) of gradient encoding coils is shown in FIG. 24B. Here, the device 400 includes housing 402, magnets within the house (not visible), RF transmitter and receiver coils 404/405, as well as gradient encoding coils 420.

Figure 25:
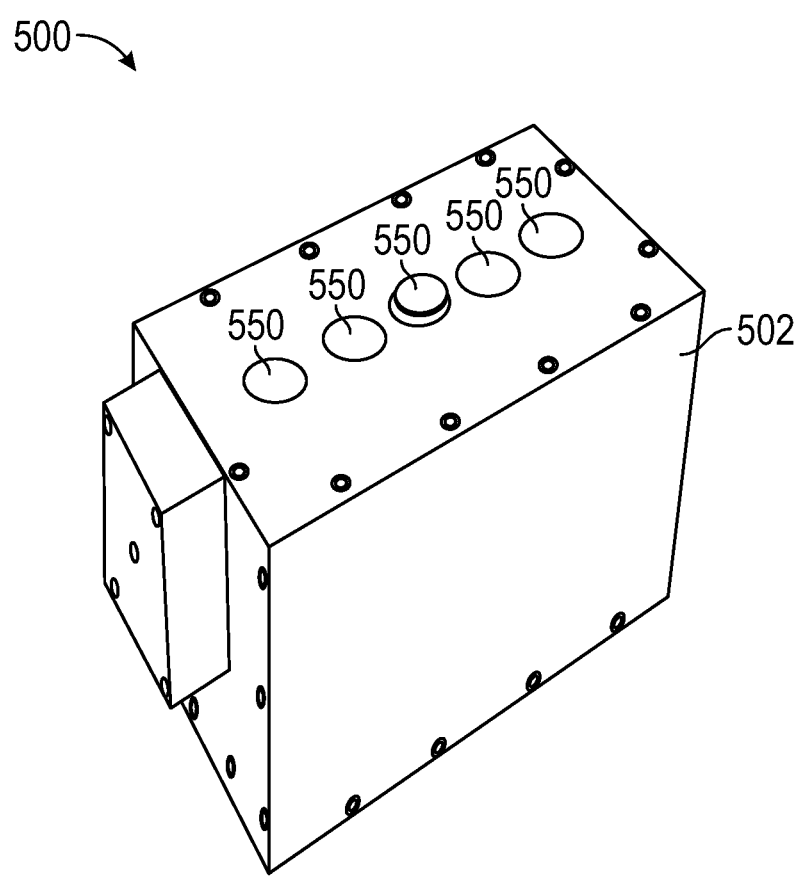
FIG. 25 is a perspective view of one embodiment of an MR sensor with multiple transceiver coils.

FIG. 25 shows another embodiment of a sensor device. The device 500 includes housing 502, magnets within the housing (not visible), and multiple transceiver coils 550. In this embodiment, a linear array of five transceiver coils is provided, although other numbers and positions of the transceiver coils is envisioned.

In some embodiments, the sensor may include a broadband matching circuit for rapid automatic tuning; gradient encoding coils to facilitate diffusion-weighted acquisition; multiple transceiver coils for parallel acquisition at different points of the patient's body; or a combination of these structures/features.

In the examples described below, validation is provided using synthetic tissue phantoms, ex vivo tissue samples, and an in vivo edema model. Estimation of tissue fractions in heterogeneous samples are demonstrated with 2% error and tissue layer thickness with 0.1 mm error. The sensor can identify onset (p<0.0001) progression (p<0.01), and recovery (p<0.0001) of muscle edema despite the presence of a confounding subcutaneous tissue layer. These methods can provide point-of-care diagnostics for fluid distribution disorders such as end-stage renal disease and dehydration.

Context Information

Disruptions in fluid volume status are characterized by changes in the distribution of water between body fluid compartments and tissues. Hypovolemia and hypervolemia induce respective depletion and expansion of the intramuscular fluid compartments (extracellular and intracellular). Furthermore, the intramuscular extracellular fluid (ECF) compartment is more highly responsive to these fluid shifts than the intracellular fluid (ICF) compartment and either compartment in the subcutaneous space. Therefore, a localized measurement of shifts in fluid within the intramuscular fluid compartments may serve as an indicator of disruption to systemic euvolemia.

Magnetic resonance measurements of distinct fluid compartments have demonstrated sensitivity to both local and systemic shifts in tissue fluid distribution. A clinical study in ESRD patients undergoing HD was conducted to assess the ability of MR measurements localized to the skeletal muscle to identify changes in fluid volume status. This study showed that the change in amplitude of the multicomponent T2-based signal corresponding to intramuscular ECF in a localized measurement can identify systemic fluid imbalances. This clinical study also demonstrated the need for improved measurement localization within the muscle to make an absolute determination of volume status. These findings were corroborated in a rodent model of fluid depletion and demonstrated sensitivity towards weight loss via both systemic and localized measurements. However, MRI is impractical for use as a routine clinical diagnostic due to its resource intensiveness, high cost, long acquisition time, and lack of portability. Portable MR sensors have exhibited sensitivity towards fluid distribution in tissues, including the muscle, in both animal and human studies. This resolves many of the limitations of MRI by providing a portable, low-cost, high sensitivity platform to perform MR measurements. In the clinical study, the portable MR sensor was unable to reproduce absolute measurements of fluid volume status as seen on the MRI of skeletal muscle due to the highly variable subcutaneous tissue thickness between patients.

Portable MR devices, often realized via single-sided magnets, can be inadequate in their ability to isolate the measurement towards the muscle tissue due to limitations in penetration depth, spatial selectivity, and available contrast mechanisms. Measurement of skeletal muscle tissue in the extremities requires penetration beyond the proximal subcutaneous tissue. Measurement depth is highly constrained due to the rapid attenuation of static and RF magnetic fields away from the surface of the sensor. Larger devices can achieve increased penetration depth, but this compromises portability and increases cost. Encoding spatial information via switchable gradients is substantially more difficult with single-sided MR sensors compared to MRI due to the high field inhomogeneity of their static and gradient magnetic fields and restrictions on allowable tissue RF power deposition. Therefore, single-sided MR measurements of the muscle are often contaminated by other nearby tissues. The available contrast mechanisms to help isolate the signal from a single tissue (i.e., muscle) are restricted due to the relatively low sensitivity and high magnetic field inhomogeneity of single-sided MR devices. Many pulse sequences capable of separating fat from other tissues rely on phenomena such as chemical shift, which cannot be realized given the high field inhomogeneity of single-sided MR sensors.

The presence of confounding tissues, such as subcutaneous tissue, can obscure or confound measurements intended to be isolated towards the muscle tissue. Separation of signals originating from tissues with similar relaxation properties is difficult and a substantial source of error in relaxometry studies. Performing multicomponent T2 measurements relatively deep within the tissue with a single-sided MR sensor while maintaining sensitivity is challenging.

Sensor Device

In some embodiments, the sensor is a single-sided MR sensor based on the Unilateral Linear Halbach magnet design, which is capable of identifying intramuscular fluid shifts via a localized measurement. This sensor is capable of performing depth-resolved measurements by tuning the RF excitation frequency. Quantification of the relative fractions of tissues within heterogeneous samples may be obtained via multicomponent T2 relaxometry. The sensor exhibits contrast dependent on the diffusivity of the sample. This capability is leveraged to isolate and characterize tissues with otherwise similar MR relaxation properties. These techniques may then be applied in combination to provide a depth-resolved, diffusion-weighted, multicomponent T2 relaxometry measurement, which can identify and track the onset and progression of muscle edema despite the presence of a confounding proximal subcutaneous tissue layer.

The portable MR sensor may be realized through the use of a Unilateral Linear Halbach magnet geometry. Briefly, this sensor consists of an array of 180 permanent magnets arranged to produce a static magnetic field (0.28 Tesla) with <2% field variation over a volume spanning approximately 12×6×6 mm.

Example 2 below provides detailed descriptions of the design, construction, and characterization of one particular MR sensor suitable for use herein.

In some embodiments, the magnets are configured as described in U.S. Patent Application Publication No. 2018/0306879, entitled "Single-Sided Magnets for Remote Nuclear Magnetic Resonance Measurements" by Bashyam, et al., which is incorporated herein by reference.

These innovations enable miniaturized, single-sided MR sensors to perform measurements of fluid distribution in the muscle tissue, the tissue that is most responsive to disruptions in fluid volume status. This non-invasive, portable, point of care technique has the potential to help diagnose and manage conditions involving disruptions in fluid distribution such as congestive heart failure, end-stage renal disease, and dehydration.

New Portable MR Sensor Designs/Features

Figure 23A:
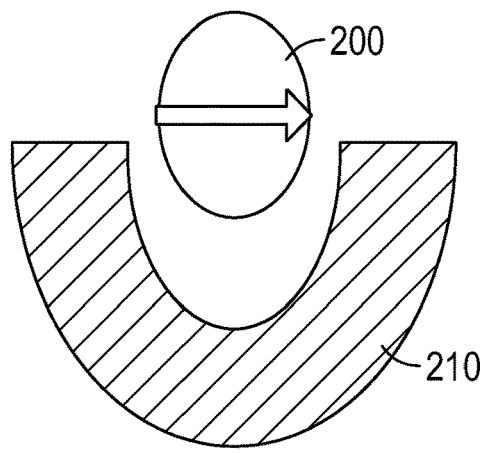
FIGS. 23A-23C illustrate embodiments of one or more magnets having a concave shape or arrangement for enabling the sensor to conform to a patient, e.g., the leg of the patient.
Figure 23B:
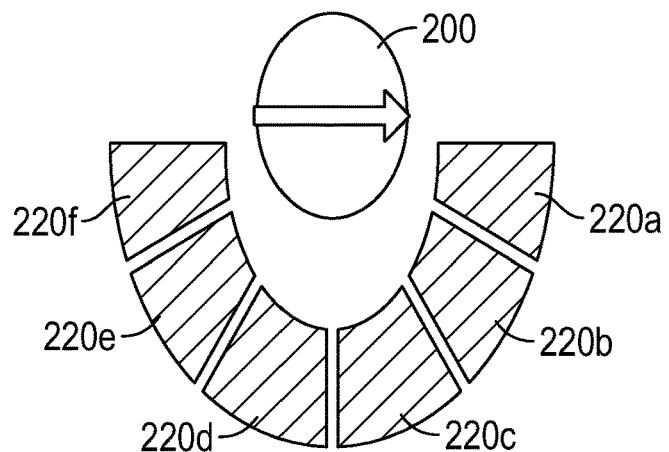

In some embodiments, a new portable MR sensor is provided to allow for increased sensitivity towards human skeletal muscle tissue. For example, the sensor may include a larger magnet design that would straightforwardly allow for increased penetration depth. Further optimization of the Unilateral Linear Halbach array may provide increases in penetration depth. In some embodiments, the magnet may have a concave surface, so that the magnet better conforms to the contour of a patient's lower leg or other extremity, which would increase the amount of magnetic material near the muscle tissue and, therefore, increase the field strength. In some embodiments, the sensor may include a series of magnets provided with curvatures matched to that of the range of anatomy expected in a target patient population. Alternatively, in some embodiments, the sensor may include a deformable magnet geometry that allows a single magnet to adapt to the anatomy of each patient. The geometry could be unilateral or circular to allow for more precise design of the field profile and strength at the tissue of interest. FIG. 23A shows a single concave magnet 210, with a human leg 200 positioned with the concavity and the magnetic field (shown as the arrow passing through the leg 200). FIG. 23B shows a concave arrangement of multiple magnets 220a-220f, with a human leg 200 positioned with the concavity and the magnetic field (shown as the arrow passing through the leg 200).

Figure 23C:
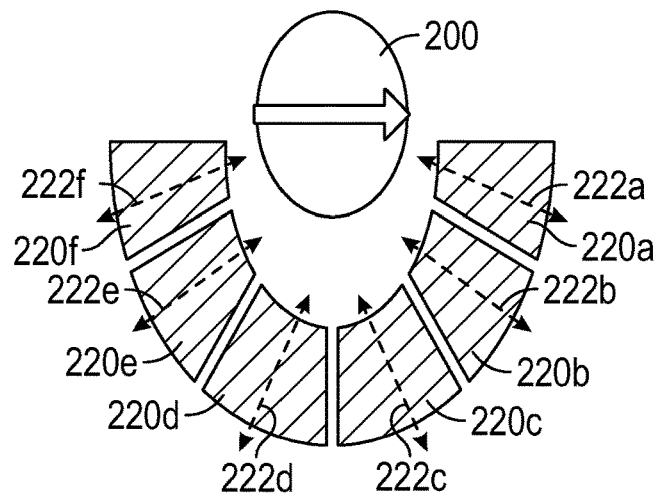

In some embodiments, the magnet includes adjustment shims, operable to compensate for minor imperfections in the magnetization of the constituent permanent magnets. This would result in increased field homogeneity, an increased T2* and ultimately higher sensitivity measurements. In some embodiments, the magnet is fabricated, despite manufacturing challenges, from a few very large permanent magnets to increase the density of magnetic material within the housing. In some embodiments, shimming is tunable in real-time to allow for shimming of the main magnetic field during scanning. This would allow for precision tuning of the sensor sensitive region based on patient physiology, patient disease status, or environmental confounders. FIG. 23C also shows a concave arrangement of multiple magnets 220a-220f, with a human leg 200 positioned with the concavity and the magnetic field (shown as the arrow passing through the leg 200) and further illustrates the directions of movement 222a-222f of each of the magnets in an implementation as part of a shimming system. For example, a wedge or thin strip of material could be inserted adjacent the convex side of each magnet to displace it slightly, along the directions of movement towards, and thereby reduce, the concavity of the arrangement. This functionality enables adjustment of magnet geometry, which may need to be adjusted slightly prior to a measurement or during a measurement.

This could be motivated by patient anatomy which could be observed either prior to the measurement or via the magnetic resonance system during the measurement In some embodiments, the sensor includes the ability to adjust its excitation and acquisition frequency with minimal latency and user interaction. In a current embodiment, the matching circuit requires manual adjustment when the RF frequency is changed since it only provides a very narrowband match. In more preferred embodiments, however, the sensor includes a circuit configured to provide either the ability for a broadband match across a wider range of frequencies or the ability to be rapidly tuned in an automated fashion.

In some embodiments, the sensor includes gradient encoding coils to enable stronger diffusion-weighted acquisition. Existing single sided sensors typically rely on the gradient within the static magnetic field. This provides limited control over the magnitude of diffusion encoding and no control over its direction.

In some embodiments, the sensor includes multiple coils, either separate transmit and receive coils or multiple transceiver coils. Multiple transceiver coils may allow for parallel acquisition of a single patient at different points along their physiology. Parallel scanning of patients will allow for decreased acquisition time without a loss of signal.

Sensor Device and System Configurations

In some embodiments, the portable, single-sided MR sensor is configured to use the combination of three techniques—multicomponent T2 relaxometry, measurement localization by tuning RF excitation frequency, and diffusion weighting by varying echo time—to identify shifts in intramuscular fluid distribution. Variations of each of these techniques may also be used.

In some embodiments, the devices and operating methods described herein utilize, or are adapted from, the measured relaxation parameters and methods for measuring relaxation parameters described at U.S. Patent Application Publication No. 2016/0120438, which is incorporated herein by reference.

Tuning RF Excitation Frequency Enables Slice Selection

In some embodiments, the RF excitation pulse frequency is tuned to control the fraction of proximal subcutaneous versus more distal muscle tissue in the acquired signal. This capability enables targeting of the measurement towards a tissue of interest.

In some other embodiments, other means are used to localize the measurement towards a particular spatial region by exciting nuclei within the sample in a spatially varying manner. One or more pulse sequence parameters can be varied, such as the pulse length, pulse amplitude, or pulse shape. The spatial sensitivity profile can be measured for different values of these parameters by scanning a small reference sample (e.g. planar sample, linear sample, or point sample) and assessing the relative signal strength as a function of both space and pulse sequence parameters.

The optimal pulse sequence can be identified by maximizing a utility function. In one implementation, the pulse sequence that provides maximal sensitivity towards the target region may be selected. This could be implemented by considering the absolute strength of the signal originating within the target region and selecting a pulse sequence for which this signal strength is above a desired threshold. In another implementation, the pulse sequence that provides maximal signal localization towards the target region may be selected. This could be implemented by considering the fraction of the signal that originates within the target region and selecting a pulse sequence for which this fraction is above a desired threshold. This ensures that a substantial portion of the signal is generated by the sample within the target region.

Spatial sensitivity is achieved by assigning signals of a particular frequency range to a particular location (e.g., distance from the sensor). A broadband signal comprises signals originating from spins at a wide range of frequencies. By restricting the frequency bandwidth of this signal to a well-defined range, the signal originating from spins only within a well-defined spatial region can be isolated. This method relies on first determining the relationship between position and precession frequency, which is a function of static magnetic field strength.

One method of performing this selectivity is through the use of narrowband RF excitation pulses and a narrowband receive circuit. In another case, this could be performed with only narrowband RF excitation pulses and a receive circuit with a bandwidth equal to at least that of the RF excitation pulses. This could offer the advantage of potentially faster and more precise switching of frequency, and therefore measurement location. In another case, this could be performed with a broadband RF excitation pulse and one or more narrowband receive circuits. This would offer the advantage of performing spatial localization to multiple regions in parallel for increased acquisition speed. Similarly, the combination of a high bandwidth RF pulse, high bandwidth receive circuit, and high bandwidth digitization electronics would allow a signal with component originating from a wide range of depths to be received and digitized. Selection of location could be performed after signal digitization enabling very fast and parallel analysis of signals originating from multiple regions.

The thickness of the effective slice can be tuned by adjusting pulse parameters (e.g. RF excitation bandwidth, pulse duration, pulse shape, RF excitation frequency).

Multicomponent T2 Relaxometry, Enabling Tissue Fraction Estimation

In some embodiments, the contribution from each tissue is identified to isolate the signals of interest and permit further analysis of their relaxation properties. That is, the identification of tissue fractions are derived from an MR signal acquired with the portable MR sensor. This may be accomplished using an algorithm to estimate the fraction of tissues within the hybrid signal through an iterative approach that minimizes the error between the measured signal and a synthetic signal based on an estimated ratio of constituent tissues. For example, the algorithm may recover the fractions of muscle and fat within the hybrid signal to within a 2% error or better. The technique could be extended to consider multiple signals from each constituent tissue in order to improve its robustness, especially towards complex samples. Two measurements could be performed with different sensitivities towards spin diffusivity, for example, for each constituent tissue and for the hybrid sample. The addition of the second signal would increase the orthogonality of the basis signals, if the constituent samples have differences in diffusivity, and, therefore, may increase the accuracy and/or robustness of the technique in the presence of noise or other confounding signals. This same approach could also be applied with other pulse sequences (e.g. inversion recovery, saturation recovery, stimulated echoes, pulsed gradient echo, etc.) to take advantage of differences in T1, T2, and/or diffusivity in combination.

This technique can be extended towards more than two tissues by allowing the algorithm to consider the weighting of an arbitrary number of constituent, or basis, signals. The technique can also be made more general by replacing the use of a multi-exponential basis with any other basis.

In order to improve the robustness of this technique, especially towards complex samples, it could be extended to consider multiple signals for each constituent tissue. For example, two measurements could be performed with different sensitivities towards spin diffusivity for each constituent tissue and for the hybrid sample. If the constituent samples have differences in diffusivity, then the addition of the second signal increases the orthogonality of the basis signals and, therefore, may increase the accuracy and/or robustness of the technique in the presence of noise or other confounding signals. This same approach may also be applied, potentially with other pulse sequences (e.g., inversion recovery, saturation recovery, stimulated echoes, pulsed gradient echo, etc.) to take advantage of differences in T1, T2, and/or diffusivity in combination.

Depth Sensitivity Profile and Tissue Fraction Estimation, Improving Muscle Measurement Localization The MR signal originating from the more distal muscle tissue is most relevant to the diagnosis of fluid disorders. Accordingly, in preferred embodiments, the present portable MR sensors are configured to provide the optimal measurement which selects an RF excitation frequency that sufficiently localizes the measurements towards the muscle tissue without unnecessarily sacrificing sensitivity. In some embodiments, the optimal choice of RF excitation frequency is informed by the local variation in subcutaneous thickness where regions with increased thickness will require a decreased frequency to achieve sufficient measurement penetration.

Sensor sensitivity as a function of depth can be used for precise estimation of the thickness of the subcutaneous tissue. The muscle fractions generated by integrating the sensitivity profiles for a candidate thickness can be compared with muscle fractions from experimentally acquired signals.

An algorithm to perform acquisition at the optimal RF excitation frequency could be implemented by utilizing this method. The optimal RF excitation frequency would be sufficiently low as to ensure a significant fraction of the sensitive region is located within the target tissue without being so low as to unnecessarily sacrifice sensitivity. This optimal frequency would be dependent on the subcutaneous tissue thickness, geometry of the portable MR sensor, and pulse parameters (e.g. excitation pulse bandwidth). Estimation of the optimal RF excitation frequency is made more robust and accurate by performing measurements of a tissue geometry at multiple RF excitation frequencies.

Figure 17:
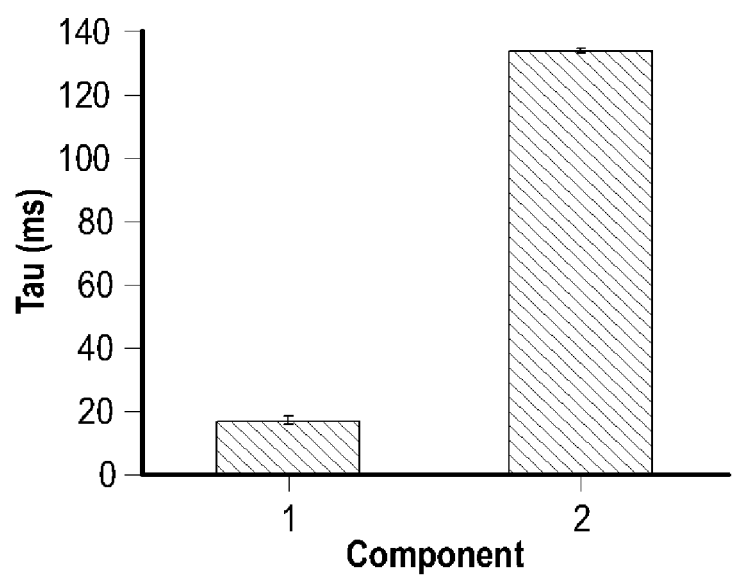
FIG. 17 is a graph showing a biexponential fit of CPMG signal of soybean oil acquired on portable MR sensor produces two distinct relaxation times. Error bars represent 95% confidence intervals on relaxation time estimates.
Figure 18A:
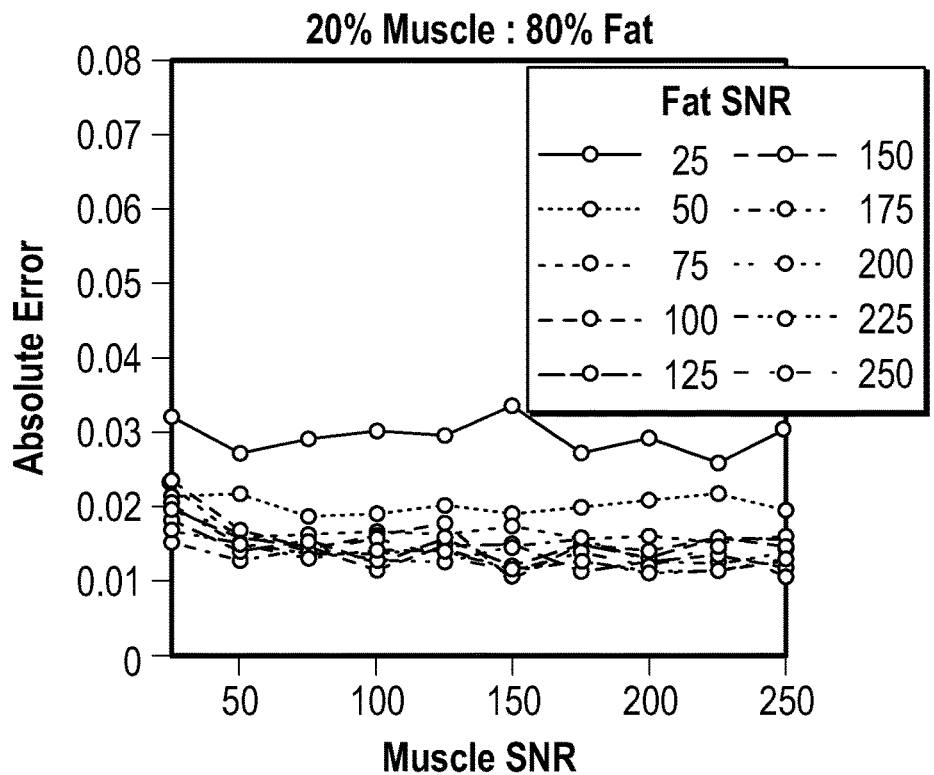
FIGS. 18A-F are graphs showing simulation of error in estimating muscle and fat fractions versus signal SNR. Simulations were performed at three muscle to fat ratios: 20:80 (FIGS. 18A-18B), 50:50 (FIGS. 18C-18D), and 80:20 (FIGS. 18E-18F).
Figure 18B:
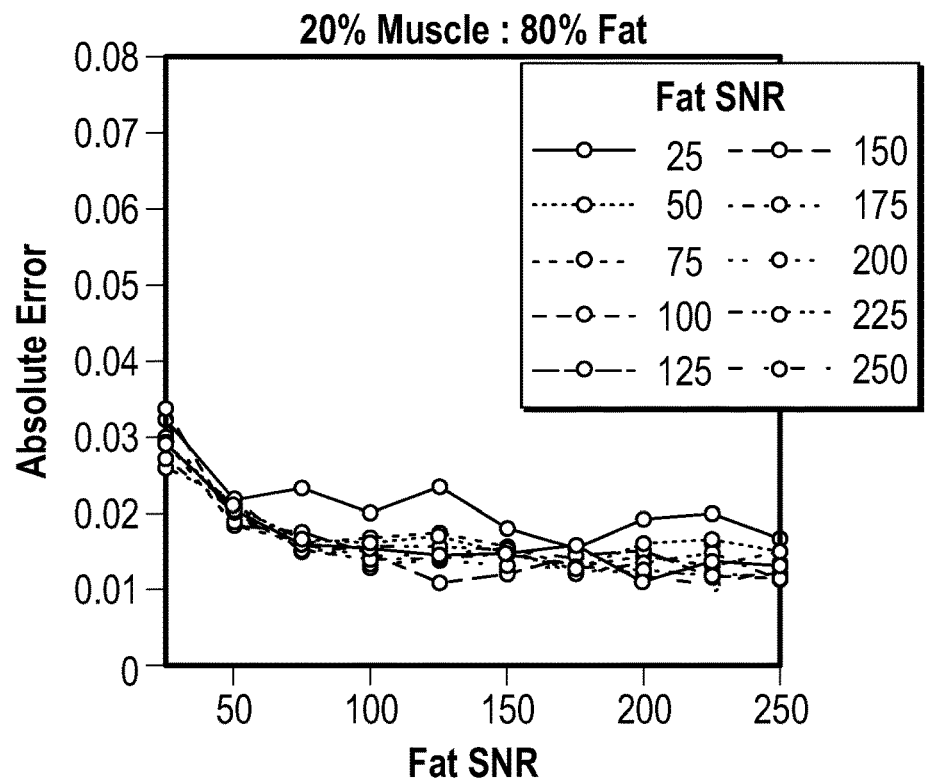
Figure 18C:
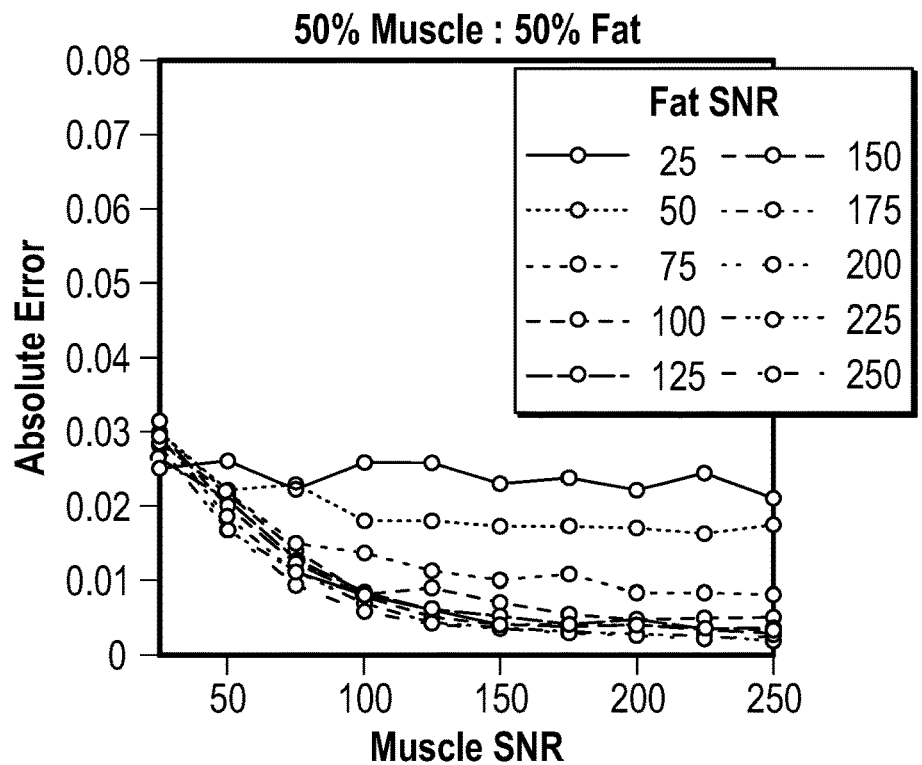
Figure 18D:
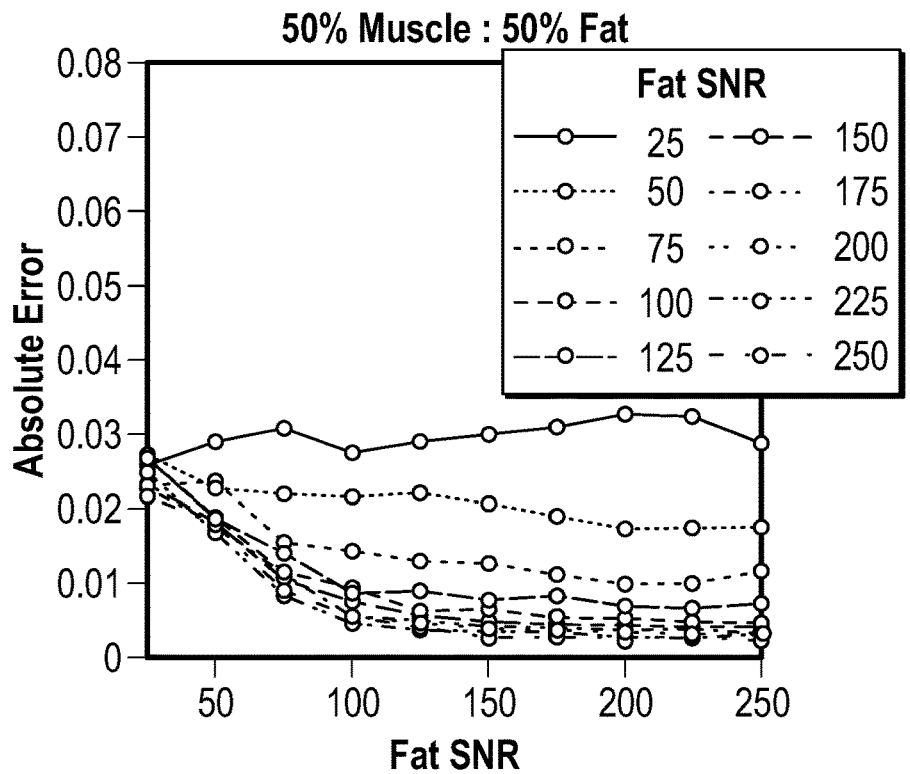
Figure 18E:
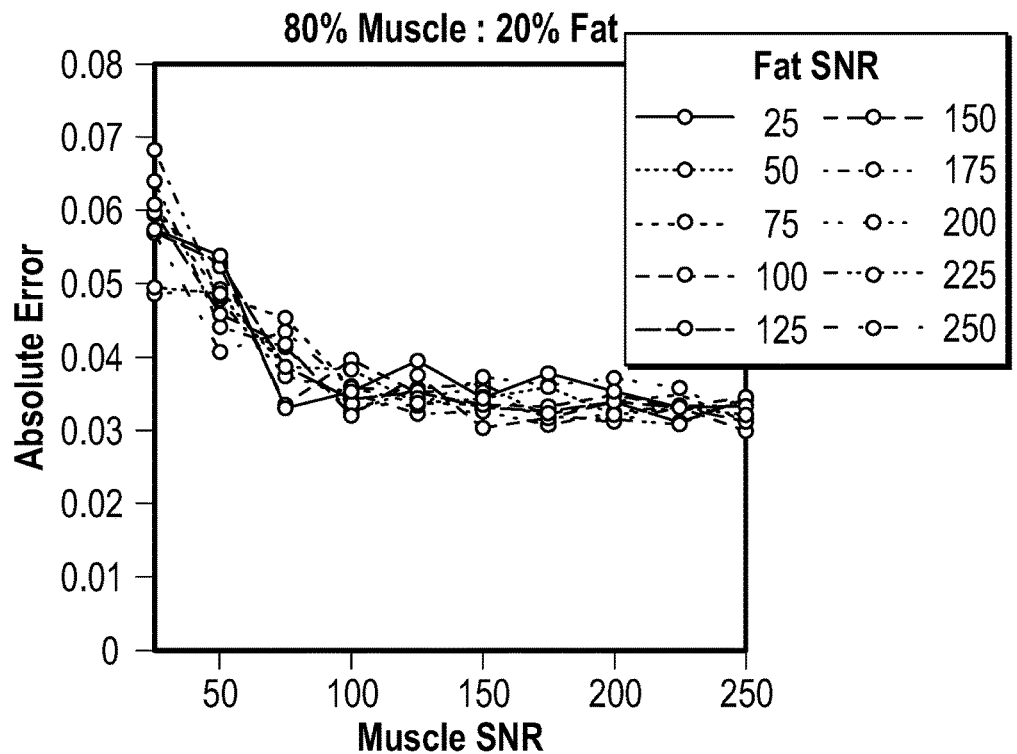
Figure 18F:
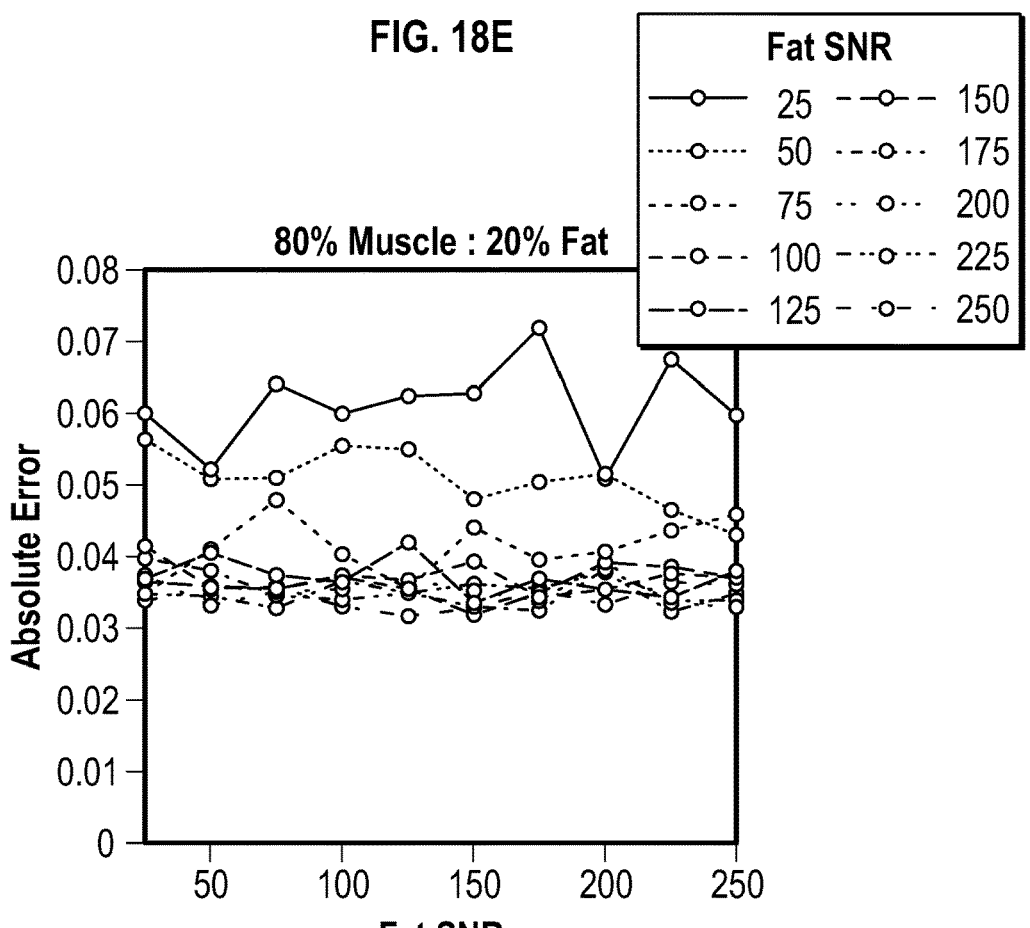

In some embodiments, a scan would first be performed based on an initial guess of the subcutaneous tissue thickness. The measurement would proceed until a signal of sufficient quality (e.g. SNR) to accurately estimate muscle fraction is acquired (FIG. 17). If the muscle fraction is too low, then the RF excitation frequency would be decreased to increase penetration depth. If the muscle fraction is very high, then the RF excitation frequency would be increased to increase sensitivity. After a few measurements, the subcutaneous tissue thickness can be precisely estimated (FIGS. 3B-3C), the appropriate RF excitation frequency selected based on sample geometry (FIG. 1C), and the measurement of interest performed. Performing these measurements at multiple RF excitation frequencies improves the robustness and accuracy of these estimates across a range of subcutaneous tissue thicknesses.

The robustness of this approach may be improved by first mapping the sensitivity profile of the sensor using multiple unique pulse sequences (e.g., varying pulse length, pulse duration, or pulse shape) in addition to RF excitation frequency and then identifying tissue thickness such that the tissue fraction error is minimized across all acquired measurements spanning various RF excitation frequencies and pulse sequences. This technique may be coupled with other measurement techniques, such as ultrasound or optical techniques, to assist in providing an initial guess for the subcutaneous tissue thickness. Additionally, anatomical information, both unique to the subject and to the measurement site, can be incorporated to provide for a more accurate initial guess of the subcutaneous tissue thickness.

The efficiency of this algorithm may be improved by performing each CPMG (Carr-Purcell-Meiboom-Gill) scan at a unique RF excitation frequency rather than accumulating sufficient signal to accurately identify the muscle fraction. A modified version of this algorithm could iteratively estimate the subcutaneous tissue thickness after each scan, then identify the optimal RF excitation frequency for the next scan in order to maximally improve its estimate. This approach may rely on MR dictionary-based approaches spanning a wide range of parameters (e.g., RF excitation frequency, other pulse parameters, subcutaneous tissue thickness, a range of subcutaneous relaxation times/amplitudes, and a range of muscle relaxation times/amplitudes) to improve the accuracy of subcutaneous tissue thickness estimates. The range of subcutaneous and muscle relaxation times/amplitudes may be learned from measurements on ex vivo tissue from animals, ex vivo tissue from humans, in vivo measurements on a population of humans, or in vivo measurements from a particular subject on which additional measurements are performed.

Varying Echo Time Enables Sensitivity Towards Sample Diffusivity

Manipulating the echo time within CPMG allows control over the effect of diffusivity on the relaxation properties of the signal with our portable MR sensor. That is, by controlling the echo time, the relative signal attenuation due to T2 decay and the motion of spins within the magnetic field can be varied.

Increased echo time leads to a decrease in relaxation time. The magnitude of this decrease is more pronounced with increased sample diffusivity. The change in decay rate of each signal is dependent on echo time. The relatively high static magnetic field inhomogeneity, a characteristic of most single-sided MR sensors, enables strong diffusion weighting to be achieved with relatively short echo times. The dependency of relaxation time on both echo time and sample diffusivity can be used to identify the T2 and diffusivity of a sample.

Another pulse sequence to enable a measurement of both sample diffusivity and T2 would only vary the spacing between the first the first and second pulse (excitation and inversion) of a traditional spin echo train sequence, while leaving the spacing between all subsequent inversion pulses constant. This would allow changes in the amount of signal attenuation in the first echo, due to changes in echo time, to primarily indicate diffusivity. The signal after the second inversion pulse would be used to measure relaxation properties (e.g., T2) and improve the sensitivity of the measurement.

This approach may be combined with previously described methods of achieving spatial localization to perform diffusion-weighted measurements with spatial targeting within a sample. Furthermore, the sensitivity of the signal towards sample diffusivity will be a function of position and pulse sequence. Multiple measurements with pulse sequences with different degrees of diffusion-weighting could be performed to recover local variations in sample diffusivity.

Methods of Use

The portable MR sensor can identify changes in intramuscular fluid distribution despite the presence of a confounding signal from proximal subcutaneous tissue. This is achieved by localizing the signal via tuning of the RF excitation frequency and by isolating the muscle signal via diffusion-weighted measurements and T2 multicomponent relaxometry.

The portable MR sensor can identify the progression of fluid accumulation in the intramuscular ECF. In cases of moderate subcutaneous tissue thickness, the increased penetration depth offered by varying the RF excitation frequency serves to localize the measurement completely within the muscle tissue. In circumstances where the subcutaneous thickness is more substantial and localization by tuning the RF excitation frequency is insufficient, a diffusion-weighted measurement can help identify changes in the signal that are associated with fluid shifts within the intramuscular ECF. The combination of diffusion-weighted, depth-resolved multicomponent T2 relaxometry with a single-sided MR sensor offers the unique ability to identify shifts in tissue fluid distribution despite the presence of confounding tissue layers.

The techniques described here to utilize variation in compartment diffusivity to enhance a shift from baseline could be generalized to situation where one pulse sequence provides a signal that allows discrimination of multiple fluid compartments that are otherwise similar in relaxation properties (e.g., muscle ECF and subcutaneous tissue).

The combination of depth-resolved, diffusion-weighted multicomponent T2 relaxometry can enable a portable, single-sided MR sensor to measure disruptions in intramuscular fluid distribution. These techniques can be applied to provide a non-invasive measure of fluid volume status in humans despite highly variable subcutaneous tissue thickness. This approach may ultimately serve as a real-time, point-of-care indicator of euvolemia and improve the management of end-stage renal disease patients during hemodialysis.

In some particular applications of the present devices and methods, the sensor device is adapted to assess fluid distribution in the patient in order to determine whether the patient is hypovolemic, euvolumic, or hypervolemic, and then to treat the patient, if necessary, e.g., by facilitating hydration or removal of excess fluids.

In the Examples detailed below, the model of acute muscle edema induced intramuscular ECF expansion. The techniques demonstrated there to measure localized edema can be applied to other disorders which manifest as intramuscular ECF imbalances, such as fluid overload and fluid depletion (dehydration). Fluid overload causes intramuscular ECF expansion as excess fluid shifts from the vasculature to the interstitial space. Similarly, fluid depletion in the form of dehydration leads to intramuscular ECF depletion as fluid shifts from the interstitial to the vascular space to maintain electrolyte and osmotic balance.

FIGS. 7-11 provide additional details describing the present sensors and methods.

Figure 7:
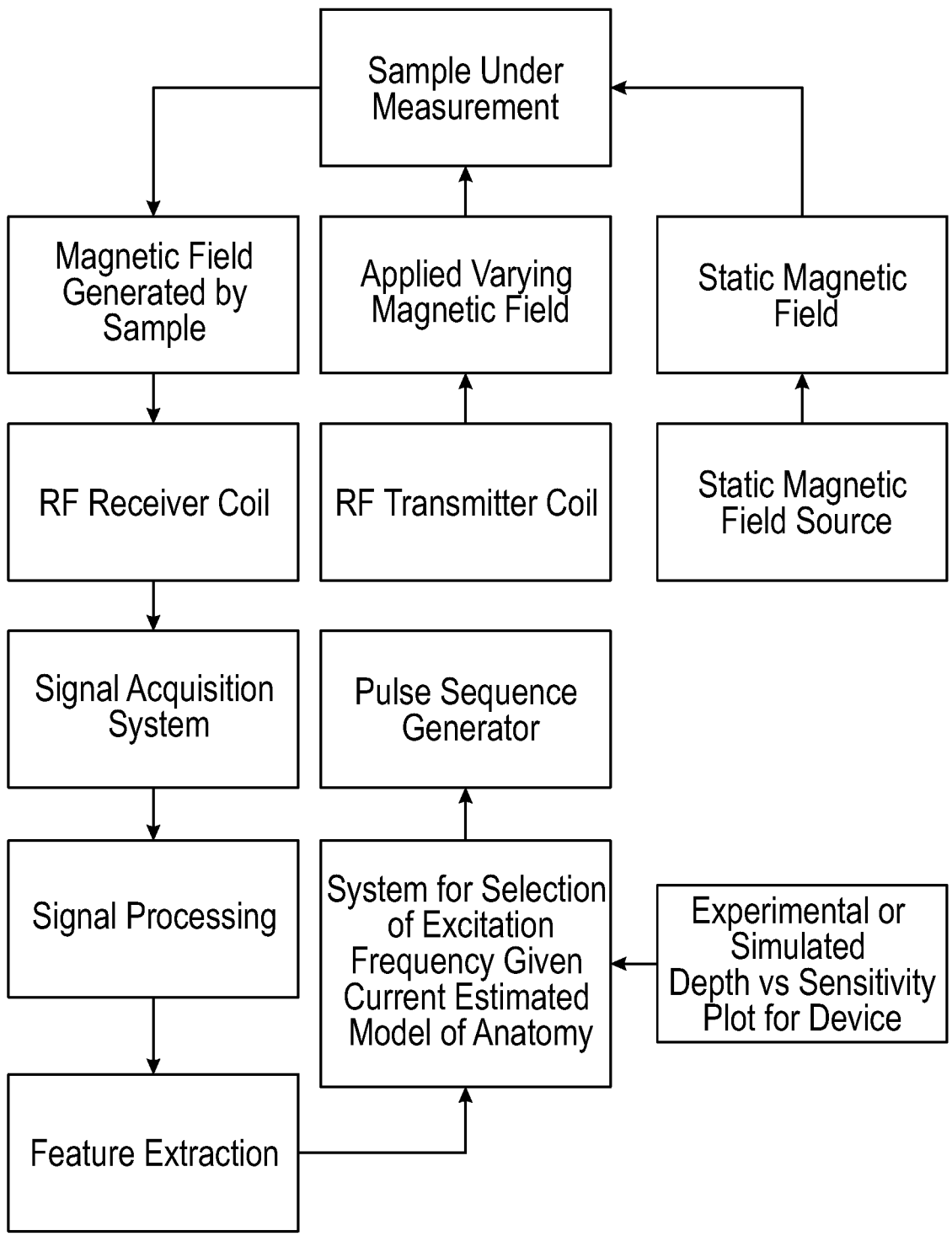
FIG. 7 is a flow chart of a process for real-time acquisition of depth profile, according to one embodiment.

FIG. 7 (depth profile for real-time acquisition) is a schematic for utilizing the data presented in FIGS. 1A-1D. Selecting the optimal excitation frequency in real-time will allow for faster acquisition of the signal of interest. Real-time selection of excitation frequency allows for selection of excitation frequency without human intervention by consideration of the current of the tissue under measurement. The block "Experimental or simulated depth vs sensitivity plot for device" is a more general description of the data presented in FIG. 1C. This data could also be acquired in simulation.

"Sample under measurement' refers to any part of the patient or sample being measuring. In some embodiments, as in the clinical study, this is the upper calf of a human patient. In other embodiments, it could be any part of the human body where the muscle tissue is easily accessible.

"Magnetic field generated by sample" means magnetic resonance relaxation of the sample following excitation induces a magnetic field that is measured by the RF receiver coil.

"Applied varying magnetic field" means the magnetic field produced by the RF transmitter coil to excite the sample under measurement.

"Static magnetic field" refers to the constant magnetic field created by either a permanent magnet geometry or a superconducting material. It polarizes the spins within the sample.

"Static magnetic field source" refers to the source of the static magnetic field, which is either a permanent magnet geometry or a superconducting material.

"RF transmitter coil" can be separate from or combined with an RF receiver coil and is responsible for applying a time varying magnetic field to excite the sample under measurement. There could be one or more of these coils.

"RF receiver coil" can be separate from or combined with an RF transmitter coil and responsible for measuring relaxation of the sample following excitation. There could be one or more of these coils.

"Signal acquisition system" refers to any system that digitizes the analog output of the RF receiver coil.

"Signal processing" refers to all processing of digital signal output by signal acquisition system. This includes but is not limited to averaging, denoising, and signal modulation.

"Feature extraction" refers to any fitting or modeling of the processed signal. Extraction of the relevant parameters of the fitting.

"Pulse sequence generator" controls the RF transmitter coil. It outputs a pulse sequence that is translated into an applied time-varying magnetic field created by the RF transmitter coil.

Figure 8:
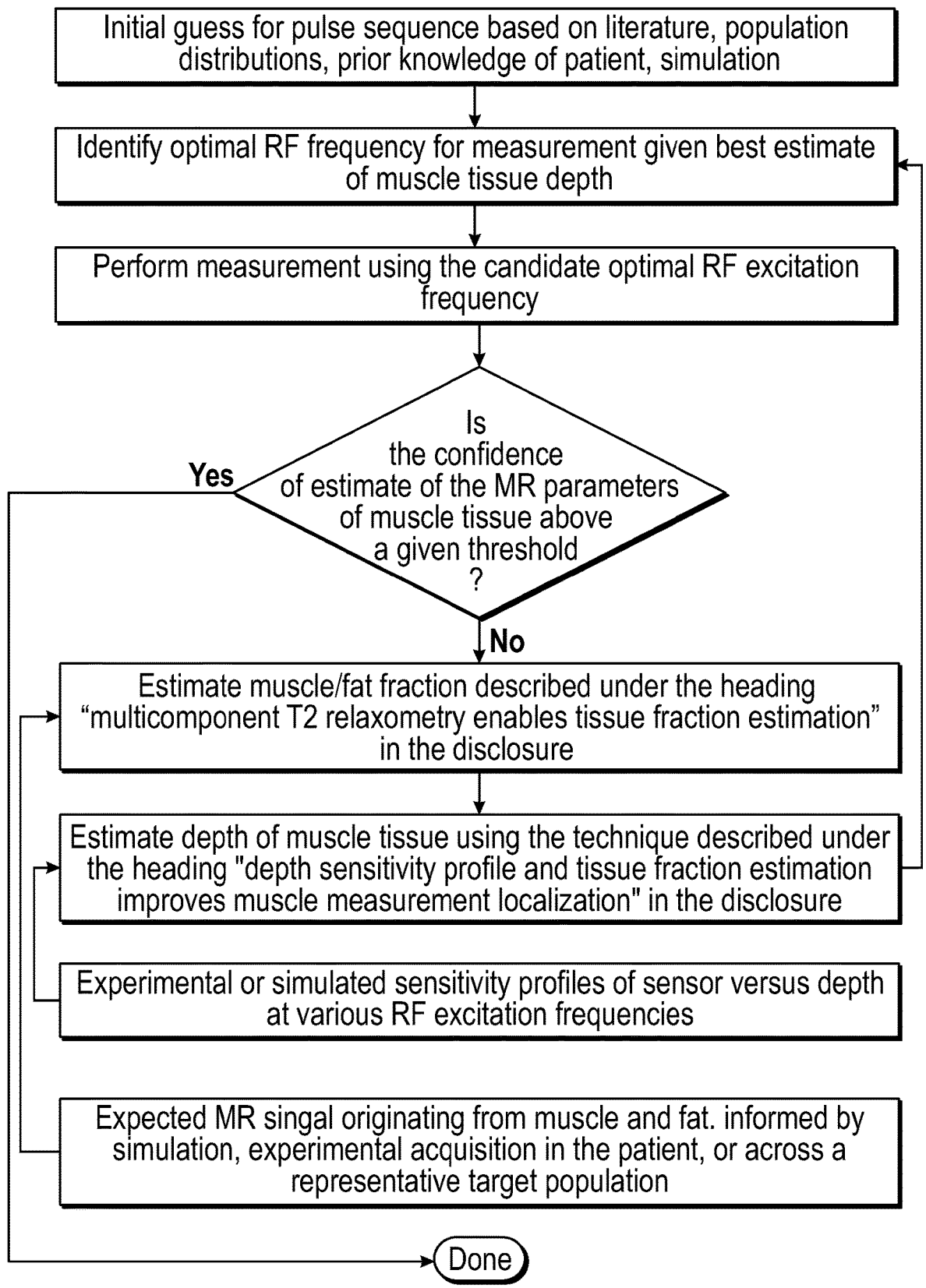
FIG. 8 is a flow chart of a process and system for selection of excitation frequency given current estimated model of anatomy, according to one embodiment.

FIG. 8 is a schematic diagram describing one embodiment of the "system for selection of excitation frequency given current estimated model of anatomy", for example from FIG. 7. It represents an iterative driven system which seeks to perform a highly accurate measurement of the MR parameters of muscle tissue. The system first starts with an initial guess for the sample anatomy and MR parameters (e.g. T2, T1, diffusivity, proton density). The system then identifies an excitation frequency (possibly at RF, but more generally at any frequency capable of polarizing a sample sufficiently to produce an MR signal). This frequency is selected based on the best estimate of the anatomy/tissue MR parameters. A measurement is then performed with this excitation frequency. If the resulting signal produces a highly accurate, confident estimate of the muscle tissue, then the system terminates. Otherwise the muscle/fat fraction is estimated using the disclosed algorithm, wherein information on the MR signal generated by muscle, fat, and other tissue is included. This information can be derived from simulation, experiment, and/or a combination these. The experiments may be performed in ex vivo tissue, in vivo in animals, in a representative set of human subjects, in the particular patient who is being measured at the current time, or in that case patient but at a previous time. An estimate of the depth of the muscle tissue is then made based on this estimate of the muscle/fat fraction and the known depth profile of the sensor. This estimate of the anatomy of the subject or sample is then passed back to the starting point and used to continue this optimization process until a suitable high accuracy signal is measured. The signals from prior measurements can be combined with the signal from the most recent measurements to provide a more accurate estimate of the MR parameters of the sample.

Figure 9:
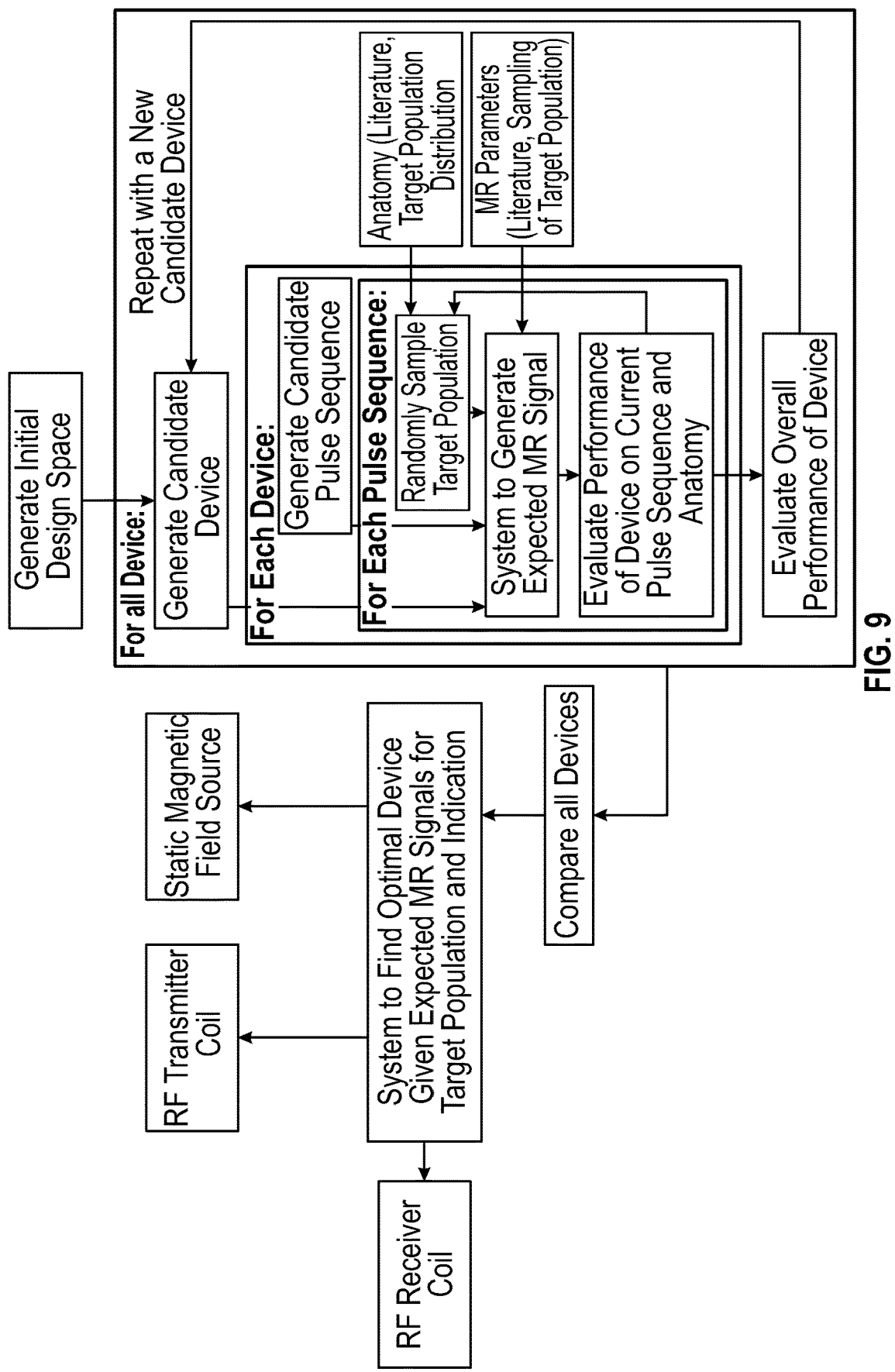
FIG. 9 is a flow chart illustrating a process for implementation of manuscript innovations for device design, according to one embodiment.

FIG. 9 is a schematic showing one embodiment in which the present systems and methods can used to design an MR device configured to assess intramuscular fluid distribution as described herein.

"Generate initial design space" refers to limiting the design space to include only potentially useful devices given assumptions about human physiology. These assumptions will limit the possibly useful outputs of the design pipeline (static magnetic field, RF transmit profile, and RF receive profile).

"Generate candidate pulse sequences" relates to the present description in which candidate pulse sequences are configured to take advantage of depth resolution and diffusion weighting. It could also involve tuning of any of the pulse sequence parameters described with reference to FIG. 11.

"Evaluate overall performance of device"—Multicomponent T2 relaxometry is one way to evaluate the performance of a candidate device by comparing the fitting results to what is expected given the current setup (device, pulse sequence, anatomy).

"Anatomy (literature, target population distribution)"—A target population may be chosen by first selecting a particular indication. Models of the appropriate anatomy are developed from literature and relevant distributions of target population characteristics.

"MR parameters (literature, sampling of target population)"—The MR parameters able to predict disease states of the target population are found in literature and/or from measuring a sample of the target population.

"System to generate expected MR signal block"—This will take into account all sources of variability for MR parameters of tissue, including volume status (i.e. volume overloaded, euhydrated, dehydrated). It will use a Bloch simulation to accurately model the expected MR signal given a device, pulse sequence, and sample.

Figure 10:
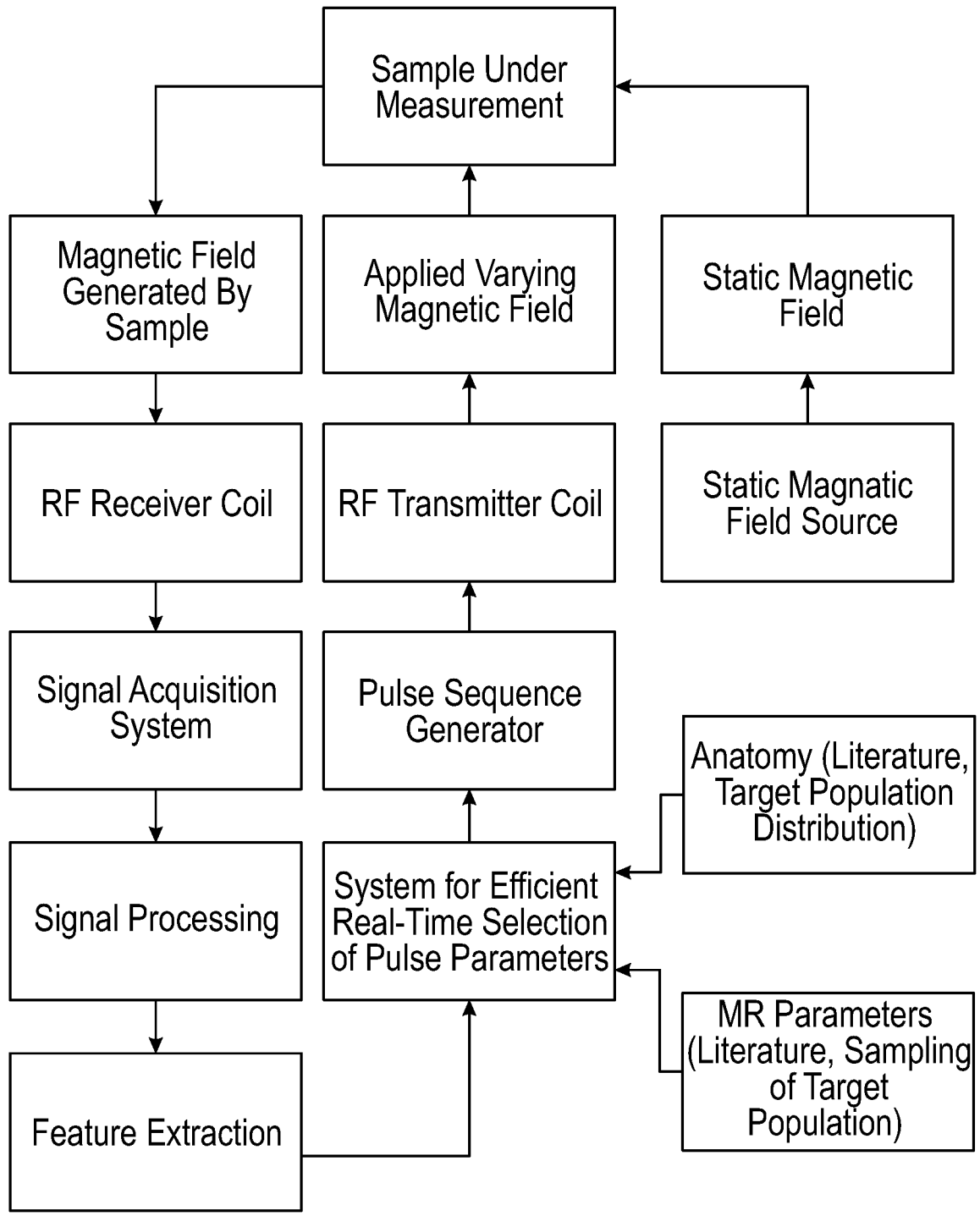
FIG. 10 is a flow chart illustrating the use of device response to all possible pulse sequence parameter and sample combinations to inform real-time acquisition, according to one embodiment.

FIG. 10 shows a more general framework for varying all pulse sequence parameters in real-time. Rather than only adjusting excitation frequency, several parameters can be varied to decrease acquisition time and increase confidence and accuracy of MR parameters of interest. After each scan, all information currently known about the MR parameters of the sample and target population is used to pick the pulse sequence parameters for the next scan. Pulse parameters may therefore be chosen without human intervention.

Pulse sequence parameters that can be tuned include, but are not limited to, RF excitation frequency, RF excitation bandwidth, pulse duration, pulse amplitude, pulse phase, pulse shape, pulse spacing (uniform and non-uniform), variability between pulses, and parallel pulses emitted by multiple transmit coils.

Figure 11:
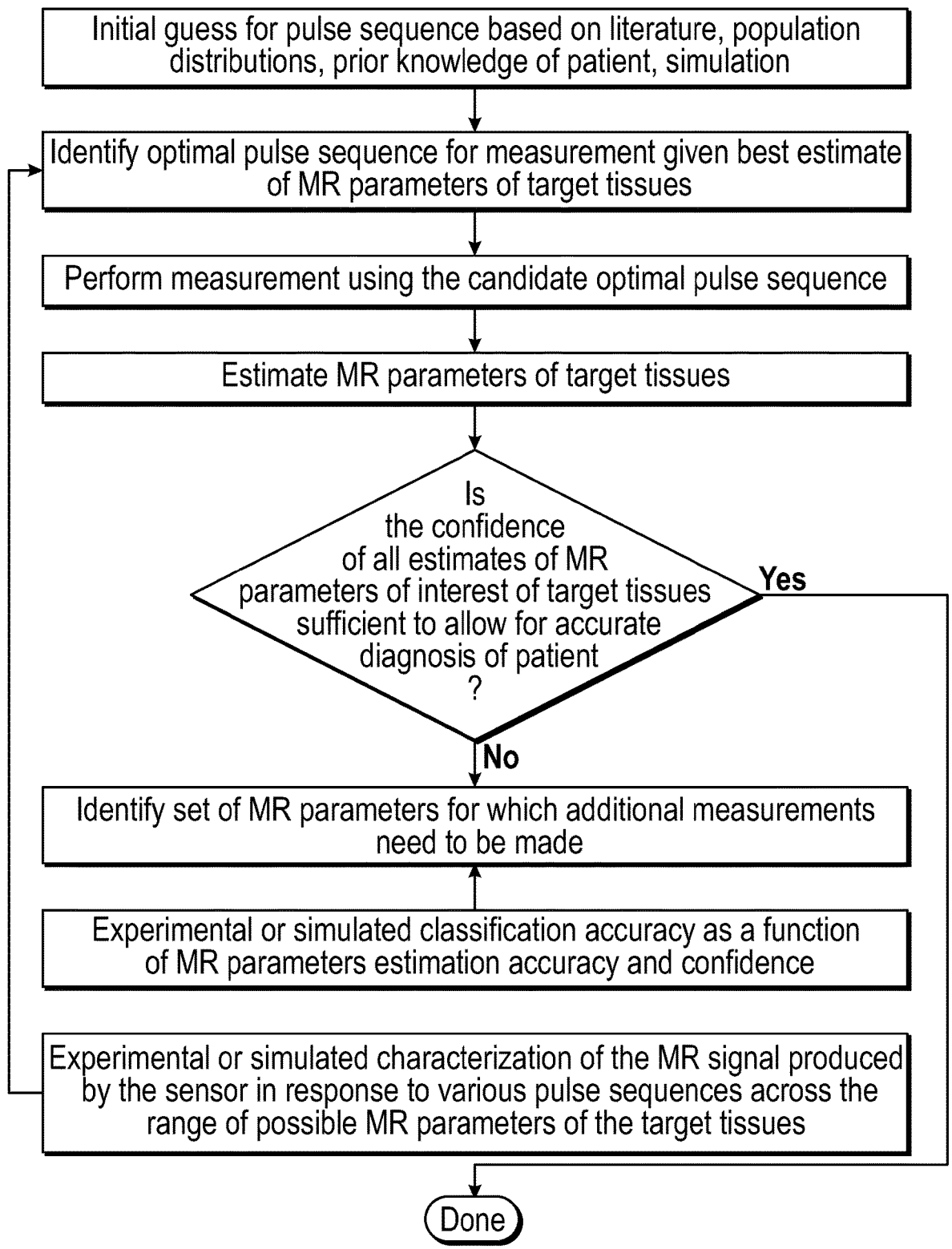
FIG. 11 is a flow chart illustrating a method and system for efficient real-time selection of pulse parameters, according to one embodiment.

FIG. 11 illustrates one embodiment of a system for selection of pulse parameters, for example from FIG. 10. The spirit of this diagram is similar to the diagram entitled "System for selection of excitation frequency given current estimated model of anatomy". This diagram is more general though as it explains a strategy to optimize over the entire pulse sequence in order to estimate all possible MR parameters of interest and/or directly estimate the diagnosis of interest. Target tissues includes but is not limited to hair, skin, bone, subcutaneous fat, intramuscular fat, muscle, vital organs, connective tissue, vasculature, blood, visceral fat, pleural spaces, intraperitoneal space, and any other well-defined organs or tissues. This could include any combination of these tissues and organs. In some preferred embodiments, the systems and devices are configured for measurement of the skeletal muscle, although other applications may rely on a measurement of other tissues/organs.

New Acquisition Strategies

In some embodiments, the MR sensors, including operating systems therefor, are adapted to apply new acquisition strategies to more efficiently and specifically identify the distribution of fluid within the muscle compartment. In some particular embodiments, the ultimate goal of the sensor system is to perform a measurement of the distribution of fluid within the muscle compartment in order to detect systemic fluid imbalances. In some embodiments, the sensor systems focus on multicomponent T2 relaxometry, because it provides a tractable design goal for an MR system, is straightforward to relate to physical changes in fluid distribution, and is amenable to efficient MR acquisition strategies. In some other embodiments, the sensor systems may use both traditional pulse sequences outside of CPMG as well as other approaches based on compressed sensing, dictionary-based approaches, and adaptive acquisition strategies.

For example, additional parameters of interest for new acquisition strategies include T1, proton density, diffusivity, and magnetization transfer. Although there are well established pulse sequences available to interrogate these properties with single sided MR systems, they need to be adapted to provide suitable acquisition times and sensitivity in the muscle tissue.

Multidimensional NMR, for example, may be used to establish/characterize a relationship between two or more of these MR parameters. This increased specificity towards fluid compartments could allow for improved characterization of each of their distinct MR properties; however, these multidimensional NMR techniques should be adapted to provide clinically useful acquisition times. For example, there are some known approaches in magnetic resonance that rely upon sparsely sampling parameter space and highly regularized reconstruction, which may provide highly accelerated multidimensional measurements. These techniques rely on the fact that the signal generated by a magnetic resonance sensor redundantly represents data when transformed into particular domains or bases.

In some embodiments, a dictionary-based approach may be used with a single sided portable MR sensor to identify fluid imbalances. First, a dictionary would be created which represents the expected signal produced by a sample at various fluid volume states when interrogated with a particular pulse sequence by an MR sensor. This dictionary would rely on knowledge of the geometry of the sensor and the expected MR parameters of the tissue as a function of fluid volume status. The particular pulse sequence could be generated by a random process or could be designed to extract maximal information from the sample. The sensor would then be used to perform the measurement of the sample using that particular pulse sequence. The signal that is acquired would be compared to the simulated signals within the dictionary. The simulated signal from the dictionary that matches the acquired signal would correspond to the best approximation of the MR parameters and/or fluid volume status of the tissue. This process could be regularized so that many signals originating from highly similar fluid volume states within the dictionary must be close matches to the acquired signal. This technique could be extended to include multiple pulse sequences. This technique may be applied iteratively or adaptively so that early measurements provide a coarse approximation of the MR parameters and/or fluid status of the tissue, while later measurements provide a finer approximation (see FIG. 11). This may result in a more robust or more efficient acquisition strategy.

In reference to an adaptive strategy as described in FIGS. 8 and 11, an acquisition process may be implemented that utilizes machine learning (e.g., reinforcement learning) in order to select the best set of acquisition parameters. This system would first be trained—using both simulation and experimental methods—to identify the optimal series of pulse sequences (known as a policy) in order to most quickly and accurately satisfy the criteria outlined in FIGS. 8 and 11. These criteria can include estimating the MR parameters of muscle tissue with confidence beyond a particular threshold or estimating the MR parameters of interest sufficiently well in order to provide a diagnosis. When deployed on an unknown sample, this trained system would then iteratively perform measurements, analyze the measurements, and then select the next set of pulse sequence parameters based on the learned policy from the training process.

The devices and methods described herein will be further understood by reference to the following non-limiting examples.

Example 1

The objective of this study was to demonstrate the utility of novel single sided MR approaches towards identifying shifts in intramuscular fluid distribution. First, the ability of a portable MR sensor was characterized to identify tissue fractions in a heterogeneous sample using multicomponent T2 relaxometry. Next, its ability to resolve spatially distinct regions by varying the RF excitation frequency was demonstrated and characterized. It was then shown that these techniques can be combined to identify tissue layer geometry and localize the measurement towards the muscle tissue. Sensitivity towards differences in sample diffusivity was demonstrated without the use of a switchable gradient. Finally, the combination of all of these techniques was demonstrated in an in vivo rodent model of muscle edema.

A model of acute, local inflammatory muscle edema in a rat was used to investigate fluid shifts within muscle expected in patients experiencing volume overload. An intramuscular λ-carrageenan injection is known to induce inflammation followed by subsequent hyperemia and edema. This leads to expansion of the interstitial space within the muscle due to an influx of free fluid. We validated this model by observing an increase in relaxation time within the muscle with T2-weighted MRI.

All sample sizes and data analysis methods were prospectively determined. Sample sizes were determined with power calculations based on effect sizes estimated from previous, similar experiments performed within our group. No outliers were excluded from data analysis. The investigators were blinded to the identity of each image when drawing regions of interest. Data collection with the portable MR sensor was stopped when a signal of sufficient quality was acquired. The endpoint for in vivo edema studies was prospectively determined from prior studies.

Animals

Animal studies were approved by the Massachusetts Institute of Technology (MIT) Institutional Animal Care and Use Committee (protocol number 0716-045-19), and animals were cared for in the U.S. Department of Agriculture-inspected MIT Animal Facility under federal, state, local, and National Institutes of Health guidelines for animal care. Male Sprague Dawley (Crl: 001) rats were purchased from Charles River Laboratories. Animals were provided ad libitum access to food and water for at least 72 hours prior to the start of experiments.

Multiexponential Fitting

CPMG T2 decay curves were modeled as multiexponential signals in order to extract relaxation times ($\tau_i$) and relative amplitudes ($A_i$). Echo integrals were computed as the sum of the points sampled for each echo during CPMG when more than one point was collected for each echo. A general multicomponent exponential decay signal was represented as:

$$\hat{y}(t, A, \tau) = \sum_{i=1}^{N} A_i * \exp(-t/\tau_i) \qquad (1)$$

where ŷ(t) is the estimated signal, N is the number of components, A is a vector of amplitudes, and τ is a vector of corresponding relaxation times. Two models were used to represent the multicomponent nature of these signals in this study. The first optimizes over both the relaxation times and relative amplitudes. The optimal set of parameters is found by minimizing the L2-norm of the residuals between the estimated and the measured signal:

$$A^{opt}, \tau^{opt} = \underset{A,\tau}{\mathrm{argmin}} \|y(t) - \hat{y}(t)\|_2 \quad (2)$$

where y(t) is the measured signal and $\|\cdot\|_2$ represents the L2-norm. This model allows discovery of the relaxation times and amplitudes of a multiexponential signal. The second model optimizes only over the amplitudes as the relaxation times are specified as parameters:

$$A^{opt} = \underset{A}{\mathrm{argmin}} \|y(t) - \hat{y}(t, \tau)\|_2 \quad (3)$$

This more constrained model allows the amplitudes to be estimated more accurately and differences between signals to be described solely as amplitude changes. Signal to noise ratio (SNR) was defined as the maximum magnitude value divided by the standard deviation of the noise. The noise distribution was estimated from the residuals of the fit.

Depth Sensitivity Characterization

A thin, planar sample was oriented parallel to the surface of the sensor and scanned along a line perpendicular to its surface. The sample consisted of a 380 μm×6 mm×6 mm pocket machined into PEEK (polyether ether ketone) stock filled with aqueous solution of a paramagnetic species ($CuSO_4$). PEEK was used as it produced a negligible MR signal. Measurements were performed with the center of the sample located between 0.690 mm and 6.59 mm from the surface of the sensor.

Measurements were performed with the CPMG pulse sequence with 2000 echoes, an echo time of 65 μs, a repetition time of 240 ms, a pulse duration of 12 μs, an acquisition bandwidth of 1 MHz (dwell time of 1 μs), and 16 acquired points per echo with a Kea2 spectrometer (Magritek, Wellington, New Zealand). The RF excitation frequency was varied across the following range (11.43, 11.49, 11.54, 11.6, 11.63, 11.66, 11.69, 11.72, 11.75, 11.78, 11.81, and 11.83 MHz) in order to identify changes in sensitivity as a function of RF excitation frequency. The amplitude in a triexponential fit (Eq. (3)) corresponding to the relaxation peak of the aqueous solution indicated the sensitivity of the sensor.

Portable MR Sensor Measurements of Ex Vivo Tissue

Tissue was extracted from a Sprague Dawley rat immediately after euthanasia via carbon dioxide inhalation. Muscle and fat tissue was excised from the lower hind limb. Tissue was gently blotted dry with a paper towel to remove excess moisture. Tissue samples were placed into sealed containers to avoid evaporation during MR measurements. In order to prepare the hybrid sample, fresh tissue samples were cut into small (~1 mm) pieces, weighed, combined into a heterogeneous mixture, and placed into a sealed container.

Portable MR sensor measurements were performed with the CPMG pulse sequence with 8192 echoes, an RF excitation frequency of 11.60 MHz, an echo time of 65 μs, a repetition time of 1517 ms, a pulse duration of 12 μs, an acquisition bandwidth of 1 MHz (dwell time of 1 μs), and 16 acquired points per echo with a Kea2 spectrometer (Magritek, Wellington, New Zealand).

The MR signal from each tissue was modeled as a triexponential signal (Eq. (2)) allowing the unique relaxation times and amplitudes of each tissue to be identified. The amplitude corresponding to the second peak was attributed to the aqueous solution within the planar phantom and used to estimate the relative sensitivity as a function of depth and RF excitation frequency.

Algorithm for Identification of Constituent Signal Fractions

We designed an algorithm that seeks to identify the tissue fractions (e.g. muscle and fat fractions) within the heterogeneous hybrid sample. A multiexponential fit (Eq. (2)) is performed on the hybrid signal to identify the relaxation times, τ, for the algorithm to utilize. A synthetic signal, $\hat{y}_{hy}$(t, f), is produced as a linear combination of the MR signals from constituent tissues at a specified ratio as shown in Eq. (4):

$$\hat{y}_{hy}(t, f_{mu}) = f_{mu} * y_{mu}(t) + (1 - f_{mu}) * y_{fa}(t) \quad (4)$$

where $f_{mu}$ indicates the fraction of the signal correspond to muscle, $y_{mu}(t)$ represents the acquired signal from pure muscle tissue, and $y_{fa}(t)$ represents the acquired signal from pure fat tissue. This signal is then fit (Eq. (3)) with the previously identified relaxation times to identify the amplitudes, $A_\tau^{pred}(f_{mu})$, corresponding to each relaxation time. Similarly, the amplitudes, $A_\tau^{meas}$, corresponding to the same relaxation times are found via a multiexponential fit (Eq. (3)) with the same previously identified relaxation times. The algorithm seeks to minimize the error between the amplitudes from the measured and synthetic by adjusting the ratio of constituent signals (i.e. pure muscle, pure fat) used to generate synthetic signal, as shown in Eq. (5):

$$f_{mu}^{opt} = \underset{f_{mu}}{\mathrm{argmin}} \|A_\tau^{pred}(f_{mu}) - A_\tau^{meas}\|_2 \quad (5)$$

The error is minimized through the use of an iterative gradient descent algorithm. This technique could be extended towards more than two constituent signals.

Synthetic Tissue Phantoms

Synthetic tissue phantoms were fabricated from PEEK film (0.005-inch thickness) and nylon annular rings with an inner diameter of 6 mm and thickness of 1, 1.3, 1.5, and 3 mm with a tolerance of 0.3 mm. Each nylon ring was first bonded to a disk of PEEK film of identical outer diameter. The resultant cylindrical cavity was filled with fluid mimicking the MR relaxation properties of subcutaneous fat (i.e., soybean oil, $CuSO_4$). Then a second disk of PEEK film was used to seal each phantom.

Portable MR sensor measurements were performed with the CPMG pulse sequence with the following parameters common to all scans: 8192 echoes, 1 dummy echo, an echo time of 65 μs, a measurement time of 1065 ms, a repetition time of 1517 ms, a pulse duration of 12 μs, an acquisition bandwidth of 1 MHz (dwell time of 1 μs), and 16 acquired points per echo. RF excitation frequencies of 11.43, 11.53, 11.58, 11.66, 11.73, and 11.83 MHz were acquired.

The muscle fraction, $f_{mu}^{meas}(B_1)$, was estimated at each RF excitation frequency, $B_1$, for each phantom thickness from these measured signals using the previously described algorithm (See above Algorithm for identification of constituent signal fractions). The relaxation times used for each tissue were derived from monoexponential fits on the synthetic subcutaneous and muscle tissue solutions used within the synthetic tissue phantoms. Muscle fraction, $f_{mu}^{pred}(B_1, z)$, was similarly derived from the depth sensitivity profile data, $A(B_1, z)$, for each RF excitation frequency given a guess of the phantom thickness, z, as shown in Eq. (6):

$$f_{mu}^{pred}(B_1, z) = \frac{\int_z^\infty A(B_1, z)dz}{\int_0^\infty A(B_1, z)dz} \quad (6)$$

The thickness of the synthetic fat layer, $z^{opt}$, was estimated by minimizing the error between the estimated muscle fraction derived from the measured data and the predicted muscle fraction derived from the depth sensitivity profile data, as shown in Eq. (7):

$$z^{opt} = \underset{z}{\operatorname{argmin}} \|f_{mu}^{meas}(B_1) - f_{mu}^{pred}(B_1, z)\|_2 \quad (7)$$

In Vitro Diffusion Experiments

Samples consisted of aqueous solutions of varying concentrations of gadolinium trichloride (Gd) and polyethylene glycol (PEG) (mw: 4000 g/mol). Four samples (A, B, C, and D) were prepared with 126, 57, 28.5, and 0.17 mM of PEG and 0.42, 0.5, 0.5, and 0.5 mM of Gd, respectively. The relaxation data from the benchtop NMR spectrometer were acquired via CPMG with 25000 echoes, an echo time of 100 µs, a repetition time of 60 seconds, an RF excitation frequency of 19.95 MHz, an excitation pulse duration of 1.9 µs, an inversion pulse duration of 3.8 µs, an acquisition bandwidth of 1 MHz (dwell time of 3 µs), and 1 acquired point per echo with a (minispec mq20, Bruker, USA). The diffusion NMR data was acquired from a Bruker Avance III HD 400 NMR spectrometer with a pulsed gradient spin echo pulse sequence. Estimation of diffusivity was performed with MestReNova v12.0.4 (Mestrelab Software S.L.). The data from the portable MR sensor were acquired with the CPMG pulse sequence with the following parameters all measurements: a measurement time of 1.065 sec, an RF excitation frequency of 11.66 MHz, a repetition time of 452 ms, a pulse duration of 12 µs, an acquisition bandwidth of 1 MHz (dwell time of 1 µs), and 16 acquired points per echo. Echo times of 206, 223, 260, 368, 520, 735, and 1040 µs were utilized. All relaxation times were extracted by fitting the decay curves with a monoexponential model (Eq. (2)).

Ex Vivo Tissue Diffusion Experiments

Tissues were extracted from a rat identically to as previous described. Each tissue was measured with the portable MR sensor with the CPMG pulse sequence with an RF excitation frequency of 11.60 MHz, a repetition time of 1517 ms, a measurement time of 1.065 sec, a pulse duration of 12 µs, an acquisition bandwidth of 1 MHz (dwell time of 1 µs), and 16 acquired points per echo. Echo times of 65, 103, 164, 260, and 520 µs were used in order to identify changes in estimated relaxation time as a function of echo time. First, the signals from each tissue across all echo times were summed and fit with a biexponential model (Eq. (2)) to identify average two component relaxation times for each tissue. Then for each tissue, each signal at each echo time was fit with a biexponential model (Eq. (3)) with the respective relaxation times corresponding to the tissue. This allowed differences between signals to be identified as changes in the relative amplitudes of the slow versus fast relaxation peaks.

Muscle Edema Model

Acute muscle edema was induced via an injection of 200 µL of 1% λ-carrageenan solution into the biceps femoris of the lower hind leg of a 400 g, male Sprague-Dawley rat. Injections were performed with a 26 gauge needle with the tip of the needle inserted perpendicularly and approximately 4 mm into the skin. The injection was performed at an approximate flow rate of 10 µL/sec. The needle was held in place for approximately 30 seconds before removing it from the leg to reduce backflow and bleeding. Rats were administered 1 mg/kg of Buprenorphine SR via thoracic subcutaneous injection immediately prior to injection to minimize discomfort. Rats were anesthetized with 2% isoflurane during the injection.

Identification of Muscle Edema

For H&E histology, biceps femoris muscle tissue was excised from a freshly euthanized rat and fixed in formalin for 24 hours at 4° C. and stored in 70% ethanol until paraffin-embedding, sectioning, and staining.

MRI scans were performed with a 7T/310/ASR (Agilent, formerly Varian) scanner with vnmrj software (version 3.2b), equipped with a 63 mm/108 mm quadrature birdcage coil. Rats were first anesthetized with 2% isoflurane, then oriented in a supine position, and maintained on 1-2% isoflurane throughout data collection. Warm air (37° C.) was delivered to maintain body temperature of animals. T2 weighted anatomical scans were performed with FSEMS (fast spin echo multi slice) with repetition time 2000 ms, echo time 20 ms, echo train length 4, kzero 2, 2 averages, 2 dummy scans, 256×256 acquisition matrix, 40×40 mm field of view, and 1 mm slice thickness. A series of spin echo images for T2 relaxometry were acquired with MEMS (multi echo multi slice) with TR 7600 ms, TE 10 ms, 151 echoes, 4 averages, 64×32×5 acquisition matrix, 40×40 mm field of view, and 1 mm slice thickness. Slice acquisition order was interleaved using standard two-pass interleaving. All images were acquired along the sagittal plane of the animal.

The MRI data are acquired as magnitude images; therefore, the noise distribution is best approximated as a Rician distribution. We transform the noise distribution of each multi-echo signal from Rician to Gaussian by iteratively estimating the variance of the noise, extracting an estimate of the contribution from noise to each echo, then mapping between the cumulative distribution functions of a Rician distribution to a Gaussian distribution. The noise variance is estimated iteratively until the absolute value of the median of the echo magnitude in the noise tail is minimized.

Identification of Muscle Edema Via Portable MR Sensor

Anesthetized (2% isoflurane) rats were placed on top of the portable MR sensor in a supine position. The lower leg was positioned on top of the RF coil and secured with tape to minimize motion during signal acquisition. A synthetic subcutaneous tissue phantom was located between the sensor and the rat leg. The phantom consisted of a 2 mm thick cylindrical volume of soybean oil enclosed in a thin PEEK housing. Four measurements were performed with the CPMG pulse sequence with following parameters common to all scans: a repetition time of 1517 ms, a measurement time of 1065 ms, a pulse duration of 12 µs, an acquisition bandwidth of 1 MHz (dwell time of 1 µs), and 16 acquired points per echo. The first, second, third and fourth scans were performed with an RF excitation frequency of 11.43 MHz, 11.60 MHz, 11.60 MHz, and 11.83 MHz, respectively. The first, second, and fourth scans were performed with an echo time of 65 µs, 8192 echoes, and 1 dummy echo. The third scan was performed with an echo time of 260 µs, 4096 echoes, and 0 dummy echoes. These four measurements were repeated at −4, 5, 17, 29, 45, 72, 93, and 117 hours relative to the time of injection for a total of eight time points.

The 11.43 MHz and 11.83 MHz signals at each time point were fit with a triexponential model (Eq. (3)) with the relaxation times set to that of muscle tissue. The slowest component was attributed to the extracellular fluid within the muscle tissue (FIG. 6D). The same two signals at each time point were then fit with a five component model (Eq. (3)) with the relaxation times set to that of both muscle tissue and subcutaneous tissue. The amplitudes of the two components corresponding to the subcutaneous tissue were summed and attributed to the subcutaneous tissue. The slowest remaining component was attributed to the extracellular fluid within the muscle tissue (FIG. 6E).

In order to estimate the degree of diffusion attenuation, $\Delta$, a baseline value, $A_{260\mu s}^{baseline}$, for muscle ECF fraction in the 11.60 MHz 260 µs signal is first established. The deviation from this baseline of the muscle ECF amplitude of the 11.60 MHz 260 µs signal, $A_{260\mu s}$, is used to establish an estimate of the signal attenuation due to increased diffusivity of the muscle ECF, as shown in Eq. (8):

$$\Delta = \frac{A_{260\mu s}^{baseline} - A_{260\mu s}}{A_{260\mu s}^{baseline}} \quad (8)$$

This estimate of increased diffusivity is used to enhance the muscle ECF amplitude from the 11.60 MHz 65 µs signal. The relative decrease in the signal is used to scale the muscle ECF amplitude of the 11.60 MHz 65 µs signal (FIG. 6F) to produce an adjusted estimate of the muscle ECF amplitude, $A_{65\mu s}^{adj}$, as shown in Eq. (9):

$$A_{65\mu s}^{adj} = A_{65\mu s} * (1+\Delta) \quad (9)$$

Simulation of Necessary Signal to Noise Ratio to Estimate Muscle Fraction

A simulation was performed to assess the signal to noise ratio necessary to accurately estimate the muscle and fat fractions from within a heterogeneous sample. Muscle to fat ratios of 20:80, 50:50, and 80:20 were considered. Signal to noise ratios of each constituent signal (i.e. muscle, fat) of 25, 50, 75, 100, 125, 150, 175, 200, 225, and 250 were considered for a total of 100 pairwise combinations of signal to noise ratios. For each pair of SNRs at each muscle to fat ratio, a synthetic muscle and fat signal at the corresponding SNR was generated based on the relaxation times and amplitudes observed in triexponential fits (Eq. (3)) of ex vivo measurements of isolated tissue. A resultant hybrid signal was created as the sum of these two signals. The muscle to fat ratio was estimated using the previously described algorithm (See above Algorithm for identification of constituent signal fractions). Error was computed as the absolute difference of this estimate from the true muscle to fat ratio. 120 trials were performed for each combination of SNRs and muscle to fat ratios.

Statistical Analysis

95% confidence intervals ($\alpha=0.05$) for all parameter estimates in multicomponent exponential fits were computed assuming an asymptotic normal distribution for each estimate. Statistical significance of the onset of edema was assessed by two sample, one-sided t-test between first and second time point (FIGS. 6D-6F). Statistical significance of the progression of edema was assessed by Spearman rank correlation coefficient across the first five time points (FIGS. 6D-6F). Statistical significance of the recovery of edema was assessed by two sample, one-sided t-test between the fifth and final time point (FIGS. 6D-6F).

Results

Tuning RF Excitation Frequency Enables Slice Selection

Figure 12A:
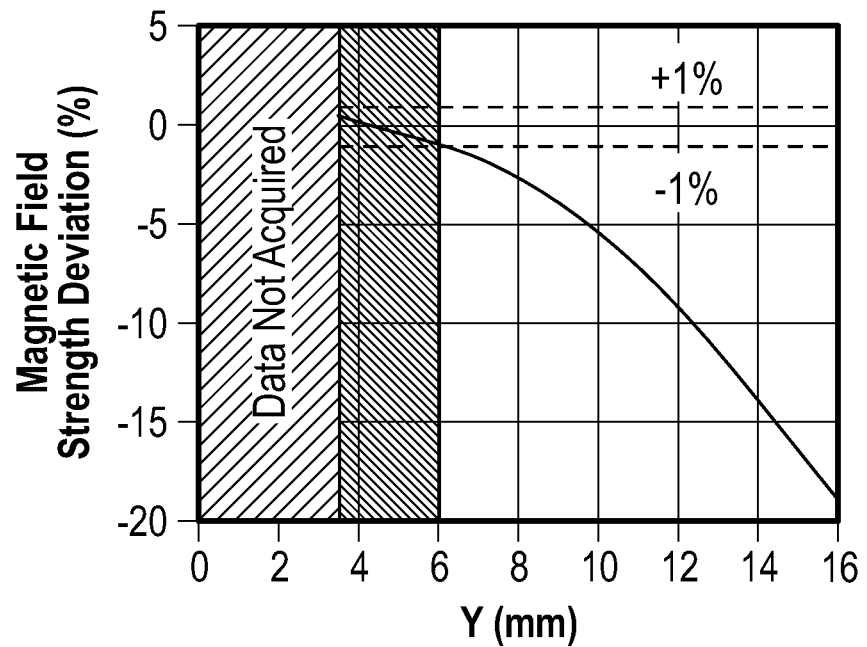
FIGS. 12A-12B are graphs illustrating a static magnetic field profile characterization of one embodiment of a portable MR sensor. Measured magnetic field strength deviation from B0 along the y-axis (FIG. 12A) and the z-axis (FIG. 12B) through the center of the uniform region. Shaded regions correspond to ±1% deviation from B0.
Figure 12B:
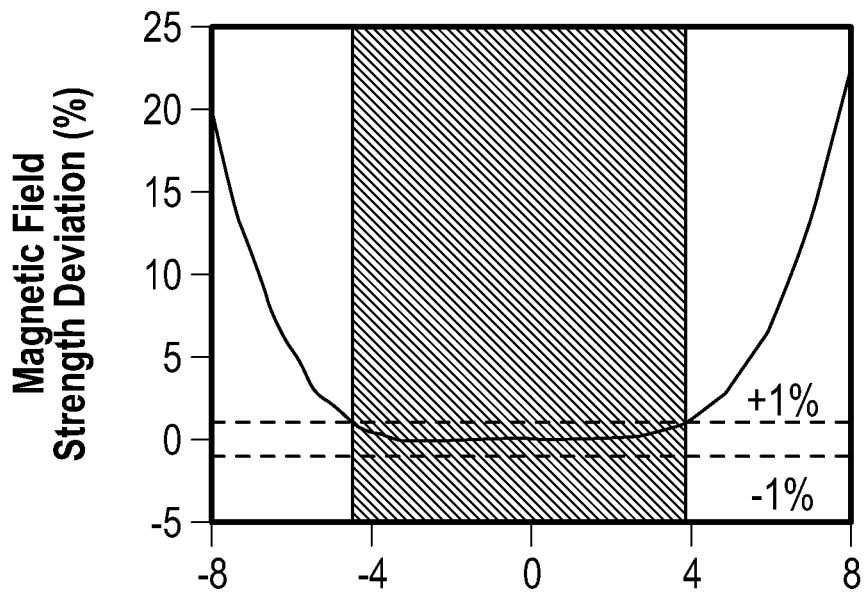

The measurement depth of single-sided MR sensors, including our sensor based on the Unilateral Linear Halbach magnet array, is limited due to the rapid decay of the static magnetic field strength away from the surface of the sensor (FIGS. 12A-12B). Our device was designed to perform a non-invasive scan of the skeletal muscle tissue within the lower leg of patients (FIG. 1A). These measurements are easily confounded by subcutaneous tissue despite selection of a measurement location with minimal subcutaneous thickness due to limitations in penetration depth. A measurement technique localized towards the muscle tissue would allow isolation of the muscle signal from nearby confounding tissues.

Figure 13A:
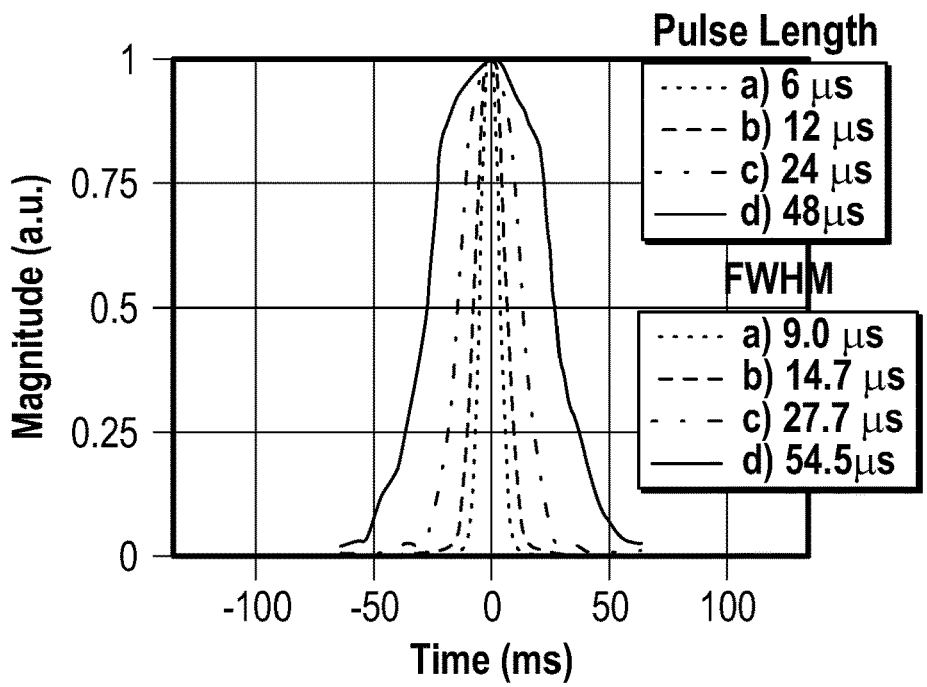
FIGS. 13A-13B are graphs illustrating spin echo duration and bandwidth versus pulse length, with time domain (FIG. 13A) and frequency domain (FIG. 13B) representations of spin echoes from portable MR sensor versus excitation and refocusing pulse length, according to one embodiment.
Figure 13B:
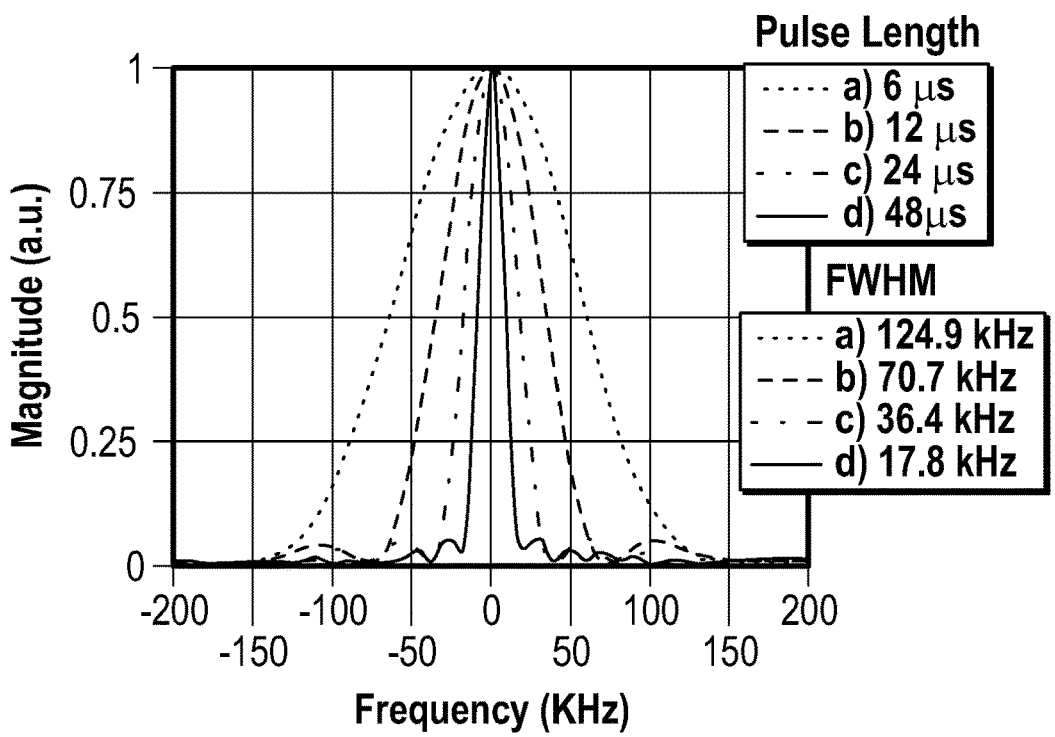
Figure 14A:
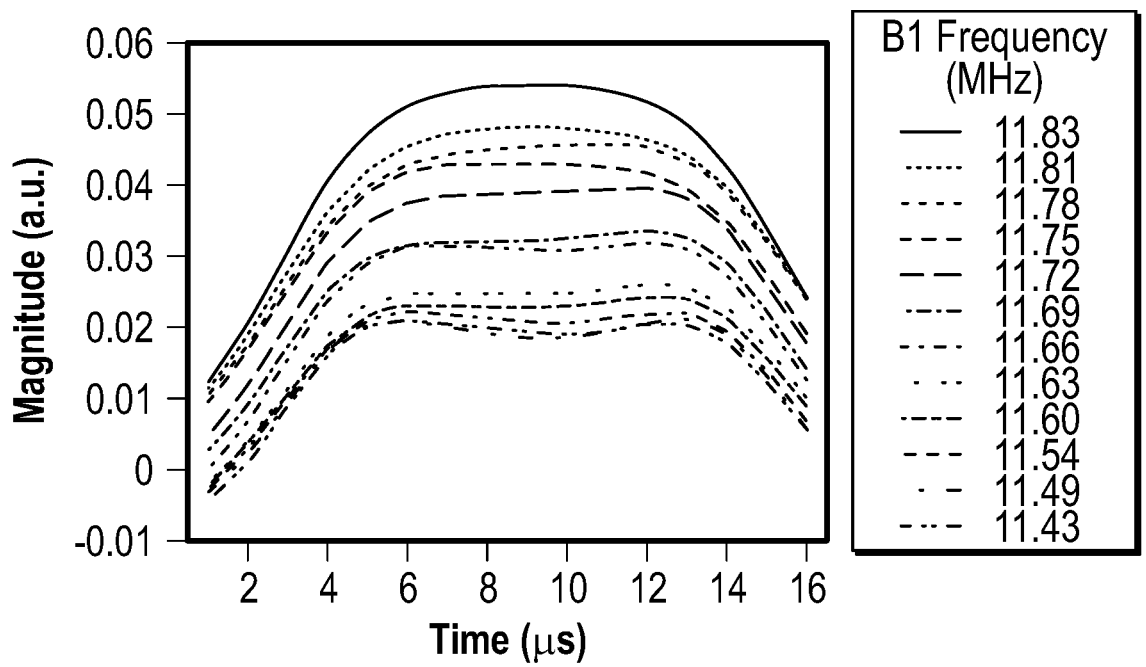
FIGS. 14A-14B are graphs illustrating spin echo duration versus RF excitation frequency, with spin echo amplitude versus time for varying B1 frequencies.
Figure 14B:
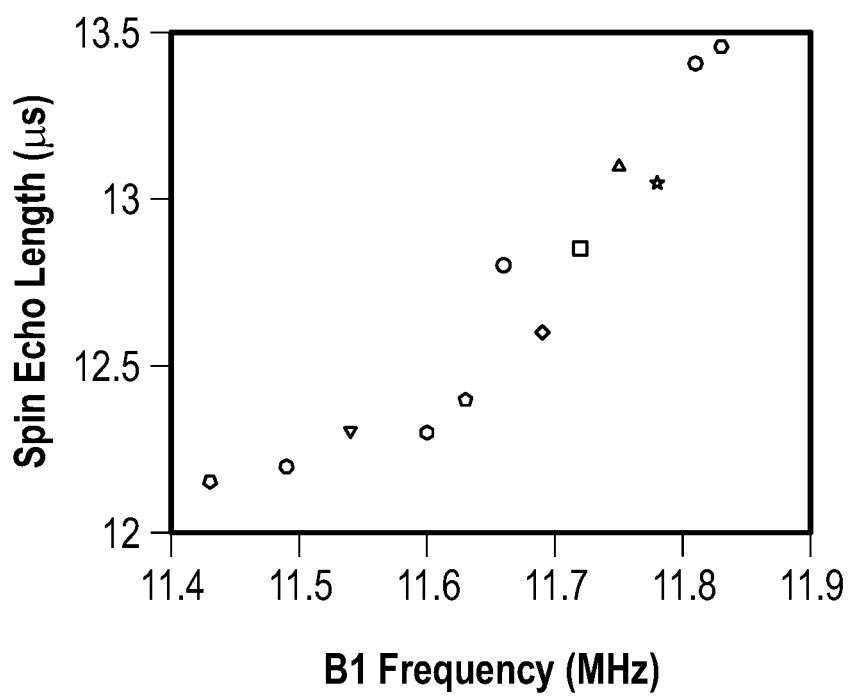

We showed that tuning the RF excitation frequency of the portable MR sensor allows for spatial selection of the position of the sensitive region. We demonstrated this by measuring the sensitivity of the sensor towards a thin, planar sample as a function of both distance from the sensitive region and RF excitation frequency ($B_1$) (FIG. 1B). A planar sample of an aqueous solution of a paramagnetic species ($CuSO_4$) with a thickness of 380 µm was scanned in front of the sensor. MR measurements via the CPMG pulse sequences were performed over a range of RF excitation frequencies for each depth of the sample. The sensitivity of the system was characterized as the relative signal strength produced by the sample at each depth position and RF excitation frequency. This sensitivity profile varied as a function of depth and exhibited a distinct region of peak sensitivity that is unique to each RF excitation frequency (FIG. 1C). The use of smaller RF excitation frequencies enabled localization of the measurement to regions located at a greater distance from the surface of the sensor. The effective slice thickness by a given RF excitation frequency decreased with distance from the sensor at a fixed excitation pulse bandwidth due to the increasing gradient of the static magnetic field (FIG. 1D). We showed that an RF pulse bandwidth of 0.7% excites slices 0.6 to 1.3 mm thick with slice thickness decreasing with depth. The thickness of the effective slice can be tuned by adjusting pulse parameters (e.g., RF excitation bandwidth, pulse duration (FIGS. 13A-13B), pulse shape, RF excitation frequency). A decrease in spin echo duration with decreasing RF excitation frequency indicated a decrease in T2-star due to increased field inhomogeneity with depth (FIGS. 14A-14B). The sensitivity decreased with increased depth due to increased attenuation of the RF field produced by the transceiver coil.

Tuning the RF excitation pulse frequency offers control over the fraction of proximal subcutaneous versus more distal muscle tissue in the acquired signal. This capability enables targeting of the measurement towards a tissue of interest.

Multicomponent T2 Relaxometry Enables Tissue Fraction Estimation

The presence of signals from multiple tissues, especially when each produces a distinct multicomponent T2 decay signal, can confound the analysis of a single tissue. Identifying the contribution from each tissue to the measurement allows isolation of each of their signals and further analysis of their relaxation properties.

Figure 2C:
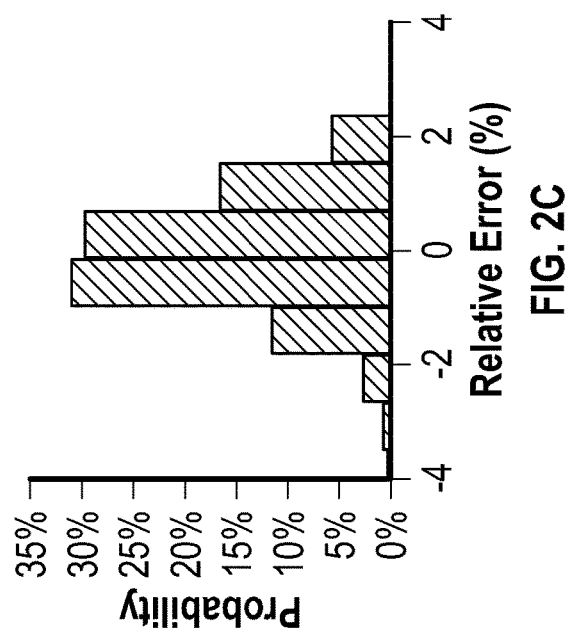
Figure 2B:
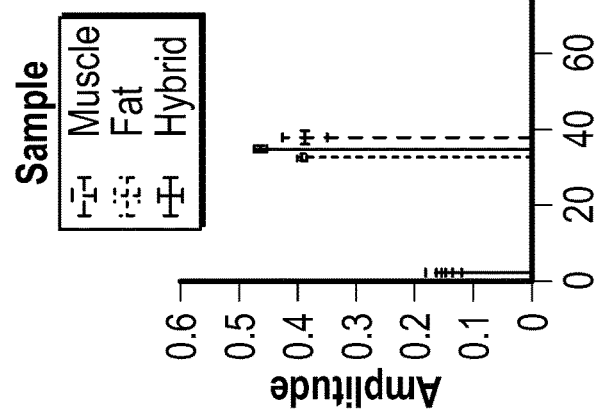

The identification of tissue fractions was demonstrated from an MR signal acquired with the portable MR sensor. Muscle and fat tissue were extracted from a rat and measured with the CPMG pulse sequence on the sensor to establish reference signals (FIG. 2A) (See above Portable MR sensor measurements of ex vivo tissue). The signals from fat and muscle decay at different rates. Triexponential fits (Eq. (2)) of these decay curves show that the relaxation peaks are distinct between muscle and fat (FIG. 2B). A hybrid sample was prepared as a heterogeneous mixture of small (~1 mm) pieces of muscle and fat tissue. The hybrid sample has a decay rate between that of its constituent signals (FIG. 2A).

Figure 15A:
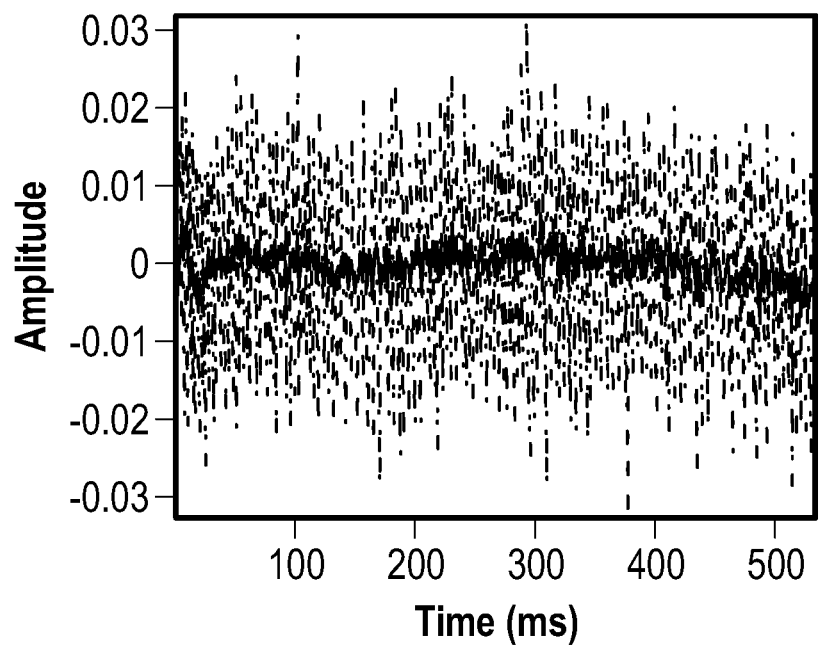
FIGS. 15A-15B are graphs illustrating residuals of ex vivo tissue hybrid sample. Residuals from triexponential (FIG. 15A) and 6 exponential model (FIG. 15B). Light grey lines correspond to the raw residuals. Black lines correspond to a low pass filtered (moving average, window size of 15 samples) residual signal.
Figure 15B:
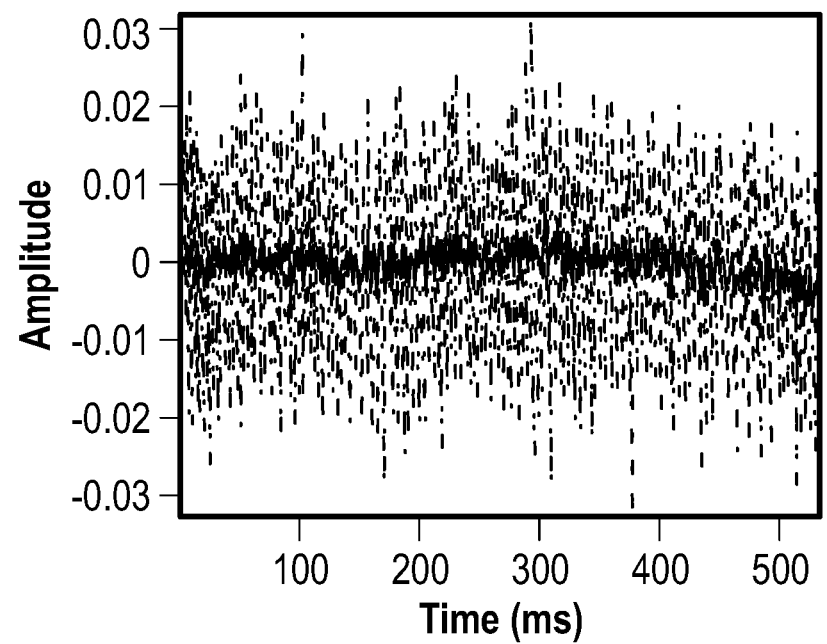

A multiexponential fit of all of the relaxation times from both muscle and fat failed to appropriately assign amplitudes to each of the six constituent relaxation peaks. Parameter extraction from multiexponential decays is an ill-posed problem, especially when some decay rates are similar. This problem is further exacerbated by the presence of noise. Furthermore, a triexponential fit is sufficient to fully model the multiexponential nature of the hybrid signal, as its residuals are very similar to those of a six exponential fit (FIGS. 15A-15B). The relaxation peaks of the hybrid sample are each between those of muscle and fat when fit as a triexponential signal (FIG. 2B). Attempting to use the amplitudes produced by the triexponential fit as an estimate of the relative fraction of muscle and fat within the hybrid signal is not possible as each relaxation peak has an unknown contribution from both constituent signals.

An algorithm was developed to estimate the fraction of tissues within the hybrid signal through an iterative approach that minimizes the error between the measured signal and a synthetic signal based on an estimated ratio of constituent tissues (See above Algorithm for identification of constituent signal fractions). This algorithm recovered the fractions of muscle and fat within the hybrid signal to within a 2% error (FIG. 2C). This algorithm performed successfully despite the triexponential nature of each of the constituent signals.

Our algorithm allowed for isolation and further analysis of a signal corresponding to a single tissue despite corruption of the acquired signal by another tissue with similar relaxation peaks. The acquired hybrid signal was unsuitable for standard exponential fitting based analysis methods due to the overlap of the constituent relaxation peaks. This problem was unique to inverse problems comprised of decaying exponentials due to their ill-posed nature. We demonstrated this algorithm with multiexponential signals acquired from ex vivo fat and muscle tissue. This approach can be applied in other settings, such as estimating the change in relaxation properties of a single tissue due to a disease of pathology that causes a relaxation time shift within a tissue exhibiting a multiexponential MR signal.

This technique could be extended to consider multiple signals from each constituent tissue in order to improve its robustness, especially towards complex samples. Two measurements could be performed with different sensitivities towards spin diffusivity, for example, for each constituent tissue and for the hybrid sample. The addition of the second signal would increase the orthogonality of the basis signals, if the constituent samples have differences in diffusivity, and, therefore, may increase the accuracy and/or robustness of the technique in the presence of noise or other confounding signals. This same approach could also be applied with other pulse sequences (e.g. inversion recovery, saturation recovery, stimulated echoes, pulsed gradient echo, etc.) to take advantage of differences in T1, T2, and/or diffusivity in combination.

Depth Sensitivity Profile and Tissue Fraction Estimation Improves Muscle Measurement Localization The MR signal originating from the more distal muscle tissue is most relevant to the diagnosis of fluid disorders. The optimal measurement with our portable MR sensor would select an RF excitation frequency that sufficiently localizes the measurements towards the muscle tissue without unnecessarily sacrificing sensitivity. Smaller RF excitation frequencies enable increased measurement penetration depth at the expense of sensitivity (FIG. 1C). The optimal choice of RF excitation frequency should be informed by the local variation in subcutaneous thickness where regions with increased thickness will require a decreased frequency to achieve sufficient measurement penetration.

Figure 3A:
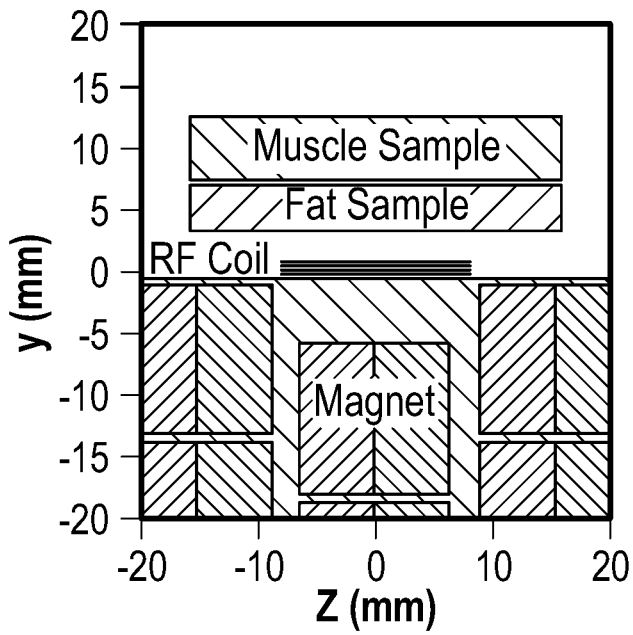
FIGS. 3A-3D show an estimation of proximal subcutaneous tissue thickness, according to one embodiment.
Figure 16:
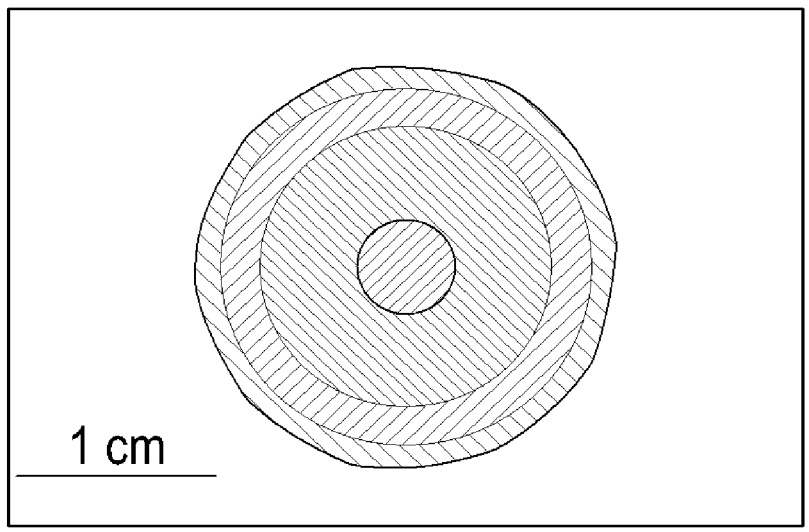
FIG. 16 is an illustration of a synthetic subcutaneous tissue phantom used in experiments with the MR sensor disclosed herein. The tissue phantom was formed of a PEEK housing defining a cavity filled with soybean oil.

Estimation of proximal subcutaneous tissue thickness with the portable MR sensor was demonstrated. First, synthetic tissue phantoms were fabricated to mimic the relaxation properties of subcutaneous tissue and muscle tissue via aqueous solutions with varying concentrations of a paramagnetic species ($CuSO_4$) (See above Synthetic tissue phantoms). The phantoms were designed to fully span the sensitive region of the sensor (FIG. 16). The relaxation times of the synthetic subcutaneous tissue phantom were similar to that of ex vivo tissue while allowing for precise control over sample geometry (FIG. 17). The phantoms were then arranged with the subcutaneous tissue directly in contact with the RF coil of the portable MR sensor and the muscle tissue placed against the subcutaneous tissue phantom (FIG. 3A). The thickness of the subcutaneous tissue was varied (1, 1.3, 1.5, and 3 mm) to mimic natural variability both within and between patients. We measured each configuration of phantoms with the CPMG pulse sequence with six unique RF excitation frequencies. Simulations were performed to identify the necessary signal to noise ratio (SNR) to accurately estimate the muscle fraction from a heterogeneous signal (FIGS. 18A-18F). The results of this simulation guided measurements of phantoms. The fraction of the signal corresponding to each constituent tissue was estimated using the described algorithm (See above Algorithm for identification of constituent signal fractions).

Figure 3B:
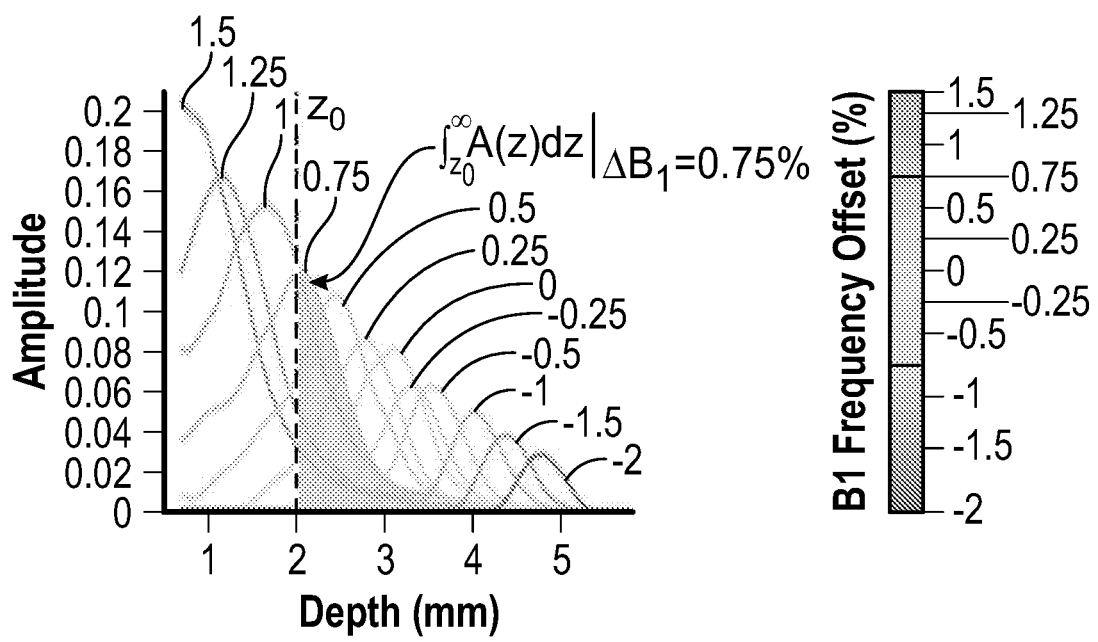
Figure 3C:
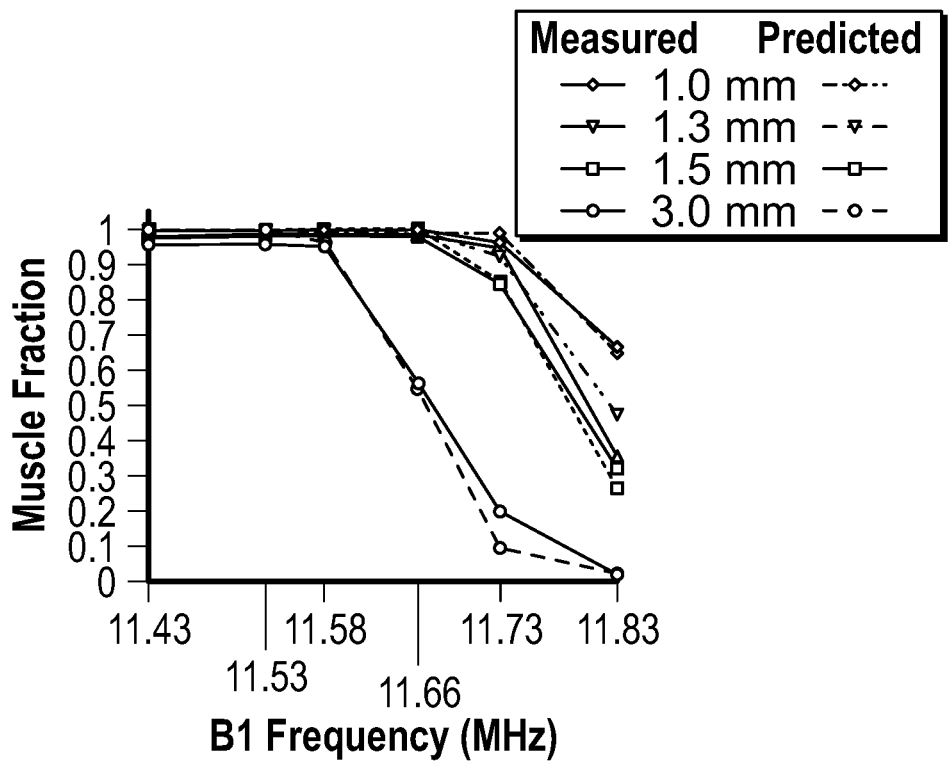

The expected signal amplitude originating from the distal muscle tissue for a given subcutaneous thickness (e.g., 2 mm) was estimated as the integral of the sensor sensitivity profile taken across the expected depth of the muscle tissue (e.g., greater than 2 mm) for each RF excitation frequency (FIG. 3B). This was converted to an estimate of the muscle tissue fraction by dividing it by the integral of the entire sensitivity profile at the given RF excitation frequency. This technique was used to precisely quantify subcutaneous tissue thickness from measurements of a muscle sample with a more proximal layer of subcutaneous tissue. Estimates of muscle fraction from experimentally acquired signals showed strong agreement with estimated muscle fractions for the same subcutaneous thickness across a wide range of RF excitation frequencies (FIG. 3C).

Figure 3D:
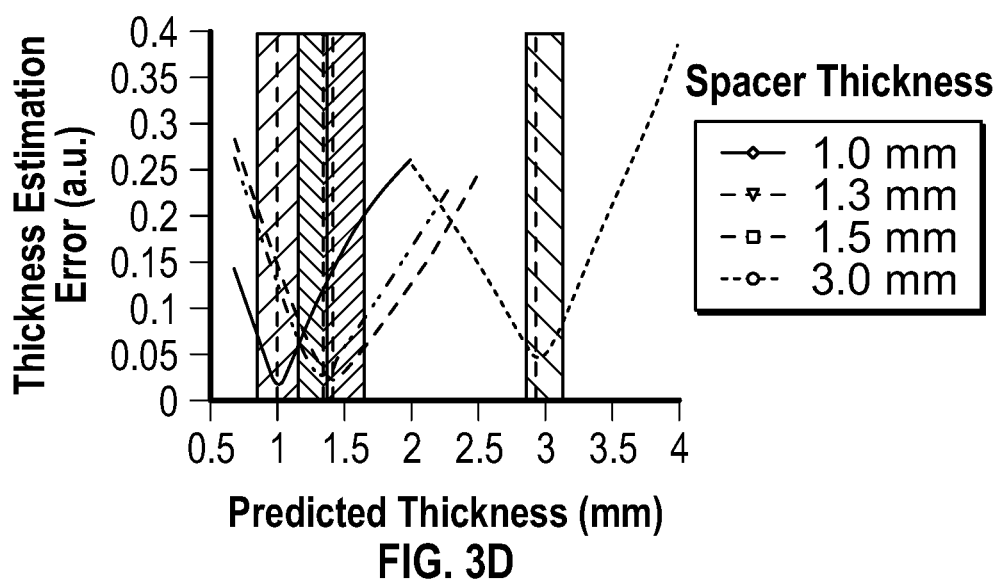

Sensor sensitivity as a function of depth was used for precise estimation of the thickness of the subcutaneous tissue. The muscle fractions generated by integrating the sensitivity profiles for a candidate thickness was compared with muscle fractions from experimentally acquired signals. The optimal candidate thickness were then identified by minimizing the error between muscle fraction estimates and those from the measured signal. This optimal thickness represented the actual thickness of each phantom (FIG. 3D). Estimation of phantom thickness using this approach was accurate to within 0.1 mm, which is smaller than the tolerance on the construction of the phantoms (0.3 mm).

More precisely estimating the depth profile with thinner planar samples could improve phantom thickness estimation accuracy.

An algorithm to perform acquisition at the optimal RF excitation frequency could be implemented by utilizing this method. The optimal RF excitation frequency would be sufficiently low as to ensure a significant fraction of the sensitive region is located within the target tissue without being so low as to unnecessarily sacrifice sensitivity. This optimal frequency would be dependent on the subcutaneous tissue thickness, geometry of the portable MR sensor, and pulse parameters (e.g. excitation pulse bandwidth). Estimation of the optimal RF excitation frequency is made more robust and accurate by performing measurements of a tissue geometry at multiple RF excitation frequencies.

Varying Echo Time Enables Sensitivity Towards Sample Diffusivity

Distinct tissues can have very similar relaxation properties (e.g., times and amplitudes) making identification and further characterization of changes in relaxation properties difficult. Measurements of relaxation properties via CPMG are inherently affected by the diffusivity of spins (e.g. water in tissue) within the sample. Here we demonstrated that explicitly manipulating the echo time within CPMG allows control over the effect of diffusivity on the relaxation properties of the signal with our portable MR sensor.

Varying the echo time between excitation and subsequent refocusing pulses provides control over the magnitude of signal attenuation induced by sample diffusivity. Signal attenuation between sequential refocusing pulses in CPMG is driven by both T2 decay and the motion of spins within the magnetic field. The T2 decay term is proportional to the echo time, while the diffusion term is proportional to the echo time cubed. Therefore, by controlling the echo time, the relative signal attenuation due to each factor can be varied.

Figure 4A:
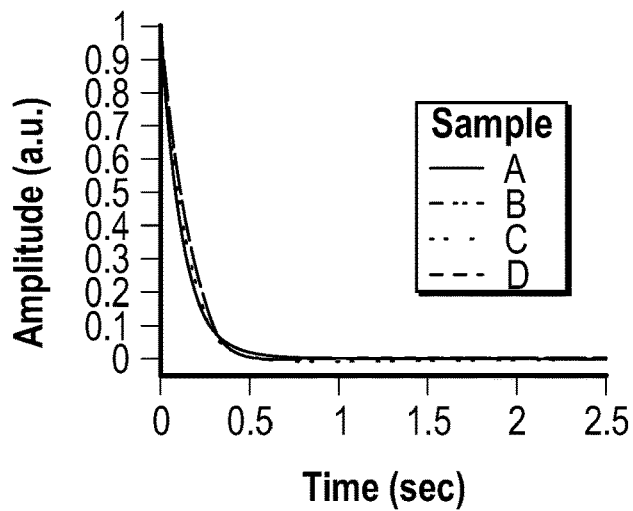
FIGS. 4A-4I are graphs showing how varying echo time provides portable MR sensor with sensitivity towards sample diffusivity.
Figure 4B:
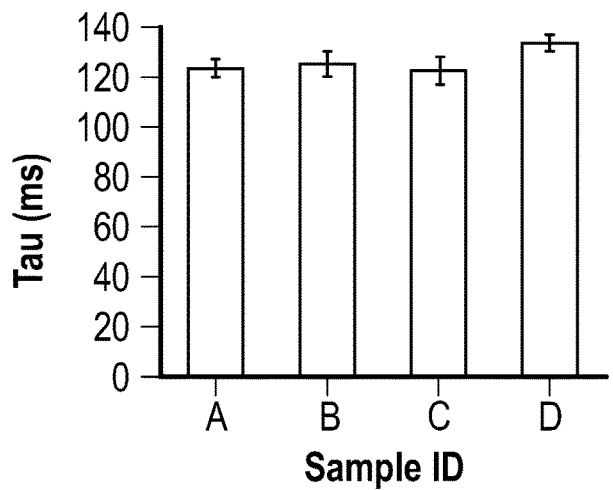
Figure 4C:
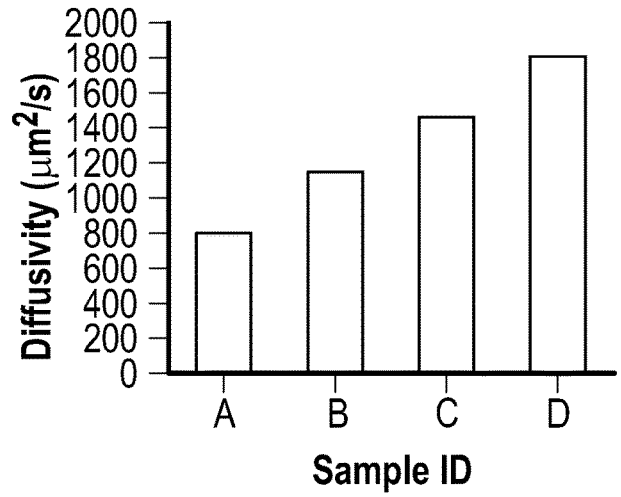

Four aqueous solutions of polyethylene glycol (PEG) and gadolinium were prepared with identical T2 relaxation time and distinct diffusion coefficients (See above: In vitro diffusion experiments). PEG concentration primarily affected the diffusivity of water, while gadolinium primarily affected relaxation properties. T2 relaxation times were estimated via measurements on a benchtop NMR spectrometer via CPMG. The time domain signals and T2 relaxation times, estimated via a monoexponential fit, were nearly identical across all samples (FIGS. 4A-4B). The diffusivity of water within the samples, estimated via pulsed gradient spin echo pulse sequence on a Bruker NMR spectrometer, varied significantly with PEG concentration (FIG. 4C).

Figure 4D:
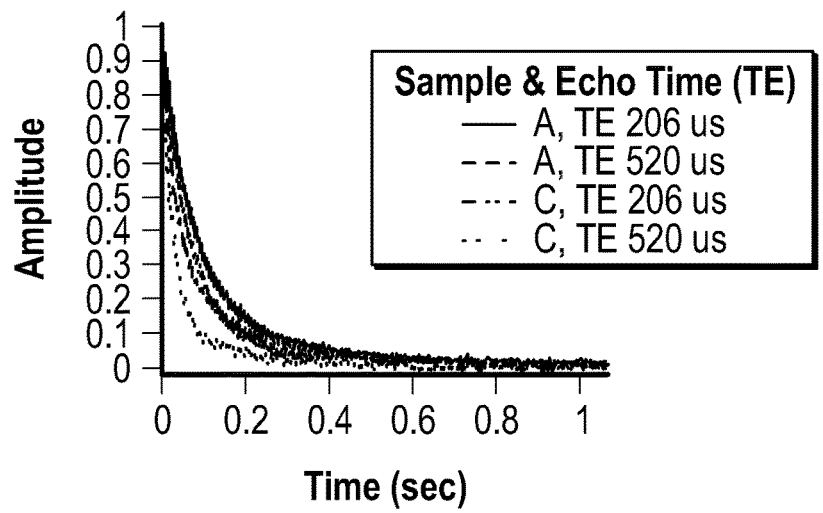
Figure 4E:
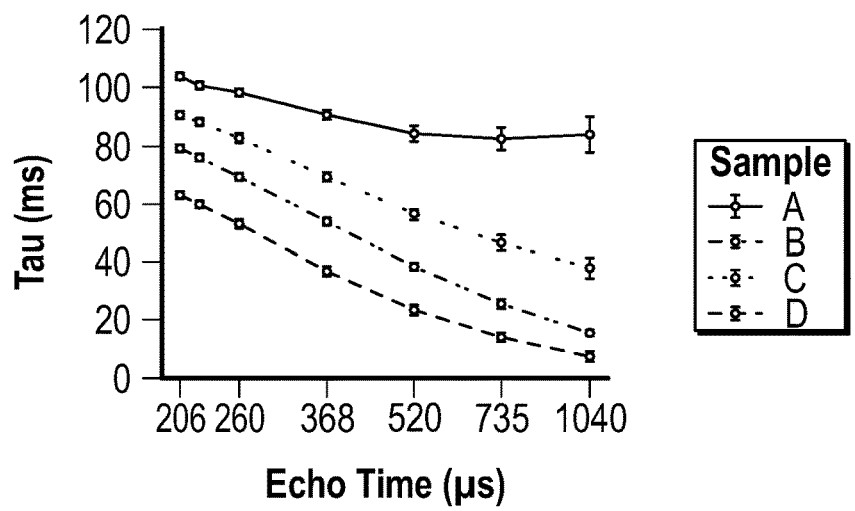
Figure 4F:
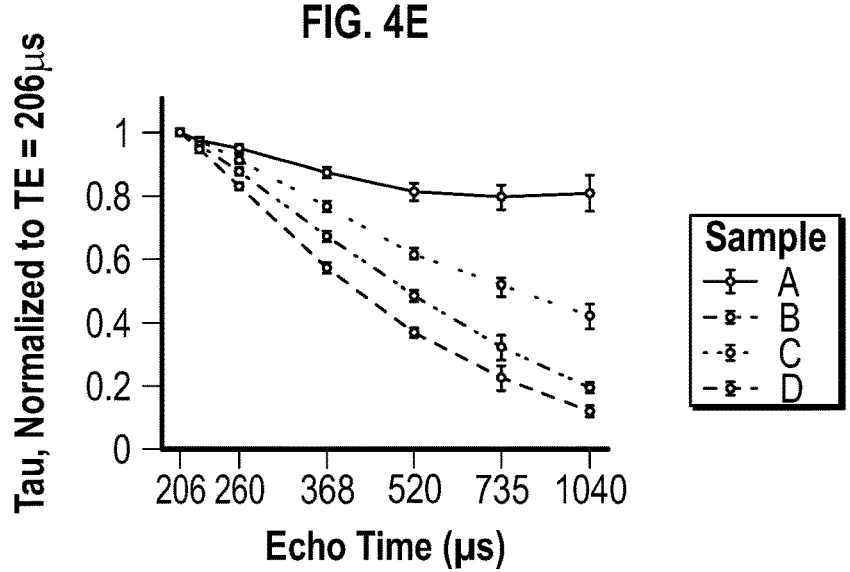

Measurements of the aqueous solutions were performed with CPMG with varying echo time with the portable MR sensor (FIGS. 4D-4F). The change in decay rate in the time domain (FIG. 4D) and estimated relaxation time extracted from a monoexponential fit (Eq. (2)) (FIG. 4E) of each sample differed as a function of echo time. Increased echo time led to a decrease in relaxation time. The magnitude of this decrease was more pronounced with increased sample diffusivity. The relative change in relaxation time as a function of echo time clearly stratifies samples by diffusivity (FIG. 4F). For example, the sample with the highest diffusivity exhibited an 88% decrease in relaxation time, while the sample with the lower diffusivity exhibited only a 19% decrease in relaxation time between the fastest and slowest echo time acquired.

Figure 4G:
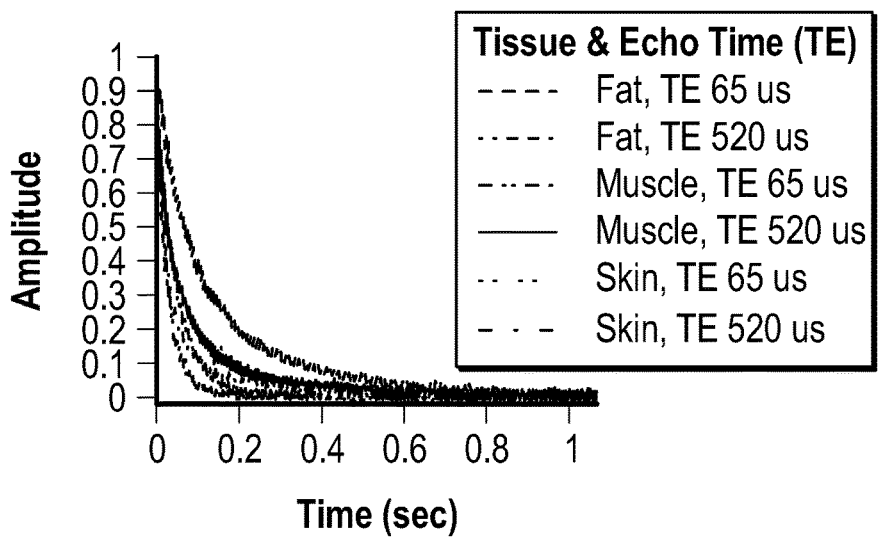
Figure 4H:
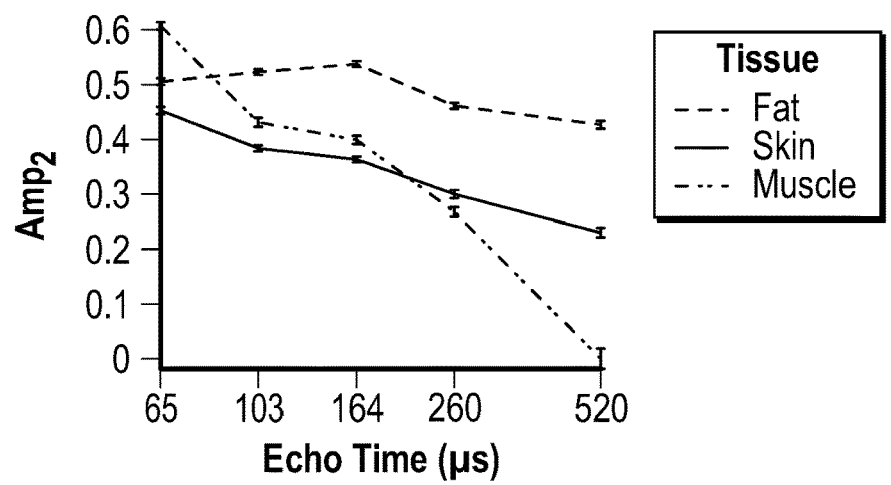
Figure 4I:
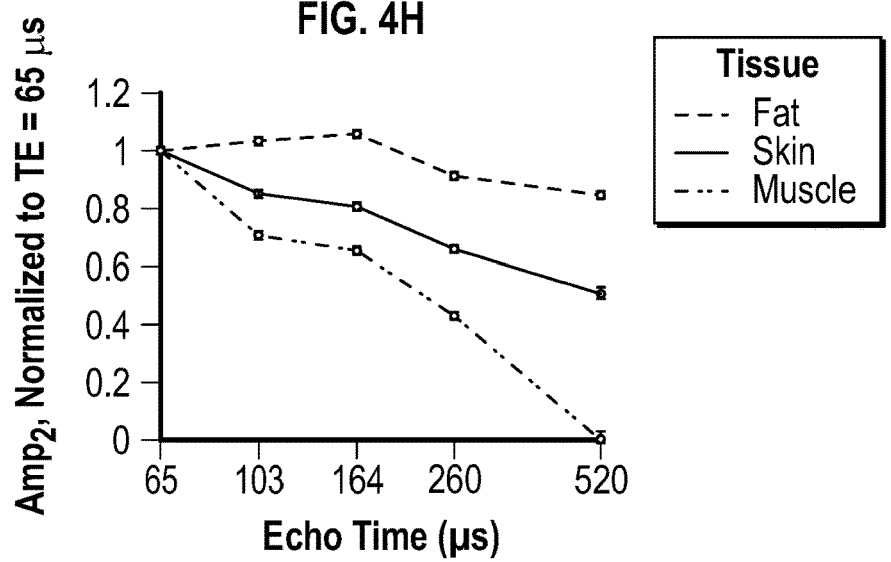

Three distinct ex vivo tissues were then measured on the portable MR sensor to demonstrate that this technique is capable of identifying differences in diffusivity within complex samples producing multiexponential signals (See above: Ex vivo tissue diffusion experiments). Fat, skeletal muscle, and skin were excised from a rat and measured with CPMG with varying echo times. The change in decay rate of each signal was dependent on echo time (FIG. 4G). A biexponential fit was then performed to identify the effect of varying echo time on the amplitude corresponding to the slower, more highly diffusive fluid compartment of each tissue. The second amplitude from the biexponential fit of the muscle signal decreased more quickly with echo time than that of the skin or fat signals (FIG. 4H). This showed that the relative diffusivity of water within the slow component of muscle was greater than that of skin and fat (34-36). Furthermore, the relative change in this amplitude as a function of echo time clearly stratified each tissue which allowed for straightforward identification of each tissue despite similarities in relaxation properties (FIG. 4I).

Sensitivity toward diffusivity with the portable MR sensor was demonstrated by taking advantage of its highly inhomogeneous static magnetic field. This measurement was performed by varying the echo time which served a similar purpose as the switchable gradient fields found in more traditional implementations of diffusion-weighted pulse sequences. The relatively high static magnetic field inhomogeneity, a characteristic of most single-sided MR sensors, enabled strong diffusion weighting to be achieved with relatively short echo times. The dependency of relaxation time on both echo time and sample diffusivity can be used to identify the T2 and diffusivity of a sample.

Muscle Edema Induces Shift in Multicomponent T2 Relaxometry MR Signal

Figure 5A:
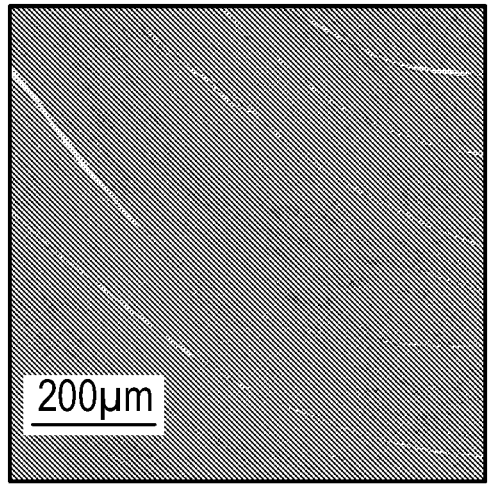
FIGS. 5A-5F show intramuscular muscle edema shifts multicomponent T2 relaxometry signal.
Figure 5B:
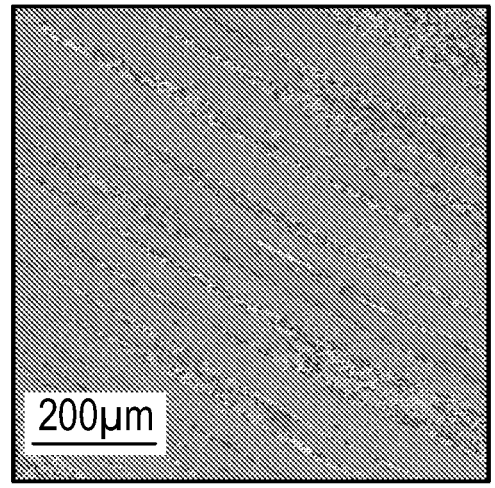
Figure 5C:
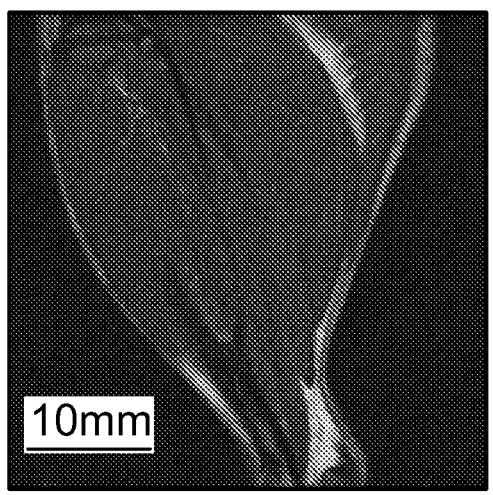
Figure 5D:
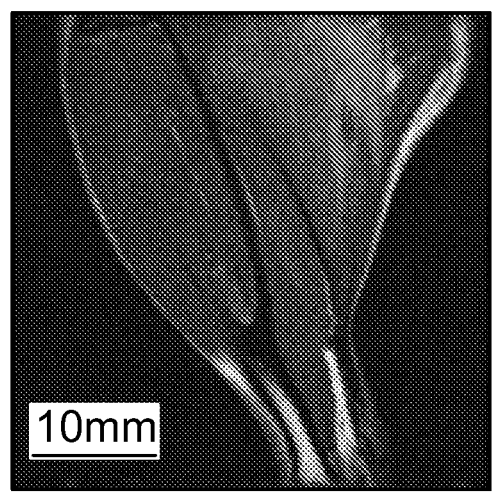
Figure 5E:
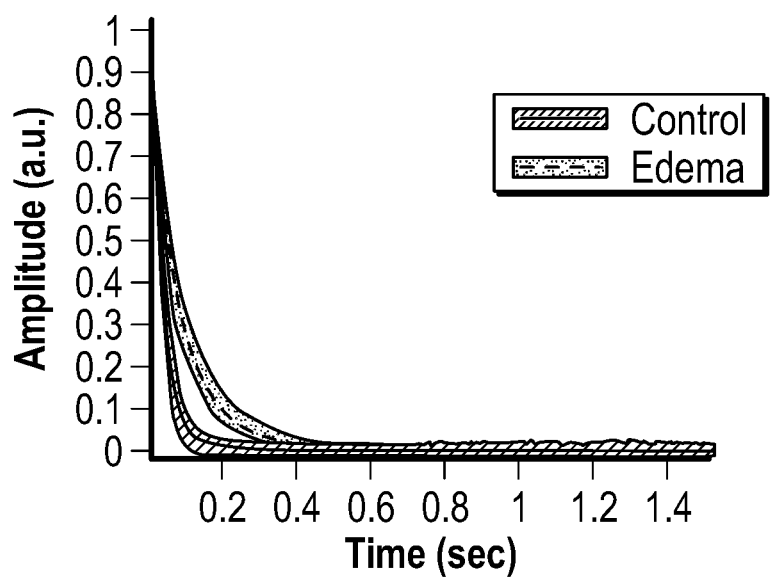
Figure 5F:
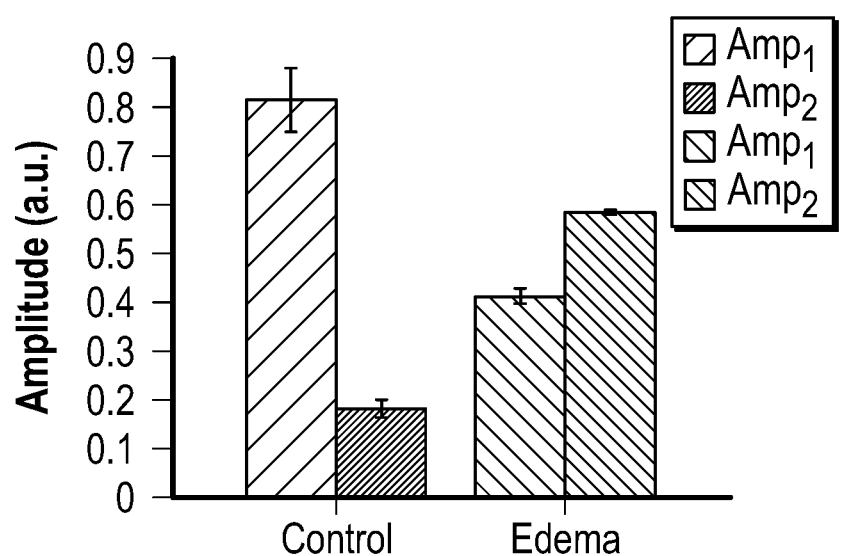

Acute, focal muscle edema was induced to expand the intramuscular interstitial fluid compartment via injection of λ-carrageenan into the biceps femoris muscle in the lower leg of a rat (See above: Muscle edema model). The presence of muscle edema was confirmed via hematoxylin and eosin (H&E) staining of muscle tissue adjacent to the site of injection (FIGS. 5A-5B). Muscle tissue after λ-carrageenan injection shows increased white blood cell infiltration and an expanded interstitial space causing edema. The presence of muscle edema was further established via T2-weighted MRI of the lower leg before (FIG. 5C) and after (FIG. 5D) injection (See above Identification of muscle edema). The region of hyperintensity in the biceps femoris muscle, visible in the image 24 hours after injection, indicated fluid accumulation in the interstitial space (FIG. 5D). A series of spin echo MRI images were acquired to provide a T2 decay curve for quantitative characterization of muscle edema (FIGS. 5E-5F). Composite T2 decay signals formed from voxels corresponding to muscle tissue indicated an increase in decay time from before to 24 hours after injection (FIG. 5E). A biexponential fit demonstrated an increase in signal amplitude corresponding to the intramuscular ECF (FIG. 5F).

Measurement of Muscle Edema Despite Proximal Subcutaneous Tissue

It was shown that the portable MR sensor can identify these changes in intramuscular fluid distribution induced by muscle edema despite the presence of a confounding signal from proximal subcutaneous tissue. This was achieved by localizing the signal via tuning of the RF excitation frequency and by isolating the muscle signal via diffusion-weighted measurements and T2 multicomponent relaxometry.

Figure 6A:
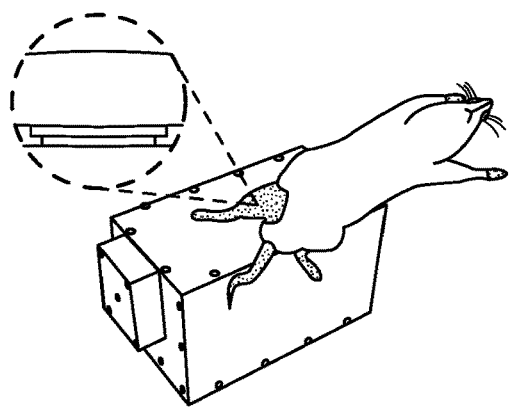
FIGS. 6A-6F illustrate an embodiment of a portable MR sensor which identifies onset and recovery of acute muscle edema.

The hind leg of the rat was placed on top of the RF transceiver coil of the portable MR sensor (FIG. 6A). A synthetic subcutaneous tissue phantom, located between the sensor and the rat leg, simulated the presence of a substantial subcutaneous tissue layer. The subcutaneous tissue phantom consisted of a cylindrical volume of soybean oil enclosed in a thin plastic housing (FIG. 13A). The subcutaneous tissue phantom appeared as a biexponential signal when measured with the portable MR sensor with relaxation times of 58 and 226 ms (FIG. 13B).

Figure 6B:
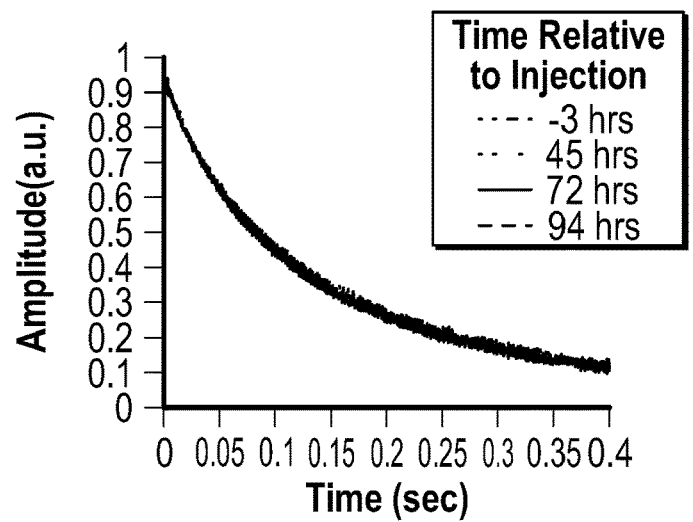
Figure 6C:
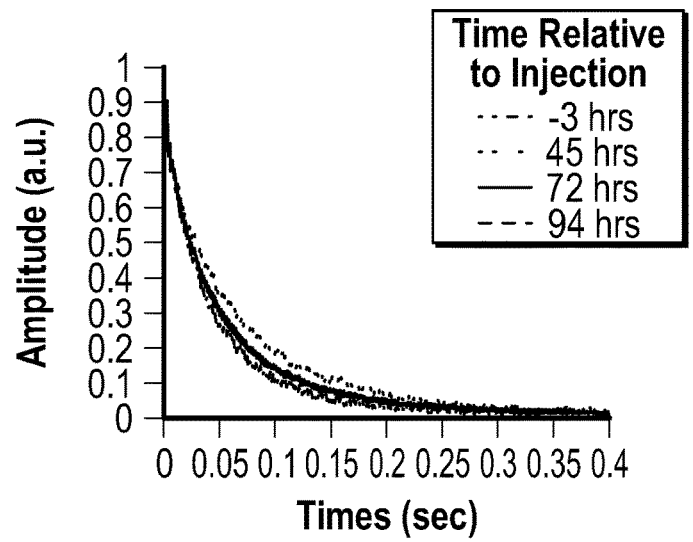
Figure 6D:
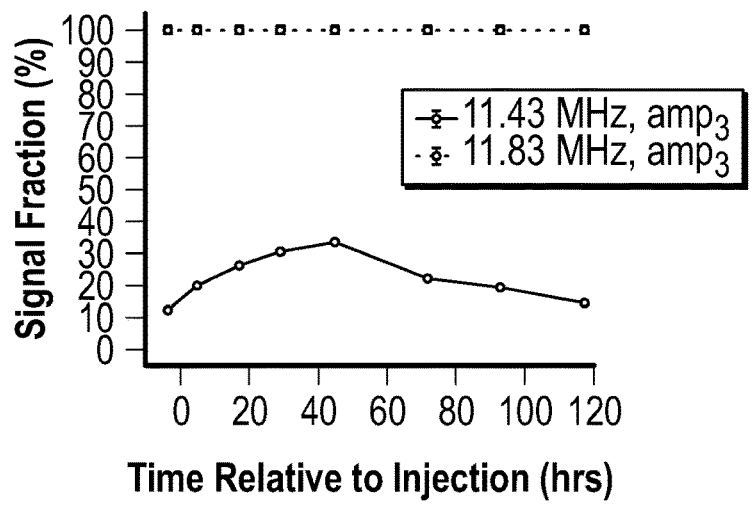
Figure 6E:
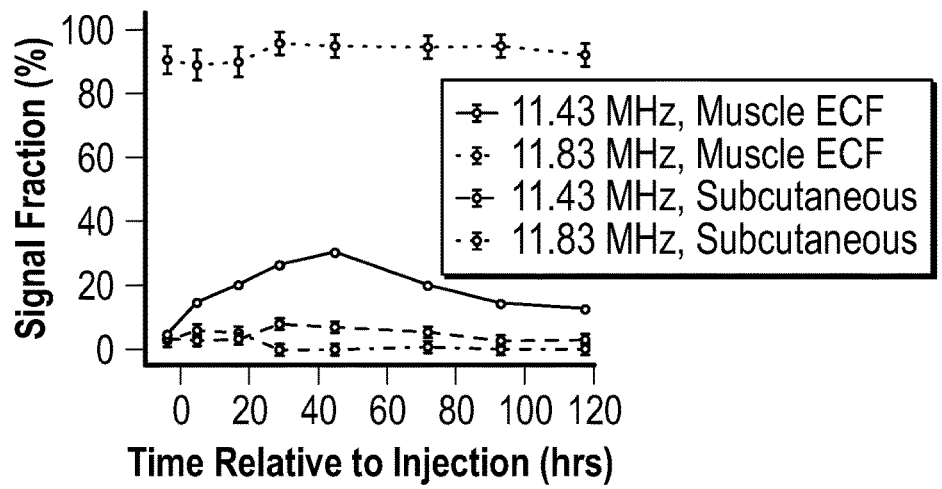
Figure 6F:
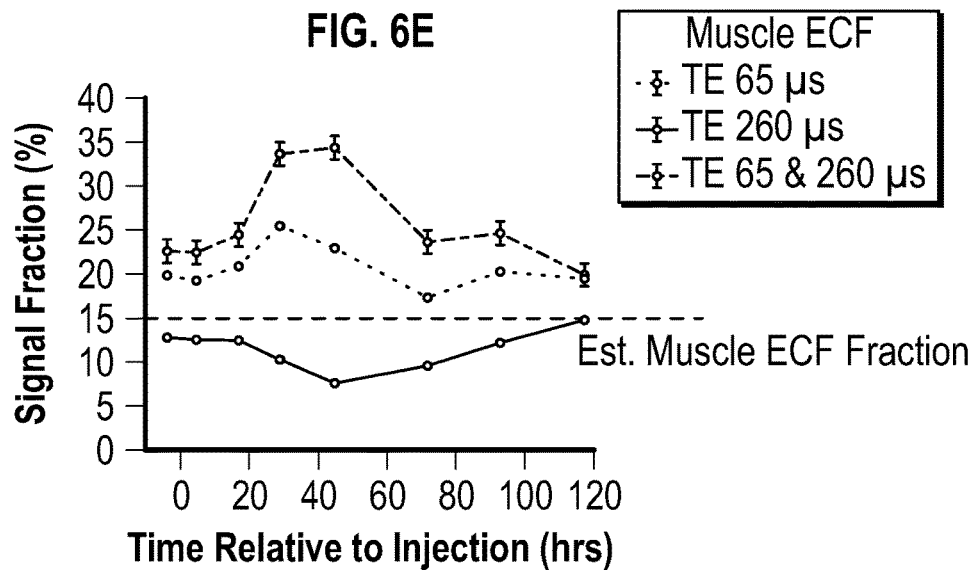

MR measurements were performed before injection and longitudinally at regular intervals for a total period of 121 hours (See above: Identification of muscle edema via portable MR sensor). The first set of MR measurements demonstrated the utility of achieving target localization via tuning RF excitation frequency. A series of MR measurements acquired at a high RF excitation frequency (11.83 MHz) were unable to resolve changes in the signal originating from the muscle tissue as the signal was largely localized towards the proximal subcutaneous tissue (FIG. 6B). Identical measurements performed at a lower RF excitation frequency (11.43 MHz) clearly identified an increase in decay rate associated with onset of muscle edema, followed by a reversion toward the baseline signal (FIG. 6C).

A triexponential fit (Eq. (2)) was performed on the sum of these signals to identify a set of mean relaxation times (2, 40, and 121 ms). A triexponential fit with fixed relaxation times (Eq. (3)) was then performed using these relaxation times to identify changes in the amplitude of the slow component that may be attributed to muscle edema. These fits showed that the 11.83 MHz signals for all time points solely comprised the slow component corresponding to the subcutaneous tissue (FIG. 6D). This precluded the use of these measurements to identify muscle edema. In contrast, the amplitude of the same component in the 11.43 MHz signal responded to intramuscular interstitial fluid shifts concomitant with muscle edema. This signal showed a significant response to the onset of edema (n=42 and 41, p<0.0001, statistics by t test), its consistent progression (n=5, p<0.01, statistics by significance of Spearman rank correlation), and its ultimate recovery towards baseline (n=52 and 45, p<0.0001, statistics by t test). This process was then repeated with a five exponential model (tau: 2, 40, 58, 121, and 226 ms) to capture the triexponential signal corresponding to the muscle and the biexponential signal corresponding to the subcutaneous fat tissue (FIG. 6E). The subcutaneous fat signal comprised the majority of the 11.83 MHz signal with a negligible fraction being assigned toward the muscle extracellular fluid (ECF). The muscle ECF signal in the 11.43 MHz signal responded to intramuscular fluid shifts, while the amplitude of the subcutaneous fat signal remained approximately constant. This signal, once again, showed a significant response to the onset of edema (n=42 and 41, p<0.0001, statistics by t test), its consistent progression (n=5, p<0.01, statistics by significance of Spearman rank correlation), and its ultimate recovery towards baseline (n=52 and 45, p<0.0001, statistics by t test). A small increase in the subcutaneous fat signal at 29 and 45 hours was likely leakage of the muscle ECF signal due to both increased amplitude and relaxation time as a result of the onset of edema.

The measurement of a region with a considerable fraction of subcutaneous tissue may be unavoidable, even with tuning of the RF excitation frequency, in cases of substantial subcutaneous thickness. In addition, it may be desirable to select a higher RF excitation frequency to decrease total acquisition time even though the measurement may include some subcutaneous signal. In these cases, the aforementioned technique may be unable to resolve changes in the relaxation properties of the muscle. The use of a diffusion-weighted signal can help resolve signals originating from tissues or fluid compartments with distinct diffusivities.

Measurements during the onset and recovery of muscle edema were performed at an RF excitation frequency of 11.60 MHz, representing a target region spanning both the subcutaneous tissue and the muscle tissue. These measurements were performed at an echo time of 65 μs, similarly to previous measurements, and an additional echo time of 260 μs which applied increased diffusion weighting. The amplitudes of the slow component in a triexponential fit, corresponding primarily to the muscle ECF signal, at an echo time of 65 μs did not vary appreciably in response to muscle edema (FIG. 6F). This signal failed to identify the onset of edema (n=40 and 39, p=1.0000, statistics by t test) or its progression (n=5, p=0.1167, statistics by significance of Spearman rank correlation) although it did identify the recovery towards baseline (n=47 and 39, p<0.0001, statistics by t test). The amplitudes of this muscle ECF signal at an echo time of 260 μs decreased in response to muscle edema due to the increased diffusivity of water within the interstitial space (37). This diffusion-weighted signal can enhance the signal corresponding to the muscle ECF without bias from the subcutaneous tissue signal (FIG. 6F). We first identified the expected muscle ECF signal fraction at an echo time of 260 μs based on the known sensitivity profile of the MR sensor at 11.60 MHz. The deviation from this baseline muscle ECF signal fraction observed in the 260 μs signal was due to the increased diffusivity of the muscle ECF in response to muscle edema, which we observed as signal attenuation. The difference of the 260 μs muscle ECF signal amplitude from the reference value was used to enhance the 65 μs muscle ECF amplitude (See above: Identification of muscle edema via portable MR sensor). This adjusted signal more strongly identified the expected expansion (n=5, p<0.05, statistics by significance of Spearman rank correlation) and subsequent depletion (n=49 and 41, p<0.0001, statistics by t test) of the muscle ECF in response to muscle edema.

The portable MR sensor can identify the progression of acute muscle edema, which is utilized here as a model for fluid accumulation in the intramuscular ECF. In cases of moderate subcutaneous tissue thickness, the increased penetration depth offered by varying the RF excitation frequency serves to localize the measurement completely within the muscle tissue. In circumstances where the subcutaneous thickness is more substantial and localization by tuning the RF excitation frequency is insufficient, a diffusion-weighted measurement can help identify changes in the signal that are associated with fluid shifts within the intramuscular ECF. The combination of diffusion-weighted, depth-resolved multicomponent T2 relaxometry with a single-sided MR sensor offers the unique ability to identify shifts in tissue fluid distribution despite the presence of confounding tissue layers.

Example 2: Dehydration Assessment Via a Non-Invasive, Miniature, Portable Magnetic Resonance Sensor Using Multicomponent T2 Relaxometry A portable, miniaturized magnetic resonance-based platform for the diagnosis of dehydration was demonstrated. The miniaturized (1000 cm$^3$) portable (~4 kg) magnetic resonance (MR) sensor was capable of identifying and quantifying dehydration-induced fluid loss. The ability of this single-sided MR sensor was first characterized to perform high-sensitivity, remote multicomponent T2 relaxometry.

Portable MR Sensor for Remote, Multicomponent T2 Relaxometry

Figure 19A:
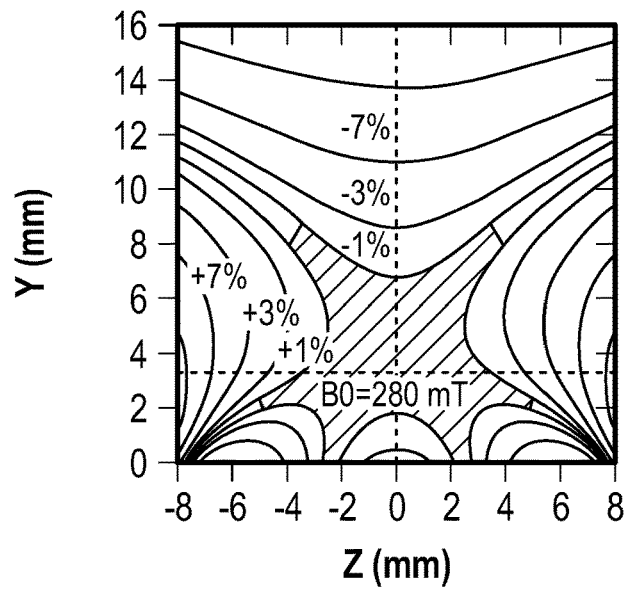
FIGS. 19A-19C show one embodiment of a static magnetic field profile characterization of a portable MR sensor as described herein, with FIG. 19A showing a simulated field profile directly above the center of the magnet, indicated by the plane in FIG. 22A. The shaded region indicates predicted sensitive region assuming a transceiver coil sensitive to a region approximately 10 mm wide with a bandwith of ±1%.
Figure 19B:
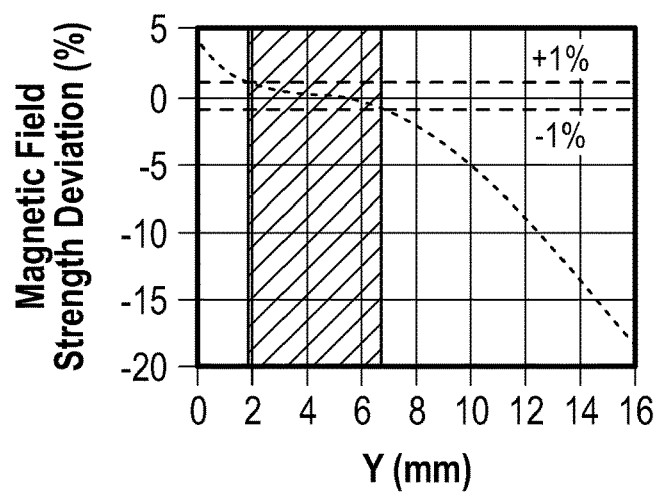
Figure 19C:
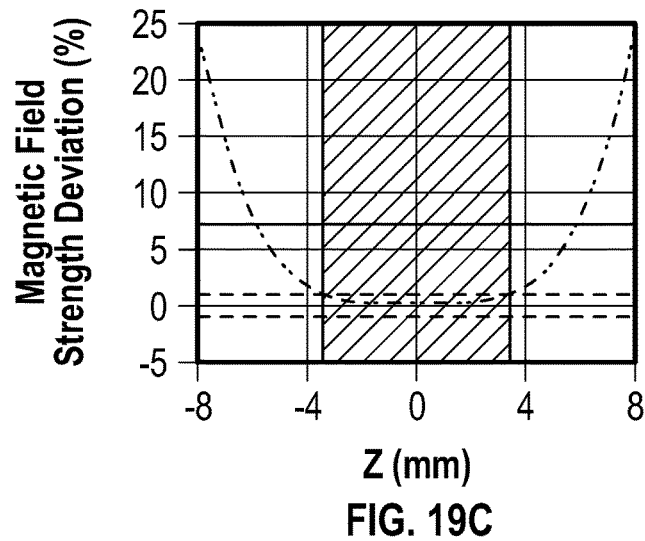
Figure 20A:
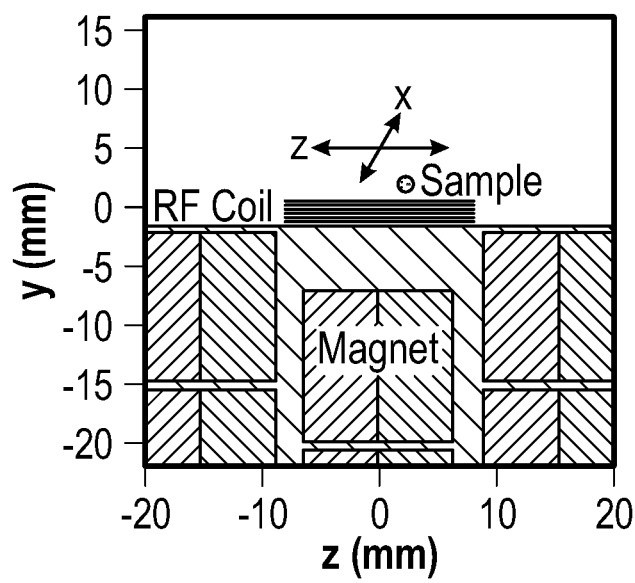
FIGS. 20A-20B illustrate one embodiment of a sensitivity profile characterization of a portable MR sensor as described herein, with experimental schematic for MR sensor sensitivity profiles along the xz-plane (FIG. 20A) and the yz-plane (FIG. 20B). A 3 mm bulb of $CuSO_4$ aqueous solution was scanned across the measurement plane, and the amplitude of the peak corresponding to the solution indicated the signal strength originating from the contents of the bulb.
Figure 20B:
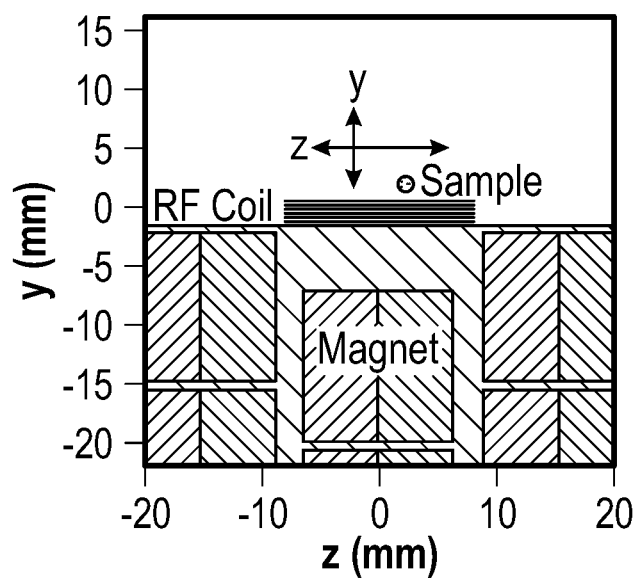
Figure 22C:
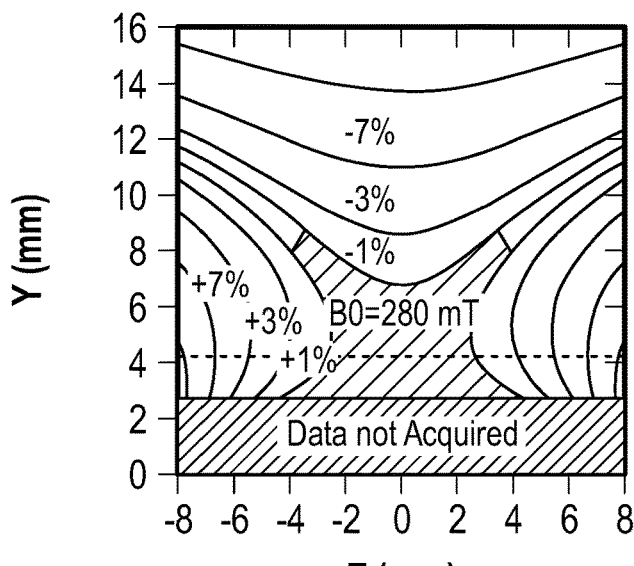
FIG. 22C is a graph showing measured static magnetic field profile directly above center of magnet, according to one embodiment. Shaded region indicates predicted sensitive region.
Figure 22D:
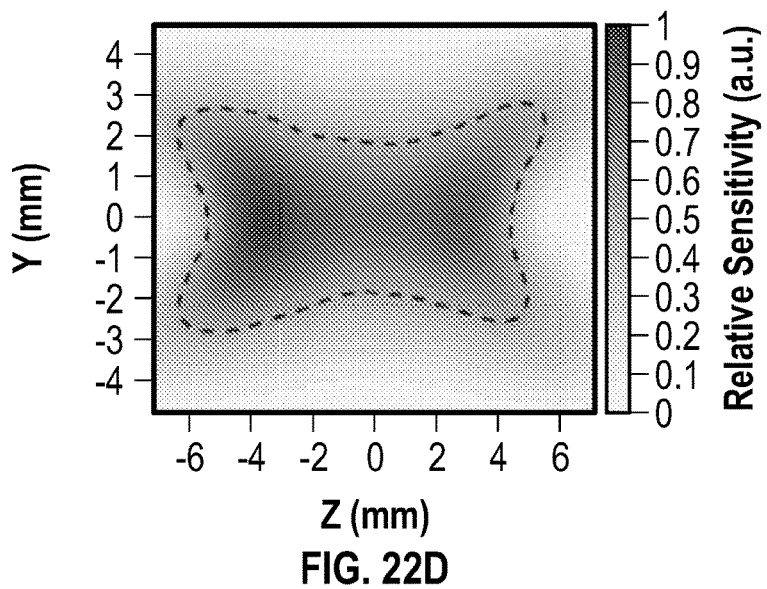
FIGS. 22D and 22E are graphs showing relative sensitivity of sensor across the xz-plane (FIG. 22D) and the yz-plane (FIG. 22E), which indicate a 12×5×2 mm sensitive region. Shaded planes in indicate relative orientation of measurement planes shown in FIG. 22B. Dashed lines indicate 50% relative sensitivity from the peak of the measurement region.
Figure 22E:
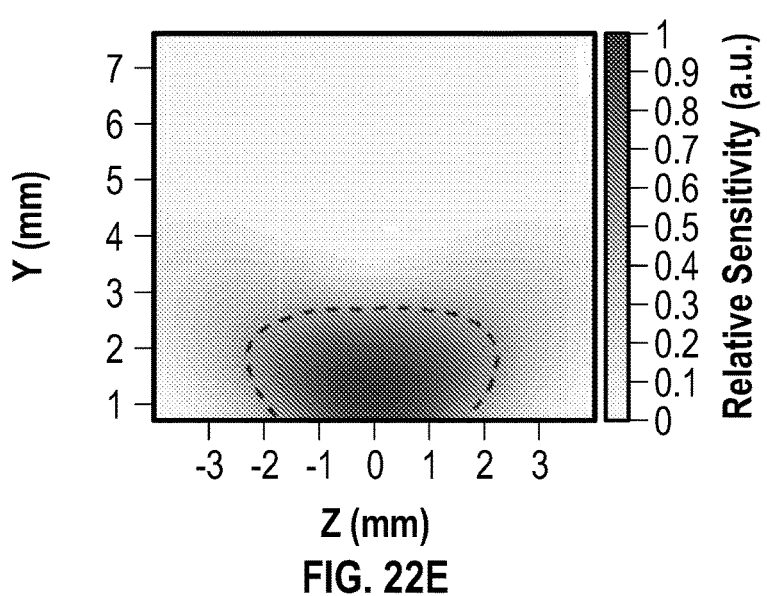

We first designed a portable magnetic resonance sensor capable of measuring the fluid distribution within tissue via multicomponent T2 relaxometry (FIG. 22A). This sensor was designed and constructed with a permanent magnet array to generate a static magnetic field (B0) based on the Unilateral Linear Halbach array (FIG. 22B-C) See Bashyam, et al, J. Magn. Reson. 292:36-43 (2018). This "sweet spot" magnet design enables high sensitivity measurements over a large uniform region compared to more commonly used high gradient designs. Permanent, rare earth magnets provide a means to generate a static magnetic field while also allowing for cost effectiveness, low maintenance, minimal power requirements, and portability compared to the more traditional superconducting magnets found in MRI. Furthermore, the magnetic field is parallel to the surface of the sensor allowing for the use of a standard radiofrequency (RF) transceiver coil in order to maximize sensitivity. The magnet produces a uniform region with a magnetic field strength of 0.28 Tesla located approximately 2 to 7 mm from the surface of the sensor as modeled by field simulations (FIG. 19A) and experimentally confirmed with an acquired field profile (FIG. 22C). The sensitivity of the system was characterized by measuring the relative signal amplitude from a sample scanned through the sensitive region (FIGS. 20A-B). The sensor is sensitive towards a region located directly above the RF coil spanning a volume of 12×5×2 mm (FIGS. 22D-E). This allows localization of the measurement towards skeletal muscle tissue while reducing any confounding signal from subcutaneous tissue (See Moller, et al., Am J. Hum. Biol. Off J. Hum. Biol Assoc. 12:231-239 (2000)). FIGS. 19B-19C show magnetic field strength deviation from B0 along y-axis and z-axis, respectively, through the center of uniform region. Shaded regions correspond to ±1% deviation from B0.

Figure 21A:
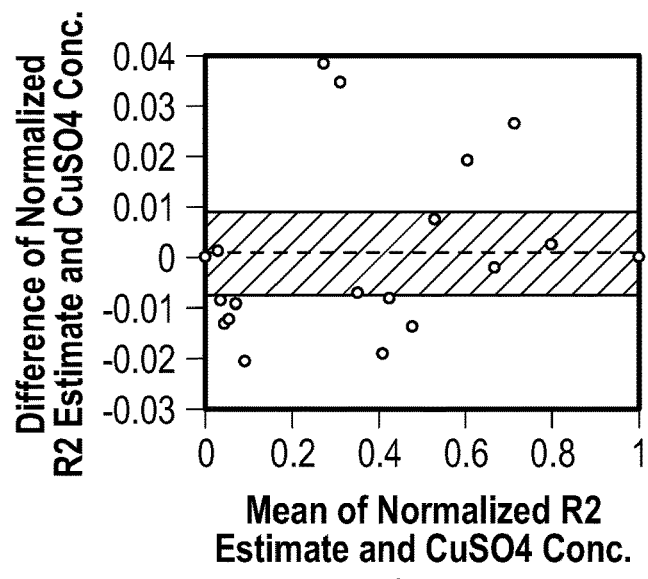
FIG. 21A is a graph that shows validation of T2 relaxometry measurements from portable MR sensors according to one embodiment. Bland-Altman analysis for linear fit of paramagnetic species concentration versus relaxation rate from portable MR sensor. Residuals of linear fit for estimated relaxation rate do not show any trends dependent on paramagnetic species concentration. Residuals of a linear fit are approximately normally distributed (n=19, p=0.768, Lilliefors test for normality). Bland-Altman analysis indicates a linear relationship between sample concentration and estimated relaxation rate across a wide range of concentrations (n=19, mean of differences=0.0008, 95% confidence interval=−0.008 to 0.009, p=0.21, statistics by significance of Spearman rank correlation of means and differences).
Figure 21B:
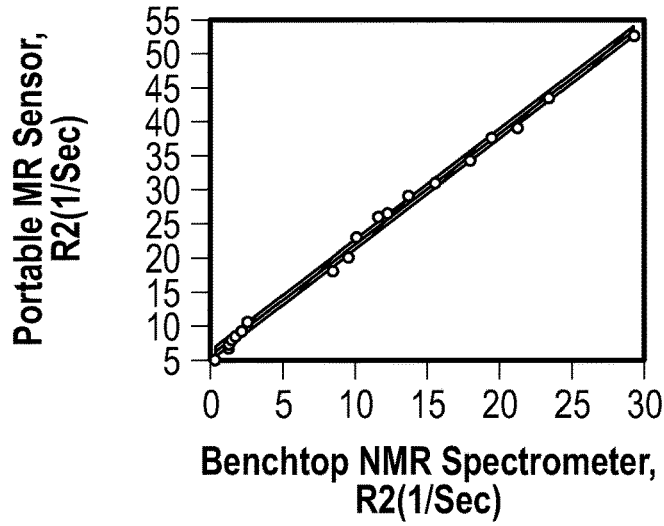
FIG. 21B is a graph that shows validation of T2 relaxometry measurements from a portable MR sensor with benchtop NMR spectrometer, according to one embodiment. The estimated relaxation rates from the two MR systems are linearly related (n=19, $R^2$=0.996, p=1×10$^{-12}$, statistics by t test). Shaded region indicates the standard deviation of the error of the linear fit. Residuals of a linear fit between the relaxation rate estimates between the two MR systems are approximately normally distributed (n=19, p=0.768, Lilliefors test for normality).
Figure 21C:
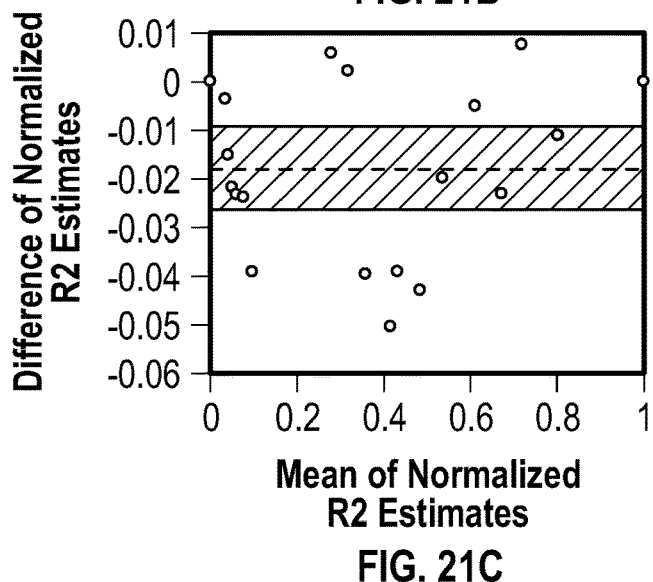
FIG. 21C is a graph that shows no bias in estimation of relaxation rates across a wide range of concentrations per Bland-Altman analysis, indicating strong agreement between the two measurements (n=19, mean of differences=−0.004, 95% confidence interval=−0.012 to 0.004, p=0.70, statistics by significance of Spearman rank correlation of means and differences).
Figure 22F:
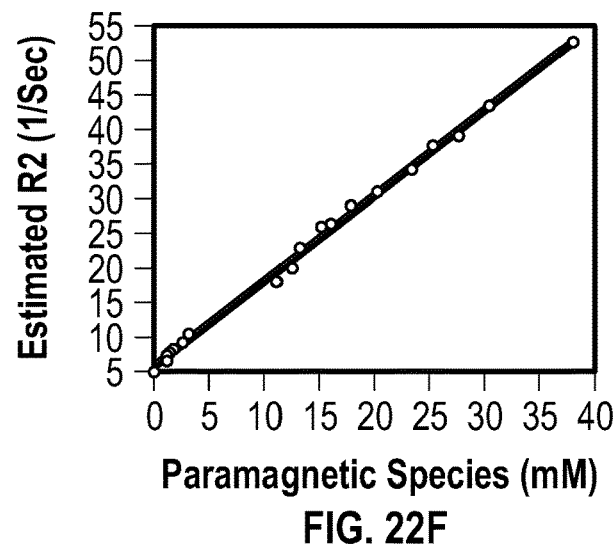
FIG. 22F is a graph showing linearity of R2 relaxometry measurements in one embodiment with a portable MR sensor versus paramagnetic species concentration. Shaded region indicates the standard deviation of the error of the linear fit (n=19, R2=0.997, p<1×10-22, statistics by t test).

The portable MR sensor reliably demonstrates the linear relationship between transverse (T2) relaxation rate and concentration of paramagnetic species ($CuSO_4$) in aqueous solution, a representative synthetic tissue phantom, using a CPMG (Carr-Purcell-Meiboom-Gill) pulse sequence for acquisition (n=19, $R^2$=0.997, $p<1\times10^{-22}$, statistics by t test) (FIG. 22F). There is a linear relationship between sample concentration and estimated relaxation rate across a wide range of concentrations per Bland-Altman analysis (n=19, mean of differences=0.0008, 95% confidence interval=−0.008 to 0.009, p=0.21, statistics by significance of Spearman rank correlation of means and differences) (FIG. 21A). These results are validated against a gold-standard benchtop NMR spectrometer (minispec mq7.5, Bruker, USA) further demonstrating validity of our portable sensor (FIGS. 21B-C). The estimated relaxation rates from the two MR systems are linearly related (n=19, $R^2$=0.996, $p=1\times10^{-12}$, statistics by t test). There is no bias in estimation of relaxation rates across a wide range of concentrations per Bland-Altman analysis indicating strong agreement between the two measurements (n=19, mean of differences=−0.004, 95% confidence interval=−0.012 to 0.004, p=0.70, statistics by significance of Spearman rank correlation of means and differences).

Figure 22G:
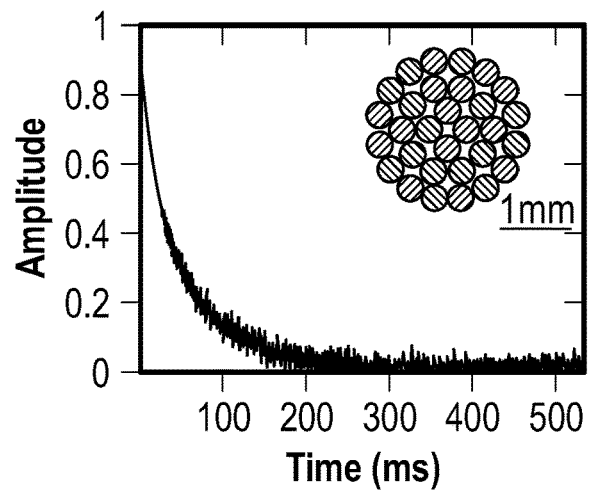
FIG. 22G is a graph showing an example of an MR signal acquired with CPMG acquisition from a synthetic tissue phantom comprising equal parts fast (24 ms, dark blue) and slow (84 ms, light blue) fluid compartments. Inset illustrates cross section of phantom.
Figure 22H:
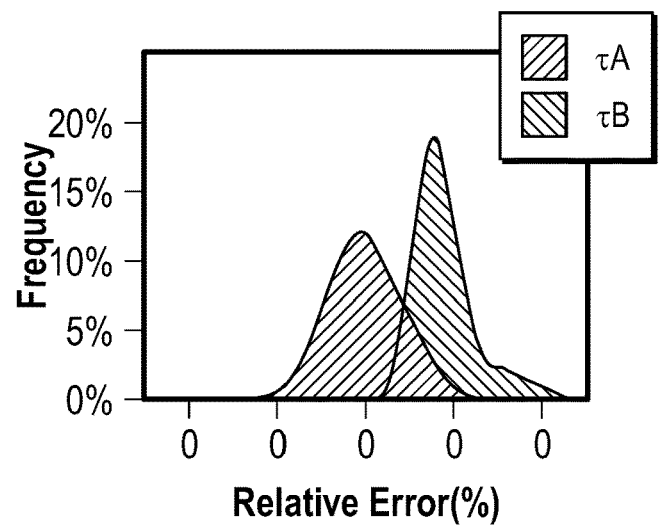
FIGS. 22H-22I are graphs showing an example of analyses of each component with a biexponential model, which demonstrate accurate identification and quantification of the decay rate ($\tau_A$, $\tau_B$) and relative amplitude ($A_A$, $A_B$) of each component. Repeated trials yield histograms of estimation error.
Figure 22I:
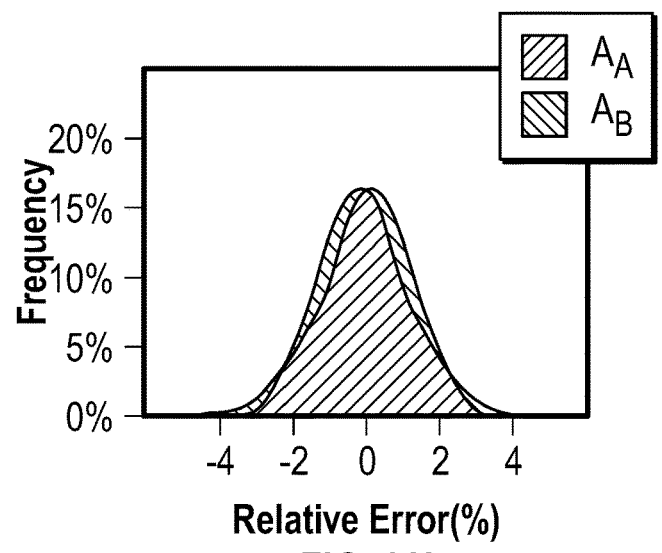

A heterogeneous synthetic tissue phantom consisting of two distinct compartments with unique T2 relaxation rates was measured using the portable MR sensor (FIG. 22G). Relaxation time constants and relative amplitudes of each fluid compartment can be accurately and reproducibly extracted from signals acquired by the MR sensor via T2 relaxometry (FIGS. 22H-22I). This exemplifies the ability to accurately quantify fluid distribution across a heterogeneous sample via a single-sided portable MR sensor. Multicomponent relaxometry is then applied towards quantification of fluid loss in an animal model of thermal dehydration.

Portable MR Sensor Design and Construction

The portable MR sensor was designed with the goal of achieving high sensitivity measurements remote from the surface of the sensor. The Unilateral Linear Halbach magnet geometry was utilized with an array of cube permanent magnets. Finite element analysis with COMSOL Multiphysics (Burlington, MA) was utilized to simulate the magnetic field profile of the magnet array. The magnet was parameterized by seven design parameters in order to constrain the dimensionality of the optimization problem as described in Bashyam, et al, *J. Magn. Reson.* 292:36-43 (2018)). The final values used for each parameter are as follows: Nx 6, Ny 6, Nz 5, gapX 2.23 mm, gapY 0.76 mm, gapZ 2.54 mm, and sliceDropY 5.1 mm.

The permanent magnets were custom fabricated 12.7 mm (0.5 inch) cube, grade N52 neodymium magnets (Viona Magnetics, Hicksville, NY) manufactured with a dimensional tolerance of 50.8 µm (0.002 inch). The magnets are contained within an aluminum assembly manufactured with a dimensional tolerance of 0.127 mm (0.005 inch) (Proto Labs, Maple Plain, MN). The RF transceiver coil was a 8-turn solenoid wound around a cylindrical PTFE bobbin with a diameter of 16 mm. The coil geometry was selected to maximize the sensitivity of the sensor. A narrowband "L" impedance matching network was placed approximately 8 cm from the transceiver coil. The matching network consisted of two high Q, tunable capacitors (Johanson Manufacturing). The first capacitor was placed in parallel with the transceiver coil and the other was placed in series with this parallel circuit. The matching circuit provides a precisely tunable impedance match at the Larmor frequency of the sensor.

Portable MR Sensor Characterization

The static magnetic field profile of the portable MR sensor was measured by scanning a hall probe (HMMT-6J04-VR, Lake Shore Cryotronics) connected to a gaussmeter (Model 475 DSP Gaussmeter) through a three-dimensional grid with 1 mm spacing. The uniform region was identified as the contiguous region which when excited with a 1% RF bandwidth would produce the strongest MR signal.

The two-dimensional sensitivity profiles were determined by measuring the relative signal strength produced by a 2 mm spherical sample of aqueous $CuSO_4$ solution scanned through planes perpendicular to the surface of the sensor. The relative signal strength was estimated from each scan as the relative amplitude of the peak corresponding to the spherical sample. This isolated the signal produced by the aqueous sample from background signal produced by the sensor.

The calibration curves of portable MR sensor R2 vs. paramagnetic species concentration (FIG. 22F, FIG. 21A) were acquired as follows: Aqueous $CuSO_4$ solutions were prepared at the following concentrations: 0 mM, 1.17 mM, 1.22 mM, 1.47 mM, 1.87 mM, 2.55 mM, 3.11 mM, 11.1 mM, 12.5 mM, 13.2 mM, 15.2 mM, 16 mM, 17.9 mM, 20.3 mM, 23.4 mM, 25.3 mM, 27.6 mM, 30.4 mM, and 38 mM. Portable MR measurements were performed with the CPMG pulse sequence with 8192 echoes, an echo time of 65 µs, a repetition time of 1032.5 ms, an RF excitation frequency of 11.66 MHz, a pulse duration of 12 µs, an acquisition bandwidth of 2 MHz (dwell time of 0.5 µs), and 16 acquired points per echo with a Kea2 spectrometer (Magritek, Wellington, New Zealand). The data for the calibration curve from the benchtop NMR spectrometer were acquired via CPMG with 65535 echoes, an echo time of 426 µs, a repetition time of 27.94 seconds, an RF excitation frequency of 19.95 MHz, an excitation pulse duration of 1.9 µs, an inversion pulse duration of 3.8 µs, an acquisition bandwidth of 1 MHz (dwell time of 3 µs), and 1 acquired point per echo with a (minispec mq20, Bruker, USA). Relaxation times were extracted by fitting the decay curves with a monoexponential model (Eq. (11)).

The heterogeneous synthetic tissue phantom (FIG. 22G) was constructed from 30 glass capillary tubes (1 mm diameter) arranged in a tightly packed circular formation (FIG. 22G inset). Two equal sets of tubes were filled with the requisite concentrations of aqueous $CuSO_4$ solution to produce T2 relaxation times of 24 ms (29 mM) and 84 ms (5 mM). The tubes were arranged randomly. Measurements were performed with the CPMG pulse sequence with 8192 echoes, an echo time of 65 µs, a repetition time of 1032.5 ms, an RF excitation frequency of 11.64 MHz, a pulse duration of 12 µs, an acquisition bandwidth of 2 MHz (dwell time of 0.5 µs), and 16 acquired points per echo with a Kea2 spectrometer (Magritek, Wellington, New Zealand). Amplitudes were extracted by fitting the decay curves with a biexponential model (Eq. (11)). Repeated trials were performed to yield histograms of estimation error (FIGS. 22H-I).

Multiexponential Fitting

CPMG T2 decay curves were estimated as a multiexponential signal in order to extract relaxation times ($\tau_i$) and relative amplitudes ($A_i$). When more than one point was collected for each echo, echo integrals were computed as the sum of the points sampled for each echo during CPMG. A general multicomponent exponential decay signal can be represented as:

$$\hat{y}(t, A, \tau) = \sum_{i=1}^{N} A_i * \exp(-t/\tau_i) \quad (10)$$

where ŷ(t) is the estimated signal, N is the number of components, A is a vector of amplitudes, and τ is a vector of corresponding relaxation times. Two types of models were used to represent the multicomponent nature of these signals. The first optimizes over both the relaxation times and relative amplitudes. The optimal set of parameters is found by minimizing the L2-norm of the residuals between the estimated and the measured signal:

$$A^{opt}, \tau^{opt} = \underset{A,\tau}{\operatorname{argmin}} \|y(t) - \hat{y}(t)\|_2 \quad (11)$$

where y(t) is the measured signal and $\|\cdot\|_2$ represents the L2-norm. This model allows discovery of the relaxation times of a multiexponential signal. The second model optimizes only over the relative amplitudes as the relaxation times are specified as parameters:

$$A^{opt} = \underset{A}{\operatorname{argmin}} \|y(t) - \hat{y}(t, \tau)\|_2 \quad (12)$$

This more constrained model allows the amplitudes to be estimated more accurately. 95% confidence intervals for each parameter were computed assuming an asymptotic normal distribution for each estimate. Signal to noise ratio (SNR) was defined as the maximum magnitude value divided by the standard deviation of the noise. The noise distribution was estimated from the residuals of the fit.

Statistical Analysis

Statistics for linear fits (FIG. 22F) established significance through two-sided t test of linear model coefficients with a significance value of 5%.

For box and whisker plots, the centerline indicates the median, the limits of the box indicate 25th and 75th percentiles, and the limits of the whiskers indicate the minimum and maximum values.

Publications cited herein and the materials for which they are cited are specifically incorporated by reference. Modifications and variations of the methods and devices described herein will be obvious to those skilled in the art from the foregoing detailed description. Such modifications and variations are intended to come within the scope of the appended claims.

We claim:

1. A device for non-invasive sensing of tissue fluid distribution in a patient, the device comprising:
    a plurality of magnets configured to provide a static magnetic field source, wherein the magnets are configured to conform to the patient's lower leg;
    one or more RF coils connected to a pulse sequence generator which are configured to apply a varying magnetic field to the skeletal muscle tissues of the patient's lower leg and to detect a magnetic field generated within the skeletal muscle tissues of the patient's lower leg; and
    a signal acquisition and processor system configured to acquire localized signals from the patient's lower leg from the one or more RF coils and perform an NMR measurement of a relaxation parameter of hydrogen nuclei within a skeletal muscle tissue site of the patient and to determine, based on the localized signals, an absolute hydration status of the patient.

2. The device of claim 1, wherein the plurality of magnets comprises a plurality of permanent magnets arranged in a Halbach array.

3. The device of claim 1, wherein the plurality of magnets is configured to generate a magnetic field strength that is at least 0.01 T.

4. The device of claim 1, wherein the plurality of magnets is configured to generate a magnetic field strength that is at most 2 T.

5. The device of claim 1, wherein the one or more RF coils are configured to be used in close proximity to the skin of the patient.

6. The device of claim 1, wherein the device is portable, hand-held, wearable, and/or configured for temporary attachment to the patient's lower leg.

7. The device of claim 1, wherein the skeletal muscle tissues are the calf muscle.

8. The device of claim 1, wherein the device is configured to use depth-resolved, diffusion-weighted, single-sided magnetic resonance (MR) to measure the relaxation parameter within the skeletal muscle tissues of the patient.

9. The device of claim 1, wherein the device is configured to use a combination of multicomponent T2 relaxometry, measurement localization, and diffusion weighting to identify shifts in intramuscular fluid distribution.

10. The device of claim 9, wherein the measurement localization comprises tuning RF excitation frequency to enable measurements at an increased tissue depth while substantially avoiding more proximal subcutaneous tissue.

11. The device of claim 9, wherein the diffusion weighting comprises varying echo time effect to substantially isolate an MR signal towards the skeletal muscle tissues.

12. The device of claim 1, which is configured to identify onset, progression, and recovery of muscle edema despite the presence of a confounding subcutaneous tissue layer.

13. The device of claim 1, wherein the acquired localized signals are hybrid signals and the signal acquisition and processor system comprises a non-transitory computer-readable storage medium having stored thereon a computer program for estimating the fraction of tissues within the hybrid signals to minimize error between the acquired localized signal and a synthetic signal based on an estimated ratio of constituent tissues.

14. A single-sided MR sensor device comprising:
permanent magnets arranged in a unilateral linear Halbach array; and
one or more RF coils and a processor which are configured to produce localized depth-resolved, diffusion-weighted, multicomponent T2 relaxometry measurements of a lower leg of a patient and determine intracellular and interstitial fluid within skeletal muscle tissue of the patient based on the measurements, and to determine an absolute hydration status of the patient based on the localized measurements.

15. The device of claim 14, wherein the device is configured to produce measurements of only the skeletal muscle tissue.

16. The device of claim 14, wherein the magnets have a concave shape or are elastically deformable, so as to conform or be conformable to a contour of the patient's body.

17. The device of claim 16, wherein the magnets have a concave shape or are elastically deformable, so as to conform or be conformable to the patient's lower leg.

18. The device of claim 14, wherein the magnets include adjustment shims.

19. The device of claim 14, further comprising:
(i) a circuit configured to provide a broadband match across a wide range of frequencies or rapid, automated tuning, or
(ii) gradient encoding coils to facilitate diffusion-weighted acquisition, or
(iii) multiple transceiver coils for parallel acquisition at different points of the patient's body, or
(iv) a combination of (i), (ii), and (iii).

* * * * *